United States Patent
Bayley et al.

(10) Patent No.: US 9,831,010 B2
(45) Date of Patent: Nov. 28, 2017

(54) HYDROGEL NETWORK

(71) Applicant: ISIS INNOVATION LIMITED, Oxford (GB)

(72) Inventors: John Hagan Pryce Bayley, Oxford (GB); Kunwar Tanuj Sapra, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 14/438,345

(22) PCT Filed: Oct. 25, 2013

(86) PCT No.: PCT/GB2013/052794
§ 371 (c)(1),
(2) Date: Apr. 24, 2015

(87) PCT Pub. No.: WO2014/064459
PCT Pub. Date: May 1, 2014

(65) Prior Publication Data
US 2015/0248949 A1 Sep. 3, 2015

Related U.S. Application Data

(60) Provisional application No. 61/718,343, filed on Oct. 25, 2012.

(30) Foreign Application Priority Data

Oct. 25, 2012 (GB) .................................. 1219201.9

(51) Int. Cl.
*H01B 7/00* (2006.01)
*C08J 3/075* (2006.01)
(Continued)

(52) U.S. Cl.
CPC ............. *H01B 7/0027* (2013.01); *B32B 9/00* (2013.01); *B32B 17/06* (2013.01); *C08J 3/075* (2013.01);
(Continued)

(58) Field of Classification Search
CPC ..................................... H01B 7/0027
(Continued)

(56) References Cited

U.S. PATENT DOCUMENTS 5,858,399 A   1/1999   Lanza
6,962,747 B1   11/2005   Sasaki et al.
(Continued)

FOREIGN PATENT DOCUMENTS

CA   2 564 120 A1   8/1998
EP   1 707 965 A1   10/2006
(Continued)

OTHER PUBLICATIONS

Sarles et al., "Cell-inspired electroactive polymer materials incorporating biomolecular materials": Electroactive Polymer Actuators and Devices (EAPAD) 2011, edited by Yoseph Bar-Cohen, Federico Carpi, Proc. of SPIE vol. 7976, 797626 • © 2011 SPIE.*
(Continued)

*Primary Examiner* — Brent O'Hern
(74) *Attorney, Agent, or Firm* — Hamilton, Brook, Smith & Reynolds, P.C.

(57) ABSTRACT

The invention provides a hydrogel network comprising a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects. A process for producing the hydrogel networks is also provided. The
(Continued)

Shapes     Oil / lipid mixture     Lipid monolayer self-assembly     Bilayer invention also provides an electrochemical circuit and hydrogel component for mechanical devices comprising a hydrogel network. Various uses of the hydrogel network are also described, including their use in synthetic biology and as components in electrochemical circuits and mechanical devices.

17 Claims, 12 Drawing Sheets

(51) Int. Cl.
    *C12M 1/12* (2006.01)
    *C12M 1/34* (2006.01)
    *G01N 27/416* (2006.01)
    *G01N 33/68* (2006.01)
    *H01H 1/00* (2006.01)
    *H01H 1/021* (2006.01)
    *H01L 51/00* (2006.01)
    *B32B 9/00* (2006.01)
    *B32B 17/06* (2006.01)
    *H01B 1/06* (2006.01)
    *H01B 3/00* (2006.01)
    *H05K 1/03* (2006.01)

(52) U.S. Cl.
    CPC ............ *C12M 1/34* (2013.01); *C12M 1/3407* (2013.01); *C12M 25/14* (2013.01); *G01N 27/416* (2013.01); *G01N 33/6872* (2013.01); *H01B 1/06* (2013.01); *H01B 3/00* (2013.01); *H01H 1/0036* (2013.01); *H01H 1/021* (2013.01); *H01L 51/00* (2013.01); *H05K 1/0306* (2013.01); *H05K 1/0326* (2013.01); *B32B 2457/00* (2013.01); *C08J 2305/12* (2013.01); *H05K 2201/0162* (2013.01); *Y10T 156/10* (2015.01); *Y10T 428/26* (2015.01); *Y10T 428/31971* (2015.04)

(58) Field of Classification Search
    USPC .......................................................... 428/53
    See application file for complete search history.

(56) References Cited

U.S. PATENT DOCUMENTS

| | | | |
|---|---|---|---|
| 8,992,984 | B1 | 3/2015 | Brinker et al. |
| 2003/0035842 | A1 | 2/2003 | Kazakov et al. |
| 2004/0191518 | A1 | 9/2004 | Naito et al. |
| 2007/0248541 | A1 | 10/2007 | Tagawa et al. |
| 2007/0293449 | A1 | 12/2007 | Cui et al. |
| 2009/0074988 | A1 | 3/2009 | Faris et al. |
| 2009/0289213 | A1 | 11/2009 | Pipper et al. |
| 2010/0032627 | A1 | 2/2010 | Bayley et al. |
| 2010/0147450 | A1 | 6/2010 | Takeuchi et al. |
| 2010/0173394 | A1 | 7/2010 | Colston, Jr. et al. |
| 2011/0041978 | A1 | 2/2011 | Wallace |
| 2011/0076734 | A1 | 3/2011 | Zhou et al. |
| 2011/0250688 | A1 | 10/2011 | Hasan |
| 2012/0116568 | A1 | 5/2012 | Murphy et al. |
| 2012/0220481 | A1 | 8/2012 | Wallace et al. |
| 2014/0356289 | A1 | 12/2014 | Bayley et al. |
| 2015/0248949 | A1 | 9/2015 | Bayley et al. |
| 2015/0270043 | A1 | 9/2015 | Bayley et al. |
| 2016/0136888 | A1 | 5/2016 | Bayley et al. |

FOREIGN PATENT DOCUMENTS

| | | |
|---|---|---|
| EP | 2 253 378 | 11/2010 |
| GB | 1119032.9 | 7/1968 |
| JP | 2001505224 | 4/2001 |
| JP | 2001-515853 | 9/2001 |
| JP | 2001-1515853 | 9/2001 |
| JP | 2010536551 | 2/2010 |
| JP | 2010-503417 | 4/2010 |
| JP | 2010222282 | 10/2010 |
| JP | 2012/166159 | 9/2012 |
| KR | 20120038662 | 4/2012 |
| WO | WO 91/00084 A1 | 1/1991 |
| WO | WO 98/33483 | 8/1998 |
| WO | WO 99/12523 | 3/1999 |
| WO | WO 2005/053643 A1 | 6/2005 |
| WO | WO 2006/009657 A1 | 1/2006 |
| WO | WO 2006/096571 A2 | 3/2006 |
| WO | WO 2006/096571 A1 | 9/2006 |
| WO | WO 2007/010668 A1 | 1/2007 |
| WO | WO 2007/094739 A1 | 8/2007 |
| WO | WO 2007/101174 A2 | 9/2007 |
| WO | WO 2008/012552 A1 | 1/2008 |
| WO | WO 2008012552 A1 * | 1/2008 ......... G01N 33/5432 |
| WO | WO 2008/034180 A1 | 3/2008 |
| WO | WO 2009/024775 A1 | 2/2009 |
| WO | WO 2009/049089 A1 | 4/2009 |
| WO | WO 2009/148598 A1 | 12/2009 |
| WO | WO 2010503417 | 4/2010 |
| WO | WO 2010/110471 A1 | 9/2010 |
| WO | WO 2011/015870 A1 | 2/2011 |
| WO | WO 2012/050359 A2 | 4/2012 |
| WO | WO 2013/041983 A1 | 3/2013 |
| WO | WO 2013/064837 | 5/2013 |
| WO | WO 2014/064459 A2 | 5/2014 |
| WO | WO 2014/064461 A1 | 5/2014 |
| WO | WO 2014/087175 A2 | 6/2014 |

OTHER PUBLICATIONS

Sarles et al., "Bilayer Formation between Lipid-Encased Hydrogels Contained in Solid Substrates": ACS, Applied Materials & Interfaces, vol. 2 • No. 12 • 3654-3663 • 2010.*
Pays, K., et al., "Coalescence in Surfactant-Stabilized Double Emulsions", *Langmuir*, 17: 7758-7769 (2001).
Rojas, E., et al., "Temperature-Induced Protein Release from Water-in-Oil-in-Water", *Langmuir*, 24: 7154-7160 (2008).
Wang et al., "Iposomes in Double-Emulsion Glogules," *Langmuir*, 26(5): 3225-3231 (2010).
European Search Report for European Patent Application No. 13 805 487.9, "Droplet Assembly by 3D Printing", dated Jun. 21, 2016.
Non-Final Office Action for U.S. Appl. No. 14/354,706, "Multisomes: Encapsulated Droplet Networks" dated Sep. 9, 2016.
U.S. Appl. No. 61/592,062, Multisomes: Encapsulated Droplet Networks, filed Jan. 30, 2012.
International Search Report and Written Opinion from International Application No. PCT/GB2013/052794; Filing Date: Oct. 25, 2013; Entitled: "Hydrogel Network"; dated Jul. 1, 2014.
International Preliminary Report on Patentability from International Application No. PCT/GB2013/052794; Filing Date: Oct. 25, 2013; Entitled: "Hydrogel Network", dated Apr. 28, 2015.
International Search Report and Written Opinion from International Application No. PCT/GB2013/052796; Filing Date: Oct. 25, 2013; Entitled: "Droplet Assembly Method", dated Jan. 28, 2014.
International Preliminary Report on Patentability from International Application No. PCT/GB2013/052796; Filing Date: Oct. 25, 2013; Entitled: "Droplet Assembly Method", dated Apr. 28, 2015.
International Search Report and Written Opinion from International Application No. PCT/GB2013/053229; Filing Date: Dec. 6, 2013; Entitled: "Droplet Assembly by 3D Printing," dated Jun. 17, 2014.
International Preliminary Report on Patentability from International Application No. PCT/GB2013/053229; Filing Date: Dec. 6, 2013; Entitled: "Droplet Assembly by 3D Printing"; dated Jun. 9, 2015.
International Search Report and Written Opinion from International Application No. PCT/GB2012/052736, entitled: "Multisomes: Encapsulated Droplet Networks", dated Apr. 25, 2013.
International Preliminary Report on Patentability from International Application No. PCT/GB2012/052736, entitled: "Multisomes: Encapsulated Droplet Networks", dated May 6, 2014.
Abbott, A., "Biology's new dimension", *Nature*, 424: 870-872 (Aug. 21, 2003).

(56) References Cited

OTHER PUBLICATIONS

Abramoff, M. D., et al., "Image processing with Image J", *Biophotonics International*, 11: 36-42 (2004).

Aghdaei, S., et al., "Formation of artificial lipid bilayers using droplet dielectrophoresis", *Lab Chip*, 8: 1617-1620 (2008).

Akashi, K., et al., "Preparation of Giant Liposomes in Physiological Conditions and Their Characterization Under an Optical Microscope", *Biophysical Journal*, 71: 3242-3250 (Dec. 1996).

Aronson, M. P. and Princen, H. M., "Contact angles associated with thin liquid-films in emulsions", *Nature*, 286: 370-372 (Jul. 24, 1980).

Astier, Y., et al, "Protein components for nanodevices", *Current Opinion in Chemical Biology* 9: 576-584 (2005).

Bai, Y. et al., "A double droplet trap system for studying mass transport across a droplet-droplet interface", Lab Chip, 10: 1281-1285 (2010).

Bayley, H. et al., "Droplet interface bilayers", *Molecular BioSystems*, 4(12): 1191-1208 (Dec. 2008).

Bodor, N. and Buchwald, P., "Soft Drug Design: General Principles and Recent Applications", *Med. Res. Rev.*, 20:58-101 (2000).

Boland, Thomas et al., "Application of inkjet printing to tissue engineering", *Biotechnology Journal*, 1: 910-917 (2006).

Bolinger, P.-Y. et al., "Integrated Nanoreactor Systems: Triggering the Release and Mixing of Compounds Inside Single Vesicles", *J. Am. Chem. Soc.*, 126(28): 8594-8595 (2004).

Boroske, E., and Elwenspoek, M., "Osmotic Shrinkage of Gian Egg-Lecithin Vesicles", *Biophys. J.*, 34: 95-109 (Apr. 1981).

Bowden, N., et al., "Molecule-Mimetic Chemistry and Mesoscale Self-Assembly", Acc. Chem. Res. 34(3): 231-238 (2001).

Bowden, N., et al., "Self-Assembly of Mesoscale Objects into Ordered Two-Dimensional Arrays", *Science*, 276: 233-235 (Apr. 11, 1997).

Channon, K., et al., "Synthetic biology through biomolecular design and engineering", *Current Opinion in Structural Biology*, 18: 491-498 (2008).

Cheley, S. et al., "Spontaneous oligomerization of a staphylococcal alpha-hemolysin conformationally constrained by removal of residues that form the transmembrane beta-barrel", *Protein Engineering*, 10: 1433-1443 (1997).

Chiarabelli, C. et al., "Chemical approaches to synthetic biology", *Current Opinion in Biotechnology*, 20: 492-497 (2009).

Choi, I. S. et al., "Macroscopic Hierarchial, Two-Dimensional Self-Assembly", *Angew. Chem. Int. Ed*, 38(20): 3078-3081 (1999).

Chu, C.-J. et al., "Efficiency of Cytoplasmic Delivery by pH-Sensitive Liposomes to Cells in Culture", *Pharmaceutical Research*, 7(8): 824-834 (1990).

Chu, L.-Y. et al., "Controllable Monodisperse Multiple Emulsions", *Angew. Chem. Int. Edit.*, 46: 8970-8974 (2007).

Clancy, K. and Voigt, C. A., "Programming cells: towards an automated 'Genetic Compiler'", *Current Opinion in Biotechnology*, 21: 572-581 (2010).

Clavel, F. and Hance, A. J., "Medical Progress HIV Drug Resistance", *New England Journal of Medicine*, 350(10): 1023-1035 (Mar. 4, 2004).

Cukierman, E. et al, "Cell interactions with three-dimensional matrices", *Current Opinion in Cell Biology*, 14: 633-639 (2002).

Cukierman, E. et al, "Taking Cell-Matrix Adhesions to the Third Dimension", *Science*, 294: 1708-1712 (Nov. 23, 2001).

Devine, D. V., et al., "Liposome-complement interactions in rat serum: implications for liposome survival studies", *Biochim. Biophys. Acta*, 1191: 43-51 (1994).

Dixit, S. S., et al., "Droplet Shape Analysis and Permeability Studies in Droplet Lipid Bilayers", Langmuir, 28: 7442-7451 (2012).

Dixit, S. S., et al., "Light-Driven Formation and Rupture of Droplet Bilayers", Langmuir 26(9): 6193-6200 (2010).

Drummond, D. C. et al., "Current status of pH-sensitive liposomes in drug delivery", *Progress in Lipid Research*, 39: 409-460 (2000).

Du, Y., et al., "Directed assembly of Cell-laden microgels for fabrication of 3D tissue constructs", *Proc. Natl. Acad. Sci. (PNAS)*, 105(28): 9522-9527 (2008).

Evans, E., "Probing the Relation Between Force-Lifetime—and Chemistry in Single Molecular Bonds," *Annu. Rev. Biophys. Biomol. Struct.*, 30:105-128 (2001).

Forterre, Y., et al., "How the Venus Flytrap Snaps," *Nature*, 43:421-425 (2005).

Funakoshi, et al., "Lipid Bilayer Formation by Contacting Monolayers in a Microfluidic Device for Membrane Protein Analysis," *Anal. Chem.*, 78(24): 8169-8174 (2006).

Gibson, D. G. et al., "Creation of a Bacterial Cell Controlled by a Chemically Synthesized Genome," *Science*, 329:52-56 (2010).

Gijs, M. A., et al., "Microfluidic Applications of Magnetic Particles for Biological Analysis and Catalysis," *Chem. Rev.*, 110:1518-1563 (2010).

Gross, L.C., et al., "Determining Membrane Capacitance by Dynamic Control of Droplet Interface Bilayer Area," *Langmuir*, 27:14335-14342 (2011).

Gu, L. Q., et al, "Stochastic Sensing of Organic Analytes by a Pore-Forming Protein Containing a Molecular Adapter," *Nature*, 398:686-690 (1999).

Gu, L. Q., et al., "Interaction of the noncovalent molecular adapter, betacyclodextrin, with the staphylococcal alpha-hemolysin pore," *Biophys. J.*, 79:1967-1975 (2000).

Hamer, W. J., et al., "Osmotic Coefficients and Mean Activity Coefficients of Uni-Univalent Electrolytes in Water at 25° C.," *J. Phys. Chem. Ref. Data*, 1:1047-1100 (1972).

Hamilton, J. A., et al., "Transfer of Oleic Acid Between Albumin and Phosphholipid Vesicles," *Proc. Natl Acad. Sci. USA*, 83:82-86 (1986).

Harada, A., et al., "Macroscopic Self-Assembly Through Molecular Recognition," *Nat. Chem.* 3:34-37 (2011).

Harada, et al., "Bubble wrap of cell-like aggregates", *Nature*, 471:172-175 (2011).

Harriss, L. M., et al., "Imaging Multiple Conductance States in an Alamethicin Pore," *J. Am. Chem. Soc.*, 133:14507-14509 (2011).

Heron, A.J., et al., "Direct detection of membrane channels from gels using water-in-oil droplet bilayers," *J. Am. Chem. Soc.*, 129:16042-16047 (2007).

Heron, A. J., et al., "Simultaneous measurement of ionic current and fluorescence from single protein pores," *J. Am. Chem. Soc.*, 131:1652-1653 (2009).

Holden, M. A., et al., "Functional bionetworks from nanoliter water drops," *J. Am. Chem. Soc.*, 129:8650-8655 (2007).

Hu, Z. B., et al., "Synthesis and Application of Modulated Polymer Gels," *Science*, 269: 525-527 (1995).

Huang, J., et al., "Direct Quantitation of Peptide-Mediated Protein Transport across a Droplet-Interface Bilayer," *JACS*, 133:15818-15821 (2011).

Humphrey, W., et al.,"VMD: Visual Molecular Dynamics," *J. Molec. Graphics*, 14:33-38 (1996).

Hwang, W. L., et al., "Electrical Behavior of Droplet Interface Bilayer Networks: Experimental Analysis and Modeling," *JACS*, 129:11854-11864 (2007).

Jeong, B., et al., "Lessons from Nature: Stim uli-Responsive Polymers and their Biomedical Applications," *Trends Biotechnol.*, 20:305-311 (2002).

Johnson, J. D., "Intracellular EDTA mimics parvalbumin in the promotion of skeletal muscle relaxation", *Biophys. J.* 76:1514-1522 (1999).

Kankare, J. et al., "Kinetics of Langmuirian Adsorption onto Planar, Spherical, and Cylindrical Surfaces," Langmuir,15:5591-5599 (1999).

Kim, J., et al., "Designing Responsive Buckled Surfaces by Halftone Gel Lithography," Science,335:1201-1205 (2012).

Klein, Y., et al., "Shaping of Elastic Sheets by Prescription of Non-Euclidean Metrics," Science,315:1116-1120 (2007).

Korlach, J. et al., "Characterization of lipid bilayer phases by confocal microscopy and fluorescence correlation spectroscopy", *Proc. Natl. Acad. Sci. USA*, 96, 8461-8466 (1999).

Lahann, J., et al., "A Reversibly Switching Surface," *Science*, 299:371-374 (2003).

Lehmann, et al., "Two-dimensional magnetic manipulation of microdroplets on a chip as a platform for bioanalytical application," *Sensors and Actuators B*, 2(117):457-463 (2006).

(56) References Cited

OTHER PUBLICATIONS

Leptihn, S., et al., "In Vitro Reconstitution of Eukaryotic Ion Channels Using Droplet Interface Bilayers," *J. Am. Chem. Soc.*, 133:9370-9375 (2011).
Leunissen, M. E. et al., "Switchable Self-Protected Attractions in DNA-Functionalized Colloids," *Nat. Mater*, 8:590-595 (2009).
Levental, I., et al., "Soft Biological Materials and Their Impact on Cell Function," *Soft Matter*, 3:299-306 (2007).
Liang, H. Y., et al., "Growth, Geometry, and Mechanics of a Blooming Lily," *Proc. Natl. Acad. Sci. USA*, 108:5516-5521 (2011).
Lichtenberg, D. et al., "Effect of surface curvature on stability, thermodynamic behavior, and osmotic activity of dipalmitoylphosphatidylcholine single lamellarvesicles," *Biochemistry (Mosc.)*, 20:3462-3467 (1981).
Lindsey, H., et al.,"Physicochemical characterization of 1,2-diphytanoyl-sn-glycero-3-phosphocholine in model membrane systems," *Biochim. Biophys. Acta*, 555:147-167 (1979).
Maglia, G. et al., "Analysis of single nucleic acid molecules with protein nanopores," *Method. Enzymol.* 475:591-623 (2010).
Maglia, G. et al., "Droplet networks with incorporated protein diodes show collective properties," *Nat. Nanotechn*,1(4):437-440 (2009).
Maglia, M. et al., "DNA strands from denatured duplexes are translocated through engineered protein nanopores at alkaline pH.," *Nano Lett.*, 9:3831-3836 (2009).
Mills, J. K., et al., "Lysolipid incorporation in dipalmitoylphosphatidylcholine bilayer membranes enhances the ion permeability and drug release rates at the membrane phase transition," *BBA-Biomembranes*, 1716:77-96 (2005).
Morisaku, T., et al., "Development of a new experimental system for monitoring biomembrade reactions: combinatin of laser spectroscopic techniques and biomembrane models formed at an oil/water interfacez," *Anal. Sci.*,20:1605-1608 (2004).
Nakagawa, S., et al., "Structural and functional studies of gap junction channels," *Curr. Opin. Struc. Biol.*, 20:423-430 (2010).
Naraghi, M., "T-jump study of calcium binding kinetics of calcium chelators," *Cell Calcium*, 22:255-268 (1997).
Nath, U., et al., "Genetic Control of Surface Curvature," *Science*, 299:1404-1407 (2003).
Needham, D. , et al., "The development and testing of a new temperature-sensitive drug delivery system for the treatment of solid tumors," *Adv. Drug Deliver. Rev.*, 53:285-305 (2001).
Niculescu-Duvaz, I., et al., "Antibody-directed enzyme prodrug therapy (ADEPT): a review," *Adv. Drug Deliver. Rev.*, 26:151-172 (1997).
Noireaux, V., et al., "A Vesicle Bioreactor as a sStep Toward an Artificial Cell Assembly," Proc. Natl. Acad. Sci. USA, 101:17669-17674 (2004).
Noireaux, V., et al., "Development of an Artificial Cell, from Self-Organization to Computation and Self-Reproduction," *Proc. Natl. Acad. Sci., USA*, 108:3473-3480 (2011).
Okushima, S., et al., "Controlled production of monodisperse double emulsions by two-step droplet breakup in microfluidic devices," *Langmuir*, 20:9905-9908 (2004).
Payne, G. F., "Biopolymer-Based Materials: The Nanoscale Components and their Hierarchical Assembly," *Curr. Opin. Chem. Biol.*, 11:214-219 (2007).
Poulin et al., "Influence of the Alkyl Surfactant Tail on the Adhesion Between Emulsion Drops," J. Phys. Chem. B, 103(25)5157-5159 (1999).
Poulin, P., et al.,"Adhesion of Water Droplets in Organic Solvent," Langmuir, 14: 6341-6343 (1998).
Poulos, J. L., et al., "Electrowetting on Dielectric-Based Microfluids for Integrated Lipid Bilayer Formation and Measurement," *Appl. Phys. Lett.*, 95:013706 (2009).
Pouponneau, P., et al., "Co-encapsulation of magnetic nanoparticles and doxorubicin into biodegradable microcarriers for deep tissue targeting by vascular MRI navigation," *Biomaterials*,32:3481-3486 (2011).
Rautio, J. et al., "Prodrugs: design and clinical applications," *Nat. Rev. Drug Discov.*, 7: 255-270 (2008).
Raychaudhuri, P., et al., "Fluorinated Amphiphiles Control the Insertion of α-Hemolysin Pores into Lipid Bilayers," *Biochemistry* 50:1599-1606 (2011).
Ringeisen, B. R., et al., "Jet-based methods to print living cells", *Biotechnology Journal*,1:930-948 (2006).
Russew, M.-M., et al., "Photoswitches: From Molecules to Materials," *Adv. Mater*, 22: 3348-3360 (2010).
Sacanna, S., et al., Lock and Key Colloids, *Nature*,464:575-578 (2010).
Sanjana, N. E., et al., "A fast flexible ink-jet printing method for patterning dissociated neurons in culture," *Journal of Neuroscience Methods*, 136(2):151-163 (2004).
Sapra, K. T., et al., "Lipid-coated hydrogel shapes as components of electrical circuits and mechanical devices," *Scientific Reports*,2(848):1-9 (2012).
Sapra, K. T., et al., "Three dimensional construction of bilayer networks using shape encoded hydrogel," *Biophysical Journal*, 100(3):502a (2011).
Sarles, S. A., et al., "Bilayer Formation between Lipid-Encased Hydrogels Contained in Solid Substrates," *ACS Applied Materials & Interfaces*, 2(12):3654-3663 (2010).
Sarles, S. A., et al., "Biomolecular material systems with encapsulated interface bilayers," *MRS Proceedings*, 1301, (2011).
Sarles, S. A., et al., "Cell-inspired electroactive polymer materials incorporating biomolecular materials" *Proceedings of SPIE*, 7976:797626-1-797626-9 (2011).
Schrum, J. P., et al., "The Origins of Cellular Life," Cold Spring Harb Perspect Biol 2, pp. 1-16 (2010).
Schwille, P., "Bottom-Up Synthetic Biology:Engineering in a Tinkerer's World," Science, 333: 1252-1254 (2011).
Seo, M. et al., "Microfluidic consecutive flow-focusing droplet generators," *Soft Matter* 3:986-992 (2007).
Sharon, E., et al., "Buckling Cascades in Free Sheets," *Nature*, 419: 579-579 (Oct. 10, 2002).
Sharon, E., et al., "Geometrically Driven Wrinkling Observed in Free Plastic Sheets and Leaves," *Phys. Rev. E*, 75, 7 pages (2007).
Shum, H. C. et al., "Multicompartment Polymersomes from Double Emulsions" *Angew. Chem. Int. Edit.*, 50: 1648-1651 (2011).
Sidorenko, A., et al., Reversible Switching of Hydrogel-Acutated Nanostructures into Complex Micropatterns, *Science*, 315: 487-490 (Jan. 26, 2007).
Skotheim, J. M. & Mahadevan, L., "Physical Limits and Design Principles for Plant and Fungal Movements," *Science*, 308: 1308-1310 (May 27, 2005).
Small, D. M., et al., "The Ionization Behavior of Fatty Acids and Bile Acids in Micelles and Membranes," *Hepatology*, 4: 77S-79S (1984).
Solé, R. V. et al., "Synthetic Protocell Biology: From Reproduction to Computation", *Philos. T. R. Soc. B*, 362: 1727-1739 (2007).
Stanley, C.E. et al., "A Microfluidic Approach for High-Throughput Droplet Interface Bilayer (DIB) Formation," *Chem Commun*, 46: 1620-1622 (2010).
Stoddart, D. et al., "Single-Nucleotide Discrimination in Immobilized DNA Oligonucleotides with a Biological Nanopore," *Proc. Natl. Acad. Sci. USA*, 106: 7702-7707 (May 12, 2009).
Strambio-De-Castillia, C. et al., "The Nuclear Pore Complex: Bridging Nuclear Transport and Gene Regulation," *Nat. Rev. Mol. Cell Bio.*, 11: 490-501 (Jul. 2010).
Syeda, R. et al., "Screening Blockers Against a Potassium Channel with a Droplet Interface Bilayer Array", *J. Am. Chem. Soc.*, 130: 15543-15548 (2008).
Synytska, A. et al., "Simple and Fast Method for the Fabrication of Switchable Bicomponent Micropatterned Polymer Surfaces," *Langmuir*, 23: 5205-5209 (2007).
Szostak, J.W., et al., "Synthesizing Life," *Nature*, 409: 387-390 (Jan. 18, 2001).
Tamaddoni, N. J. et al., "Fabricating Neuromast-Inspired Gel Structures for Membrane-Based Hair Cell Sensing," *Proceedings of SPIE*, vol. 8339: 833908-1-833908-11 (Apr. 3, 2012).

(56) References Cited

OTHER PUBLICATIONS

Theberge, A.B. et al., "Microdroplets in Microfluidics: An Evolving Platform for Discoveries in Chemistry and Biology," *Angew Chem. Int. Ed.*, 49: 5846-5868 (2010).
Tokarev, I. & Minko, S., "Stimuli-Responsive Porous Hydrogels at Interfaces for Molecular Filtration, Separation, Controlled Release, and Gating in Capsules and Membranes," *Adv. Mater*, 22: 3446-3462 (2010).
Torchilin, V. P., "Recent Advances with Liposomes as Pharmaceutical Carriers," *Nat. Rev. Drug Discov.*, 4: 145-160 (Feb. 2005).
Tsuchiya et al., "On-Chip Polymerase Chain Reaction Microdevice Employing a Magnetic Droplet-Manipulation System," *Sensors and Actuators B*, 130(2): 583-588 (2008).
Tuteja, A. et al., "Robust Omniphobic Surfaces," *Proc. Natl. Acad. Sci.*, 105: 18200-18205 (Nov. 25, 2008).
Ueno, M., et al., "Characteristics of the Membrane Permeability of Temperature-Sensitive Liposome," *Bull. Chem. Soc. Jpn.*, 64: 1588-1593 (1991).
Velev, O. D., et al., "On-Chip Manipulation of Free Droplets," *Nature*, 426: 515-516 (2003).
Villar, G., et al., "Formation of Droplet Networks that Function in Aqueous Environments," *Nat. Nanotechnol.*, 6: 803-808 (2011).
Walsh, C., "Molecular Mechanisms that Confer Antibacterial Drug Resistance," *Nature*, 406: 775-781 (Aug. 17, 2000).
Wang et al., "Controllable Microfluidic Production of Multicomponent Multiple Emulsions," RSC, *Lab Chip*, 11, 7 pages (2011).
Weibel, D. B. & Whitesides, G.M., "Applications of Microfluidics in Chemical Biology," *Curr. Opin. Chem. Biol.*, 10: 584-591 (2006).
Wheeldon, I., et al., "Nanoscale Tissue Engineering: Spatial Control over Cell-Materials Interactions," *Nanotechnology*, 22: 212001, 16 pages (2011).
White, N. "Antimalarial Drug Resistance and Combination Chemotherapy," *Phil. Trans. R. Soc. Lond. B*, 354: 739-749 (1999).
Whitesides, G. M., "The Origins and the Future of Microfluidics," *Nature*, 442: 368-373 (Jul. 27, 2006).
Williamson, A. J., et al,, "Templated Self-Assembly of Patchy Particles," *Soft Matter*, 7: 3423-3431 (2011).
Woolfson, D. N. & Bromley, E. H. C., "Synthetic Biology: A Bit of Rebranding, or Something New and Inspiring?" *Biochemist e-volution*, 33(1): 19-25 (Feb. 2011).
Wu, L.-Q. & Payne, G.F., Biofabrication: Using Biological Materials and Biocatalysts to Construct Nanostructured Assemblies, *Trends Biotechnol.*, 22(11): 593-599 (Nov. 2004).
Xu, G. & McLeod, H. L., "Strategies for Enzyme/Prodrug Cancer Therapy," *Clin. Cancer Res.*, 7: 3314-3324 (Nov. 2001).
Xu, J., et al., "Synthetic Protocells to Mimic and Test Cell Function," *Adv. Mater*. 22: 120-127 (2010).
Yamada, K. M. & Cukierman, E., "Modeling Tissue Morphogenesis and Cancer in 3D," *Cell*, 130: 601-610 (2007).
Yoo, J.-W. & Mitragotri, S., "Polymer Particles that Switch Shape in Response to a Stimulus," *Proc. Natl. Acad. Sci.*, 107(25): 11205-11210 (Jun. 22, 2010).
Yue, B. Y. et al., "Phospholipid Monolayers at Non-Polar Oil/Water Interfaces. Part 1—Phase Transitions in Distearoyl-lecithin Films at the n-Heptane Aqueous Sodium Chloride Interface," *J. Chem. Soc. Farad. T.*, 1(72): 2685-2693 (1976).
Zagnoni, M. et al., "A Microdroplet-Based Shift Register," *Lab Chip*, 10: 3069-3073 (2010).
Zelikin, A. N. et al., "Poly(Methacrylic Acid) Polymer Hydrogel Capsules: Drug Carriers, Sub-Compartmentalized Microreactors, Artificial Organelles," *Small*, 6(20): 2201-2207 (2010).
Zhu, J. & Marchant, R.E., "Design Properties of Hydrogel Tissue-Engineering Scaffolds," *Expert Rev. Med. Devices*, 8: 607-626 (2011).
Zimmerberg, J. & Kozlov, M. M., How Proteins Produce Cellular Membrane Curvature,: *Nat. Rev. Mol. Cell Bio*, 7: 9-19 (Jan. 2006).
Non-Final Office Action for U.S. Appl. No. 14/437,340, "Droplet Assembly Method" dated Nov. 4, 2016.

* cited by examiner (i) Assembly    (ii) Rotating the assembly    (iii) Disassembly

HYDROGEL NETWORK

This application is the U.S. National Stage of International Application No. PCT/GB2013/052794, filed on Oct. 25, 2013, which designates the U.S., published in English, and claims priority under 35 U.S.C. §§119 or 365(c) to Great Britain Application No. 1219201.9, filed on Oct. 25, 2012, and which claims the benefit of U.S. Provisional Application No. 61/718,343, filed on Oct. 25, 2012.

FIELD OF THE INVENTION

The invention relates to hydrogel networks and a process for producing the hydrogel networks. The invention also relates to electrochemical circuits and hydrogel components for mechanical devices comprising a hydrogel network. Various uses of the hydrogel networks are also described, including their use in synthetic biology and as components in electrochemical circuits and mechanical devices.

BACKGROUND TO THE INVENTION

Up to now, lipid vesicles have been the system of choice for the development of artificial cells (Chiarabelli, C., Stano, P. & Luisi, P. L. Curr Opin Biotechnol 20, 492-497 (2009); Noireaux, V., Maeda, Y. T. & Libchaber, A. Proc Natl Acad Sci USA 108, 3473-3480 (2011); Szostak, J. W., Bartel, D. P. & Luisi, P. L. Nature 409, 387-390 (2001)). However, the small size of these compartments limits their manipulation, including the ability to measure ionic currents through the bilayer envelopes.

Systems based on droplet interface bilayers (DIB) can be more readily controlled (Holden, M. A., Needham, D. & Bayley, H. J Am Chem Soc 129, 8650-8655 (2007)). A DIB is formed when two lipid-monolayer coated droplets in an oil are brought together. Several such droplets can be assembled to form a network, and when membrane proteins are included in the DIBs, functional systems are produced (Holden, M. A., Needham, D. & Bayley, H. J Am Chem Soc 129, 8650-8655 (2007)). DIBs have been used to study the fundamental properties of membrane proteins (Leptihn, S., Thompson, J. R., Ellory, J. C., Tucker, S. J. & Wallace, M. I. J Am Chem Soc 133, 9370-9375 (2011); Harriss, L. M., Cronin, B., Thompson, J. R. & Wallace, M. I. J Am Chem Soc 133, 14507-14509 (2011); Heron, A. J., Thompson, J. R., Mason, A. E. & Wallace, M. I. J Am Chem Soc 129, 16042-16047 (2007); Bayley, H. et al. Mol BioSystems 4, 1191-1208 (2008); Syeda, R., Holden, M. A., Hwang, W. L. & Bayley, H. J Am Chem Soc 130, 15543-15548 (2008); Heron, A. J., Thompson, J. R., Cronin, B., Bayley, H. & Wallace, M. I. J Am Chem Soc 131, 1652-1653 (2009)), and DIB networks have been used to construct devices (Bayley, H. et al. Mol BioSystems 4, 1191-1208 (2008)), including a light sensor (Holden, M. A., Needham, D. & Bayley, H. J Am Chem Soc 129, 8650-8655 (2007)), a battery (Holden, M. A., Needham, D. & Bayley, H. J Am Chem Soc 129, 8650-8655 (2007)), and half- and full-wave rectifiers (Maglia, G. et al. Nat Nanotechnol 4, 437-440 (2009)). Recently, droplet networks that function in aqueous media have been devised (Villar, G., Heron, A. & Bayley, H. Nat Nanotechnol 6, 803-808 (2011)). In a synthetic biology context, these networks can be regarded as minimal tissues (prototissues) (Woolfson, D. N. & Bromley, E. H. C. The Biochemist February, 19-25 (2011)).

Networks based on aqueous droplets can be delicate, which can limit their application. There is thus an ongoing need to develop more robust networks for a wide variety of application areas, including the area of synthetic biology. For example, robust 3-dimensional systems that incorporate engineered membrane proteins for inter-compartment communication are required.

SUMMARY OF THE INVENTION

The inventors have now provided a hydrogel network comprising a plurality of hydrogel objects which is both extremely robust and versatile. The networks can be structurally complex and functionally diverse, which means that they can be used in a wide variety of applications, including, for instance, in synthetic biology, electrochemical circuits and bio-mechanical devices.

The hydrogel objects used in the invention can be formed in a wide variety of different shapes and sizes. This is in contrast to existing aqueous droplet networks, which are inherently constrained by the spherical droplet shape. Hydrogel objects are also much more robust than aqueous drops.

Networks can be formed using hydrogel objects of just one shape or a number of different shapes. Further, the arrangement of hydrogel objects within the network can be manipulated and controlled.

This immediately provides much greater versatility when compared with existing aqueous droplet networks. Each network can be tailored to a specific use. One example of such tailoring is the use of wire-shaped hydrogel objects in a network. The wires, along with the connections formed at the interfaces between them, can form analogs of neurons.

In the hydrogel network of the invention, each hydrogel object comprises a hydrogel body and an outer layer of amphipathic molecules, on at least part of the surface of the hydrogel body. Each hydrogel object in the network contacts another hydrogel object to form an interface between contacting hydrogel objects. At the interfaces a bilayer of amphipathic molecules may be formed. Such a bilayer can act as a barrier to prevent diffusion of substances from one hydrogel body to the next hydrogel body, and can advantageously therefore help to contain or "store" particular chemicals within particular hydrogel bodies. On the other hand, the bilayers may be modified to allow the network to be functionalised in a variety of ways. For example, a membrane protein may be inserted into the bilayer enabling the flow of information across a network. As the hydrogel objects can be a variety of shapes, bilayers can be formed between the shaped hydrogel objects in geometries that cannot be achieved with spherical aqueous droplets.

Surprisingly, the inventors have also found that the bilayer can be effectively squeezed out from an interface by pushing together the two hydrogel objects at the interface. In contrast, when two aqueous droplets are pushed together either the bilayer remains intact or the droplets burst and fuse. Displacement of the bilayer maximises contact between the contacting surfaces of the hydrogel objects. This provides further advantages of the present invention, and can result in faster transport of ions through the network.

Further, the presence or absence of a bilayer can be controlled using a number of different methods. Thus networks can be formed which comprise at least one interface that comprises a bilayer of amphipathic molecules and/or at least one interface that does not comprise a bilayer of amphipathic molecules. This, combined with the flexibility discussed above, provides an unprecedented level of control over the network formed.

Individual hydrogel objects may further comprise an additional material or substance. For example, a hydrogel object may comprise a magnetic bead or magnet allowing the network to be used as a component for a mechanical device such as a switch or a rotor. Such applications would not be possible without the rigidity of the hydrogel interior of the hydrogel object.

Importantly, the hydrogel networks are also biocompatible. Thus, the networks of the invention could be used in applications such as synthetic biology and the delivery of therapeutic agents. For example, a network of synthetic tissues could be formed in which individual hydrogel objects may contain different therapeutic agents allowing for targeted delivery of combinations of therapeutic agents simultaneously to a patient. The delivery of the therapeutic agents may be delivery of the agents to a specific or defined site in a patient.

Hydrogel networks may, for example, form part of a droplet encapsulate. The droplet encapsulate, or "multisome", can communicate with the external environment through membrane proteins. In addition, membrane proteins allow hydrogel objects within the same multisome to communicate with each other. This in principle allows multisomes to sense their environment, process information, and contingently deliver materials to the surroundings.

Biological cells can be encapsulated in suitable hydrogel bodies of the hydrogel network. The hydrogel network could therefore take the form of a close-knit biological tissue network, with individual hydrogel objects separated by bilayers of amphipathic molecules. Different hydrogel bodies within the network may, for example, comprise different biological cells. The present invention also makes it possible to form a complex network comprising, for example, (i) a hydrogel object comprising a biological cell and (ii) a hydrogel object comprising a small molecule, such as a dye or a magnet, a sensor molecule, a therapeutic agent or a diagnostic agent, connected by an interface formed from a bilayer of amphipathic molecules comprising a membrane pore.

The hydrogel network may also comprise one or more "Janus particles". Janus particles are so called because they comprise both a hydrophilic material and a hydrophobic material. The Janus particle will assemble a bilayer-forming monolayer of amphipathic molecules only over the hydrophilic material, due to the difference in orientation of the amphipathic molecules on the surface of the hydrophilic material and the hydrophobic material. The presence of the hydrophilic material and the hydrophobic material also forms compartments within the Janus particle. An individual compartment may serve as a deposit for small molecules, such as dyes or magnets, sensor molecules, therapeutic agents or diagnostic agents. These may diffuse slowly into another compartment within the Janus particle, e.g., by forming a concentration gradient within the hydrogel body.

Accordingly, the invention provides a hydrogel network comprising a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects.

In some embodiments, at least one of the interfaces between contacting hydrogel objects comprises a bilayer of amphipathic molecules, and at least one other of the interfaces between contacting hydrogel objects does not comprise a bilayer of amphipathic molecules.

In a second aspect, the invention provides an electrochemical circuit comprising a network of hydrogel objects which network comprises a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects. In the electrochemical circuit of the invention, the current in the circuit is carried by ions and not by electrons.

The invention also provides a hydrogel component for a mechanical device, which hydrogel component comprises a hydrogel network, which network comprises a plurality of hydrogel objects, wherein each of said hydrogel objects comprises a hydrogel body, and an outer layer of amphipathic molecules, on at least part of the surface of the hydrogel body, wherein each of said hydrogel objects contacts another of said hydrogel objects to form an interface between the contacting hydrogel objects.

In a further aspect, the invention provides the use of a hydrogel network as defined herein in synthetic biology.

In another aspect, the invention provides the use of a hydrogel network as defined herein in preparing a protocell, or an aggregate of protocells (or "minimal cells").

In yet another aspect, the invention provides use of a hydrogel network as defined herein as a component of an electrochemical circuit or of a mechanical device.

The invention also provides a process for producing a hydrogel network comprising a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects; which process comprises: (i) introducing a plurality of hydrogel bodies into a medium comprising a plurality of amphipathic molecules; and (ii) assembling said hydrogel bodies into a said network, or allowing said hydrogel bodies to self-assemble into a said network.

In another aspect, the invention provides a process for producing a network of hydrogel objects as defined herein which further comprises recovering said network of hydrogel objects.

In yet another aspect, the invention provides a network of hydrogel objects which is obtainable by a process as defined hereinabove.

BRIEF DESCRIPTION OF THE FIGURES

FIG. 1*a* is a schematic of some possible three-dimensional shapes that the hydrogel body may adopt. The schematic also illustrates the formation of a lipid monolayer when the hydrogel body is immersed in a lipid/oil solution.

FIG. 1*b* is a schematic illustration of the bilayer formed at the interface of two lipid-coated shapes when the shapes are brought together with a micromanipulator.

FIG. 1*c* is a schematic illustration of a hydrogel network that comprises a bilayer at each interface of two hydrogel objects.

FIG. 1*d* illustrates that when the shapes are brought closer together, the bilayers rupture at the interfaces, and a network coated with a single external lipid monolayer is obtained. The positions of the hydrogel objects in any network of the invention may be changed to change the network topology.

FIG. 1*e* is a schematic of a hydrogel network in which at least one interface between contacting hydrogel objects comprises a bilayer and at least one interface does not comprise a bilayer. At an interface where there is no bilayer, a new bilayer can be created by pulling the hydrogel objects at the interface apart, and bringing them back together.

FIG. 1f illustrates the use of αHL pores in a bilayer to carry an ionic current between two hydrogel shapes separated by an interface bilayer.

FIG. 1g provides an example of a mechanical device, a hydrogel rotor.

FIGS. 2a and 2b show a PMMA mold made with a CNC machine that was used as a template to make agarose shapes.

FIG. 2c shows shapes that were immediately immersed in a lipid/hexadecane mixture upon removal from the template. Scale bars in FIG. 2 represent 3 mm.

FIGS. 3a-d relate to bilayer formation caused by two lipid-coated objects being brought together. To prove that a hydrogel shape was completely covered with a lipid monolayer, a lipid-coated agarose sphere (~1 mm) was used to touch the shape at arbitrary positions (FIGS. 3c-d). Bilayer formation was observed each time. An increase in capacitance was observed when two lipid-coated objects were brought together, confirming the formation of a bilayer (see FIG. 4). Scale bars in FIGS. 3a-d represent 1 mm.

FIG. 3e demonstrates how a bilayer may be used. The presence of the bilayer permitted the insertion of αHL pores. Heptameric WT-αHL (~0.2 µL, 1.1 µg mL$^{-1}$) diluted in DPhPC liposomes (1 mg mL$^{-1}$) in 1 M KCl, 10 mM Tris•HCl, pH 7.0, was absorbed by an agarose sphere connected to the ground electrode (denoted cis). The currents carried by a single αHL pore upon increasing the potential applied to the trans electrode (+20, +50, +75 and +100 mV) were 17.5 pA, 50.3 pA, 78.5 pA and 108 pA, respectively, in agreement with reported values.

FIG. 3f demonstrates the integrity of αHL pores inserted into bilayers. Here the inclusion of γCD (50 µM) in one of the agarose spheres (trans) elicited binding events with the αHL mutant 2N (cis) with ~64% block of the amplitude of the open pore current (n=562 events, from two independent experiments). The residence time of γCD was 146±4 ms at +20 mV. The signal was low-pass filtered at 1 kHz and sampled at 10 kHz.

In FIG. 4a, the stability of the bilayer (1 mg mL$^{-1}$ DPhPC in hexadecane) formed between an agarose cube (2% w/v in 1 M KCl, 10 mM Tris•HCl, pH 7.0) and an agarose sphere (3% w/v) was determined by monitoring the bilayer capacitance over time. The bilayer was stable for at least 2 h (the recording was stopped after 2 h) under an applied potential (increased from +75 mV to +150 mV). Expanded regions of the capacitance recordings show that a tight bilayer seal was obtained under an applied potential (+75, +100, +150 mV).

FIGS. 4b-e provide examples of hydrogel-hydrogel bilayers formed at the interface between various hydrogel shapes. The bilayers in all cases were stable for at least 1 h at an applied potential of up to +100 mV. The bilayer area could be changed under an applied potential without rupturing or causing a leak in the bilayer. Values denoted by arrows indicate applied potential in mV. Scale bars in FIGS. 4b-e represent 1 mm.

FIG. 5a is a schematic diagram showing bilayer formation between two hydrogel shapes, and the effect of force on bilayer stability. The bilayer area increased or decreased depending on whether the shapes were pushed against each other or pulled apart. The bold arrows indicate the movement of the agarose shapes connected to Ag/AgCl electrodes, which was caused by adjustments of the micromanipulators in the directions indicated (thin arrows). The shades of the bold and thin arrows correspond. Dark and light ladders on the shapes denote lipid monolayer leaflets.

FIGS. 5b-i demonstrate that agarose shapes in a DPhPC/hexadecane mixture (5 mg mL-1) could be arranged in various configurations to form lipid bilayers of the desired size.

FIGS. 5j-l show that the hydrogel-hydrogel bilayers formed were stable up to an applied potential of +150 mV, as monitored by capacitance measurements. The bilayer size was manipulable under an applied transmembrane potential by moving the hydrogel shapes with a micromanipulator. Scale bars in FIGS. 5b-i represent 1 mm.

FIG. 6a shows agarose shapes (1% w/v) containing fluorescein and 5-carboxytetramethylrhodamine (5% v/v) (5-cTAMRA) that were incubated in DPhPC in hexadecane (10 mg mL$^{-1}$) and manipulated into chains using a steel needle. The absence of dye transfer across the hydrogel interfaces (labeled 1-6) revealed the presence of bilayers.

FIG. 6b shows a network in which a bilayer was compromised. In this network dye diffusion from one hydrogel object to the other was discernible in ≤1 min (n=11).

FIG. 6c shows agarose cubes arranged in a pattern with bilayers at the interfaces.

FIG. 6d shows two different shapes (crescent and cross). These were arranged to form a pattern with each crescent forming a bilayer with the cross, as depicted in FIG. 6e. The scale bars in FIGS. 6a-e represent 1 mm.

FIG. 7a shows lipid-coated hydrogel shapes self-assembled when agitated in hexadecane (≤5 mg mL$^{-1}$ DPhPC; at a higher lipid concentration of 10 mg mL$^{-1}$ self assembly was slower owing to the increased viscosity of the oil). No bilayers were present at the interfaces between hydrogel objects in these self-assembled networks as determined by electrical measurements.

FIGS. 7b-c show that the assemblies could be rearranged manually with a steel needle (see FIG. 8), and were by this means used to form switchable electrical networks. As shown here, two agarose spheres (diameter 700 µm) were formed on a two-armed Ag/AgCl electrode connected to the ground end of the head stage. An assembly of agarose pentagons was penetrated by another Ag/AgCl electrode connected to the active end of the head stage. Sliding a pentagon (white arrow) with a needle changed the network from a compact to an extended configuration, and rewired the network from one grounded sphere to the other.

FIG. 7d-e shows that the configuration of a hydrogel network, with shapes containing different small molecules (5-cTAMRA and fluorescein), was manipulated with a needle. It was not necessary to remove any of the hydrogel objects from the oil; the shapes slid along each other to reach the final configuration. Scale bars in FIGS. 7b-e represent 2 mm.

FIGS. 8a-f show hydrogel shapes that were manipulated with a steel needle to form directed assemblies. These assemblies were stable but could be disassembled at a specific location within the network by applying a force using the needle (FIG. 8h), and reassembled by bringing two hydrogel shapes together again (FIG. 8i). The shapes were assembled in hexadecane containing DPhPC (≤5 mg mL$^{-1}$). Dye diffusion across the hydrogel interfaces was seen indicating the absence of bilayers (FIGS. 8d-i). The scale bars in FIGS. 8a-i represent 2 mm.

In FIG. 9a a bilayer was formed between an agarose hexagon (top of the figure) and a 4-hexagon network (the remaining hexagons) in a lipid/hexadecane mixture (5 mg mL–1 DPhPC). The interfaces between hexagons in the 4-hexagon network did not comprise bilayers. The scale bars in FIG. 9a represent 2 mm.

FIG. 9b shows the increase in capacitance upon bilayer formation at +20 and +50 mV.

FIG. 9c demonstrates that the ease of rupturing a bilayer by pushing two hydrogels against each other, and reforming the bilayer by moving the two pieces apart slowly using a micromanipulator, offers an easy way to change the electrical contacts in a hydrogel network by breaking a bilayer at one location and forming one at another. The dashed lines denote the boundaries of the hexagons (i.e. between the agarose hexagon and the 4-hexagon network) forming bilayers, and the dashed black lines denote the boundaries where no bilayers are formed (between hexagons in the 4-hexagon network). False shading was added to the shapes, using Adobe Photoshop, to increase clarity.

FIG. 10a shows the ends of a flexible wire being used to contact a pentagon at two points. Bilayer formation between the hydrogel wire and the pentagon was monitored by an increase in capacitance. FIG. 10b shows that the bilayer was stable for at least 12 h (after which the recording was stopped). A capacitance drift of 800 pF (1300 pF to 500 pF) was observed over 12 h. False shading was added to the shapes, using Adobe Photoshop, to increase clarity.

FIG. 10c relates to the use of an agarose wire to connect various shapes. A bilayer may or may not be present (determined by measuring the capacitance) between a shape and the wire depending on the lipid concentration and how hard the shape is pushed against the wire. The hydrogel wire was used as a flexible connector between two hydrogel objects. FIG. 10d shows the reconfiguration of an electrical connection by the movement of hydrogel objects between electrodes. The scale bars in FIGS. 10a-c represent 2 mm.

FIG. 12a is a schematic illustration of FIGS. 12b-f. The letters (c, d, e, f) on the capacitance traces (shown in g-i) correspond to the respective figure panels. False shading was added to the shapes, using Adobe Photoshop, to increase clarity. The scale bars represent 2 mm.

FIG. 12b shows two hydrogel shapes, a pentagon and a hexagon, electrically connected with an agarose wire. A bilayer was formed between an agarose sphere at an Ag/AgCl electrode (ground end, cis) and the pentagon shape, and a second electrode was inserted into the hexagon shape (active end, trans).

FIG. 12c shows the agarose wire broken into two. One piece of the wire was dragged on the surface to-and-fro from the end of the other wire. Although the two broken agarose wires were no longer in contact, the electrical connection was maintained as denoted by a specific capacitance of ~0.4 μm cm$^{-2}$ (as shown in FIG. 12g).

FIG. 12d relates to an experiment in which an agarose wire was connected between two pentagons. A bilayer was formed between an agarose sphere (ground end, cis) and a pentagon. The trans pentagon (active end) was dragged to-and-from the wire and finally placed at a distance. An electrical connection was still observed as determined from the specific capacitance (~0.7 μm cm–2) (as shown in FIG. 12h).

To determine whether the agarose shape had painted a thin aqueous or hydrogel layer on the surface when dragged, the trans electrode was removed from the pentagon and touched on the surface where the shape had been dragged. This is shown in FIG. 12e. As shown in FIG. 12h bilayer capacitance was still observed. Expanded regions of the capacitance recordings show that a tight bilayer seal was obtained.

FIG. 12f relates to the capacitance upon touching the trans electrode to a part of the surface that had not been exposed to the agarose. The capacitance decreased to the level observed in the absence of a bilayer (as shown in FIG. 12i).

FIGS. 13a-f show an increase in the complexity of hydrogel network from two to four shapes, and shapes interconnected with a hydrogel wire. αHL insertion was observed in every case. All data were collected at an applied potential of +20 mV, at a sampling rate of 10 or 20 kHz, and the traces were filtered at a low pass frequency of 1 kHz. The bold yellow arc at a shape-shape interface denotes a bilayer. There were no bilayers present elsewhere in an assembly.

Figure 13:
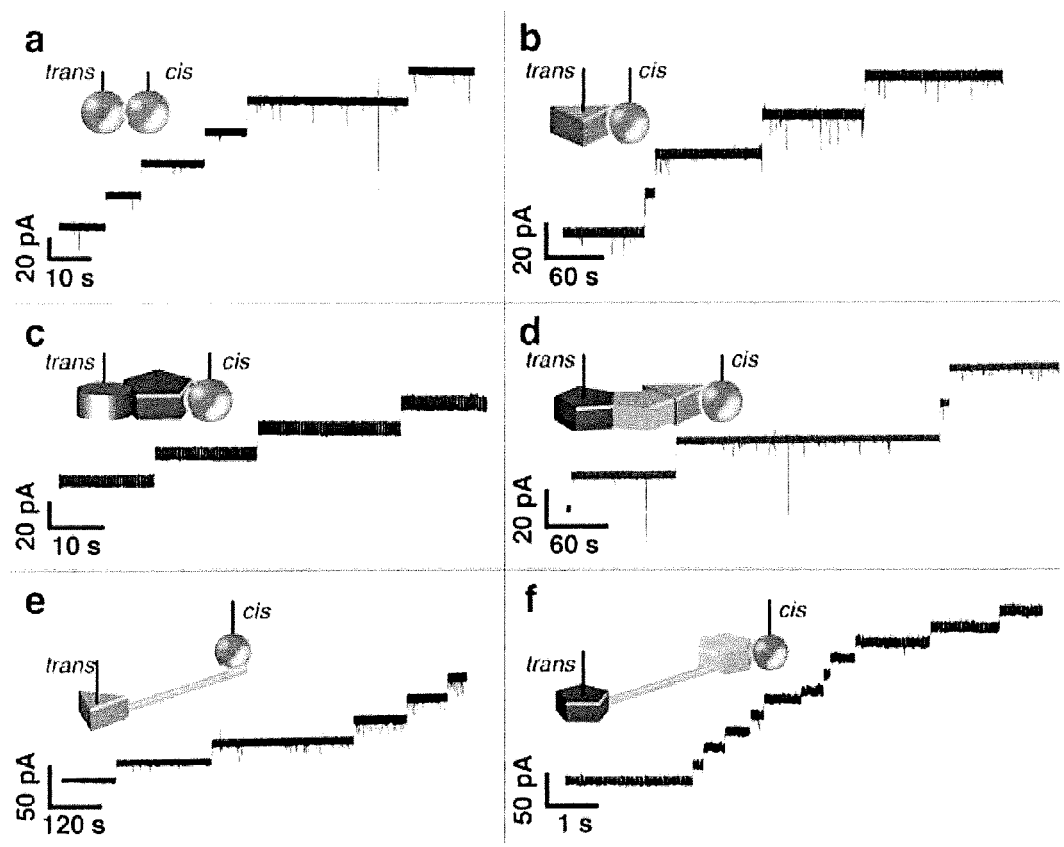
FIG. 13 relates to the insertion of αHL into bilayers formed at the interface between hydrogel objects in different arrangements.

In the network shown in FIG. 13a the hydrogel network comprises two hydrogel spheres. αHL heptamer (1.1 μg mL$^{-1}$) was adsorbed onto an agarose sphere and data were recorded in a lipid/hexadecane mixture (1 mg mL$^{-1}$ DPhPC). The mean current step for αHL heptamer insertion was 25.6±0.6 pA (average±S.D., n=8). The cis electrode was connected to the ground end of the headstage, and the trans electrode to the active end.

FIG. 13b shows a network comprising a hydrogel sphere and a prism-shaped hydrogel body. αHL (0.28 μg mL$^{-1}$) was adsorbed onto the agarose sphere in a lipid/hexadecane mixture (5 mg mL$^{-1}$). The mean current step for αHL heptamer insertion was 20.6±0.3 pA (n=4).

FIG. 13c shows a hydrogel network comprising three differently shaped hydrogel bodies. αHL heptamer (5.6 ng mL$^{-1}$) was adsorbed onto the agarose sphere in a lipid/hexadecane mixture (5 mg mL$^{-1}$ DPhPC). The mean current step for αHL heptamer insertion was 17.8±0.8 (n=3). The increased noise in this case is owing to the formation of a large bilayer (>600 pF).

The network shown in FIG. 13d comprises four differently shaped hydrogel bodies. The network was formed in a lipid/hexadecane mixture (5 mg mL$^{-1}$ DPhPC). αHL heptamer (560 ng mL$^{-1}$) was adsorbed onto the agarose sphere. The mean current step for αHL heptamer insertion was 19.4±0.7 pA (n=4).

FIG. 13e shows a hydrogel network comprising a hydrogel wire, a hydrogel sphere at one end of the hydrogel wire and a prism-shaped hydrogel body at the other end of the hydrogel wire. αHL heptamer (560 ng mL$^{-1}$) was adsorbed onto the agarose sphere in a lipid/hexadecane mixture (5 mg mL$^{-1}$ DPhPC). The mean current step for αHL heptamer insertion was 26.4±1.7 (n=8).

FIG. 13f shows a hydrogel network comprising a hydrogel wire. At one end of the wire there is a hydrogel body with a pentagon-shaped face. At the other end of the wire there is a hydrogel body with a hexagon-shaped face, which is in contact with a hydrogel sphere. The network was assembled in a lipid/hexadecane mixture (1 mg mL$^{-1}$ DPhPC). The αHL 2N mutant (IVTT protein, diluted 25-fold) was adsorbed onto the sphere. The mean current step for αHL heptamer insertion was 25.4±1.3 pA (n=17) measured.

Figure 14:
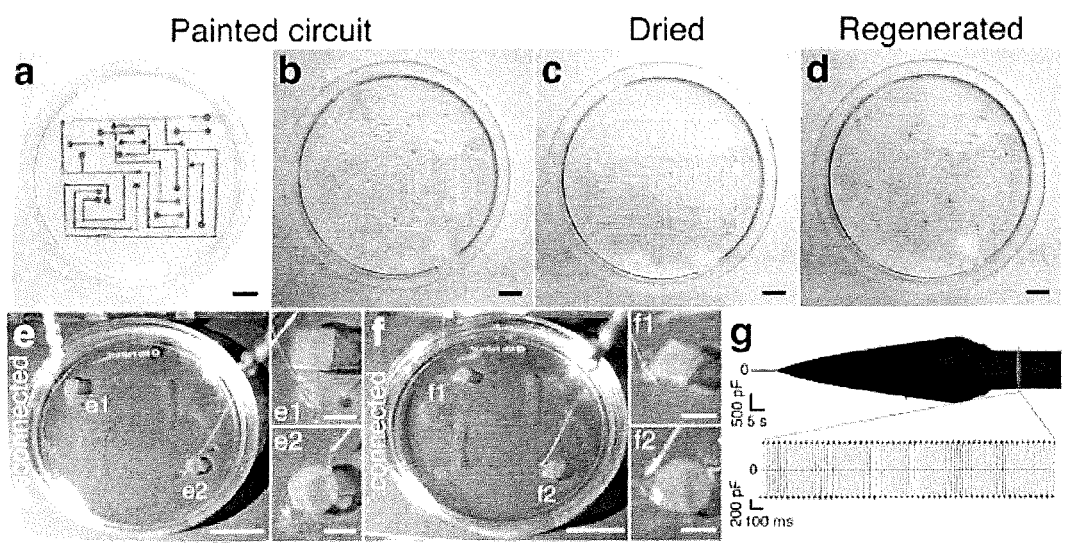

FIG. 14 relates to painted circuits. FIGS. 14a-b show agarose wires (1% w/v) that were painted on a circuit diagram on a Petri plate using a 21-gauge syringe needle (the diagram was then removed).

FIG. 14c shows the agarose circuit once dried and FIG. 14d shows the agarose circuit regenerated by adding buffer (1 M KCl, 10 mM Tris•HCl, pH 7.0, containing 5% v/v 5-cTAMRA). The buffer rehydrated only the dried agarose wires (pink) and did not wet the Petri plate surface.

FIG. 14e shows a simple circuit painted with agarose wires and immersed in hexadecane (1 mg mL$^{-1}$ DPhPC). Two hydrogel objects (cube and cylinder) were placed at distant points on the circuit. Two agarose spheres (diameter 800 μm) at the end of Ag/AgCl electrodes were placed in the lipid/oil mixture (insets e1 and e2).

Figure 1:
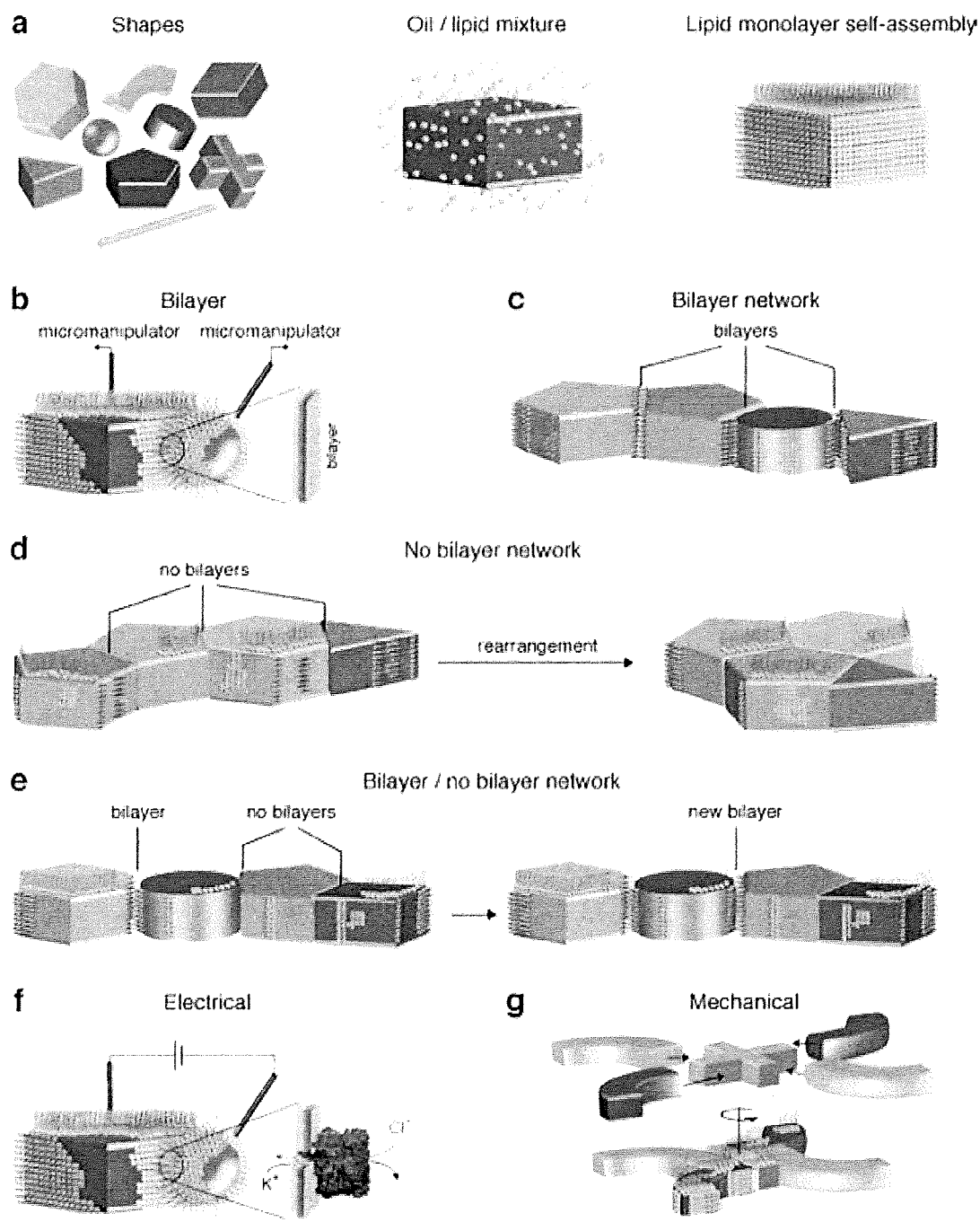
FIG. 1*a-g* contain schematic illustrations hydrogel shapes, hydrogel objects and hydrogel networks.

In the circuit in FIG. 14f one sphere was pressed hard against the cube such that no bilayer was formed between the two objects (inset f1, the diffusion of dye into the sphere indicates that no bilayer was formed), while a bilayer was formed between the second agarose sphere and the cylinder (inset f2, no colour change of this sphere demonstrates the formation of a lipid bilayer barrier). Bilayer formation was further confirmed by a specific capacitance measurement of 0.65 μF cm$^{-2}$ (shown in FIG. 14g). The diffusion of dye from the hydrogel cube and cylinder into the wires was observed after a few minutes indicating that there were no bilayers at these junctions. The scale bars in FIGS. 14a-f represent 1 cm and the scale bars in FIGS. 14e1, e2, f1, f2 represent 2 mm.

Figure 15:
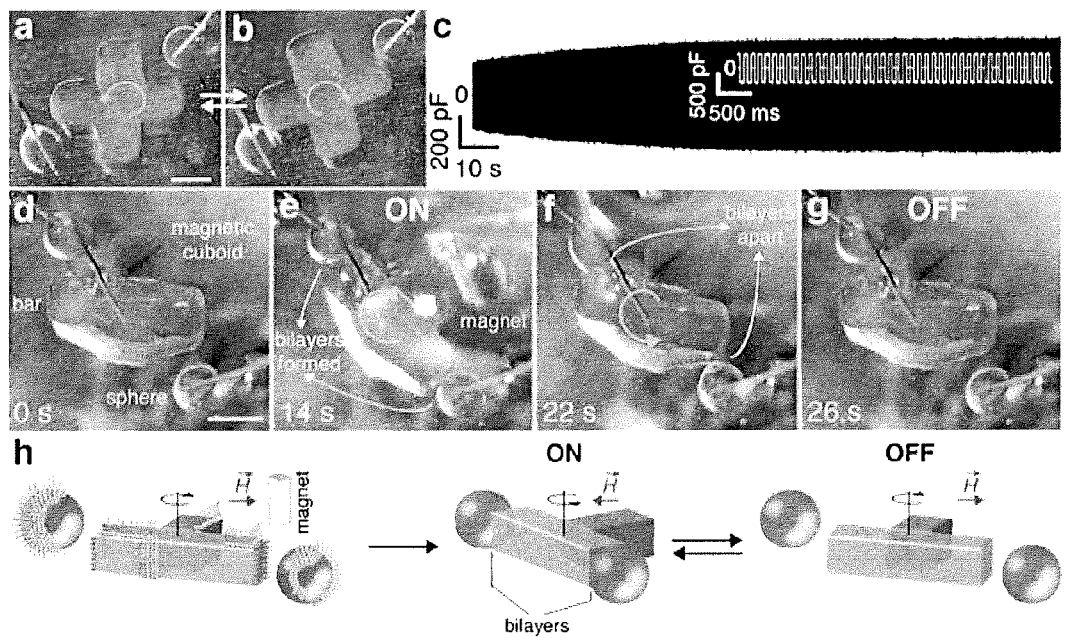

FIG. 15 relates to soft-matter mechanical devices. FIGS. 15a-b show an agarose cross (coloured with 5-cTAMRA) that was used as a switch to connect and disconnect two agarose spheres (diameter 1 mm) on Ag/AgCl electrodes, one sphere was connected to the ground and the other to the active end of a head stage. An electrical circuit was formed when the two poles of the cross formed bilayers with the spheres (1 mg mL$^{-1}$ DPhPC in hexadecane). In this case, the rotation of the hydrogel switch was performed manually using a steel needle. FIG. 15c shows the representative trace showing the capacitance increase during bilayer formation.

FIGS. 15d-g demonstrate the automation of the 'ONOFF' function of the hydrogel switch by using a magnetic field. The switch was made by connecting a hydrogel cube loaded with paramagnetic beads and an empty hydrogel bar. Having the magnetic beads in only one hydrogel piece increased the spatial resolution with which the switch could be controlled. The switch was immersed in a lipid/oil mixture (1 mg mL$^{-1}$ DPhPC in 1:1 v/v hexadecane/silicone oil AR20). A wire was inserted in the empty hydrogel bar to act as an axle. A cylindrical Nd magnet (height 5 mm, radius 2.5 mm) was used to rotate the switch clockwise so that the poles of the hydrogel bar formed bilayers ('ON' state) with the hydrogel spheres. A counter-clockwise rotation of the switch separated the leaflets disconnecting the circuit ('OFF' state). The arcs with arrowheads denote the clockwise and counter-clockwise rotation of the switch. The time in seconds is shown. The 'ON-OFF' cycle was repeated several times.

FIG. 15h show reversible bilayer formation using the switch. The scale bars in FIGS. 15a and 15d represent 1 mm.

Figure 16:
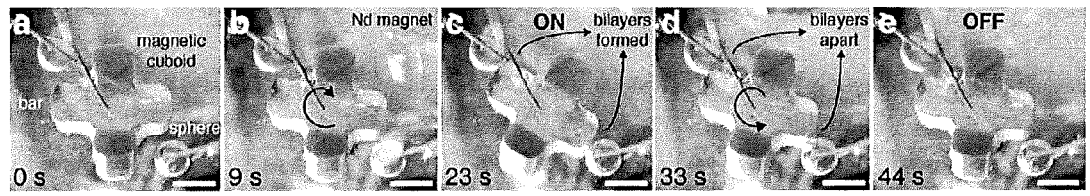

FIG. 16 relates to a hydrogel switch controlled by a magnetic field. FIG. 16a shows a hydrogel switch assembled in the shape of a cross using three agarose pieces—two cubes containing paramagnetic beads and a rectangular bar without any magnetic beads. The switch was immersed in a lipid/oil mixture (1 mg mL$^{-1}$ DPhPC in 1:1 v/v hexadecane/silicone oil AR20 mixture). An Ag/AgCl electrode (not connected to the headstage) was inserted in the hydrogel switch.

FIGS. 16b-c show how a 5 mm×2.5 mm (h×r) cylindrical Nd magnet was used to rotate the switch clockwise such that the poles of the empty hydrogel bar formed bilayers (ON state) with the hydrogel spheres (diameter ~900 μm) on two Ag/AgCl electrodes (cis and trans).

FIGS. 16d-e show that the bilayer leaflets were separated by rotating the switch in the counter-clockwise direction (OFF state). The time in seconds is shown. The scale bar in FIG. 16a-e represents 1 mm.

Figure 17:
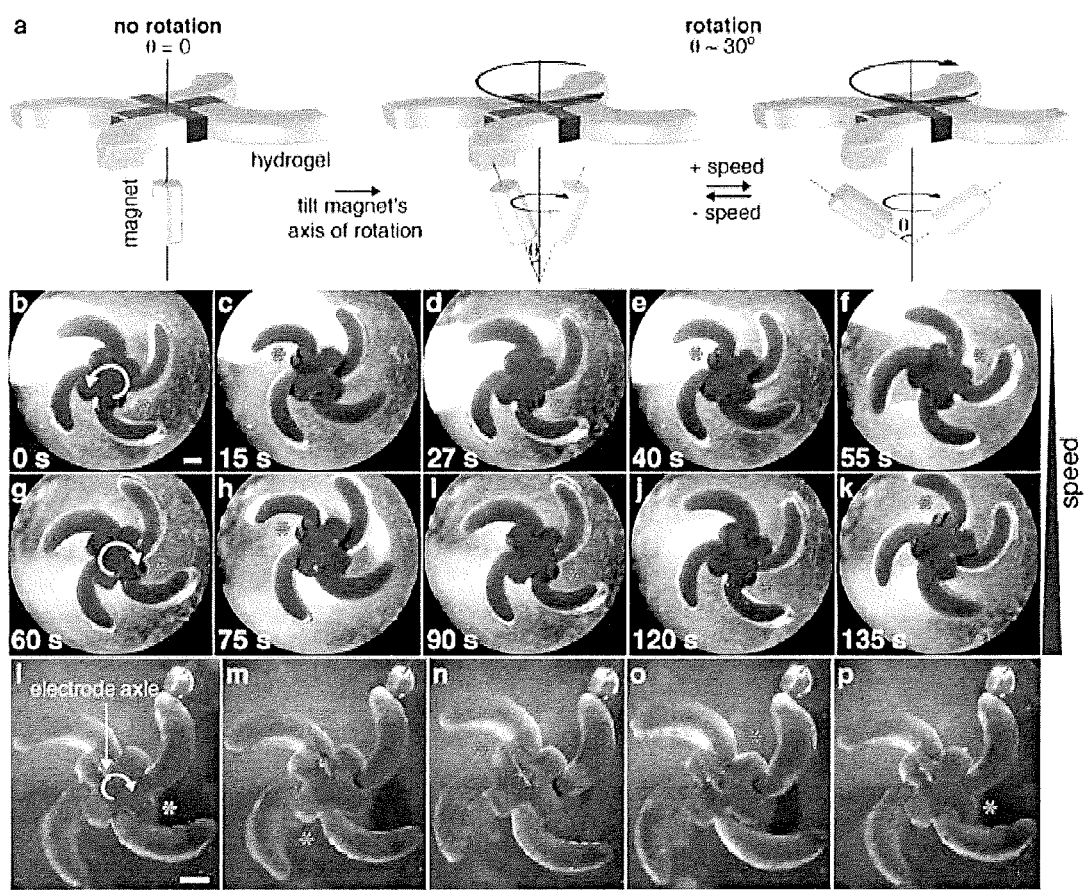

FIG. 17 shows reversible rotation of a hydrogel network comprising a rotor. A hydrogel cross and four crescents were used to construct a rotor.

FIG. 17a show a rotor, loaded with paramagnetic beads, rotated under an external magnetic field. The rotation depended on the magnet's axis of rotation: when θ=0, the assembly did not rotate; when θ~30°, the assembly rotated. The direction of rotation of the hydrogel assembly changed with the magnet's angular velocity. At lower speeds the assembly rotated counter to the rotation of the magnet, but at higher speeds the assembly switched its direction of rotation to match that of the magnet.

FIGS. 7b-k show movie snapshots of the rotor's counter clockwise and clockwise rotation at slow and fast speeds of the magnet, respectively. The time in seconds is shown.

FIGS. 17l-p show four crescents and a cross (both shapes contained magnetic beads) that were assembled manually to form a rotor, which was rotated manually around an Ag/AgCl axle. The axle also acted as an electrode. Both mechanical assemblies were coated with a lipid monolayer in a lipid/hexadecane mixture (1 mg mL$^{-1}$ DPhPC). The blades of the rotor connected sequentially with a sphere on an Ag/AgCl electrode as shown by the formation of a bilayer with specific capacitance ~0.6 μF cm$^{-2}$. The asterisk denotes a defect in the cross shape used as a reference point to follow the rotation. In FIGS. 17b and 17l the scale bars represent 1 mm.

Figure 18:
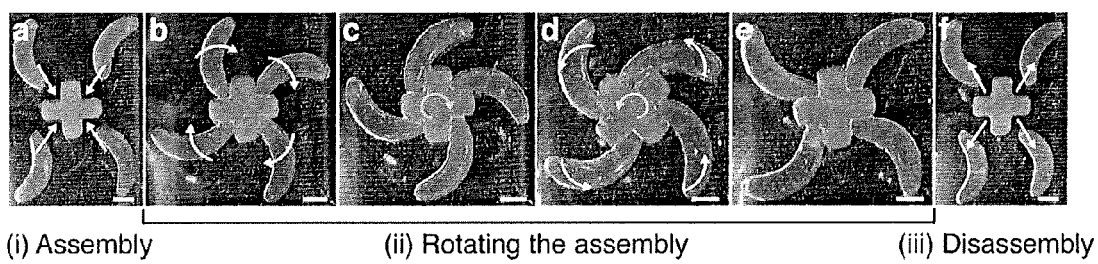

FIG. 18 relates to the assembly and disassembly of a hydrogel network comprising a rotor. FIG. 18a shows five hydrogel bodies. The cross-shaped hydrogel body is coloured with 5-cTAMRA and the four crescent-shaped hydrogel bodies were coloured with fluorescein. The shapes were assembled to form a rotor in hexadecane.

FIGS. 18b-e show a hydrogel network comprising a rotor that could be rotated manually or by applying an external magnetic field (see FIG. 17). The white arcs with arrowheads denote the closing (FIGS. 18b to 18c) and opening (FIGS. 18d to 18e) of the crescents to get a compressed or an expanded rotor, respectively. The arcs with arrowheads denote the clockwise and counter-clockwise rotation of the whole assembly.

FIG. 18f shows that the assembly could be disassembled by manually pulling the blades of the rotor apart using a steel needle. The diffusion of 5-cTAMRA from the cross to the crescent shapes can be seen clearly. The scale bars in FIGS. 18a-f represent 1 mm.

Figure 19:
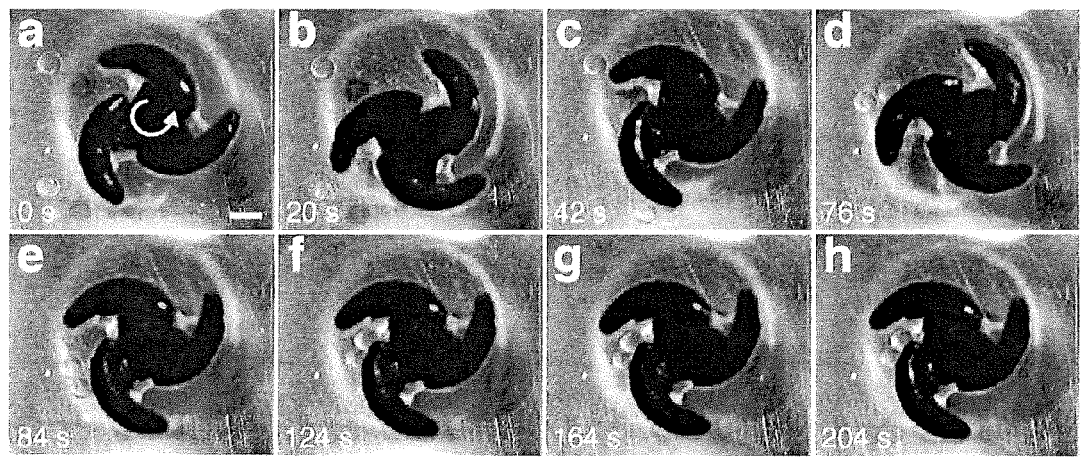

FIG. 19 relates to a hydrogel network comprising a rotor as a droplet-collecting device. FIG. 19a shows a hydrogel rotor assembled using three crescents and a triangle in a lipid/hexadecane mixture (1 mg mL$^{-1}$ DPhPC). Two aqueous droplets (1 mg mL−1 DPhPC liposomes in 1 M KCl, 10 mM Tris•HCl, pH 7.0) were pipetted in the oil. The rotor was rotated in the counterclockwise direction using a rotating Nd magnet. The scale bar in FIG. 19a represents 1 mm.

FIGS. 19b-h show the rotation of the rotor generated enough centripetal force that the droplets travelled towards the rotor and stuck to its arms by forming a bilayer with the hydrogel. False shading was added to the shapes, using Adobe Photoshop, to increase clarity. The time in seconds is shown.

Figure 20:
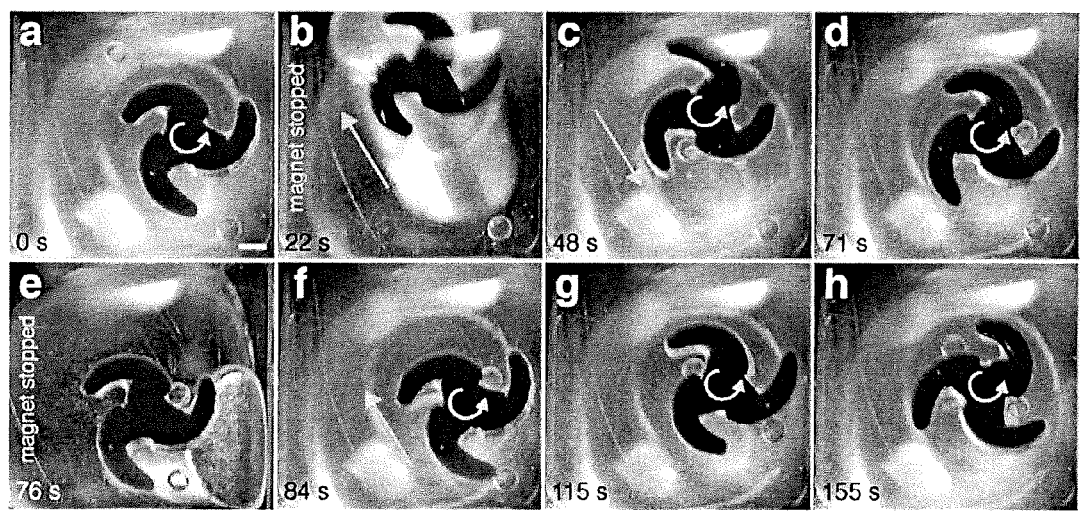

FIG. 20 relates to a hydrogel network comprising a rotor as a droplet-picking device. FIG. 20a shows a hydrogel network comprising a rotor similar to that described in FIG. 19. The rotor was made and immersed in a lipid/hexadecane mixture (1 mg mL$^{-1}$ DPhPC). Two aqueous droplets (1 mg mL$^{-1}$ DPhPC liposomes in 1 M KCl, 10 mM Tris•HCl, pH 7.0) were pipetted in the oil. The rotor was rotated in the counter-clockwise direction using a rotating Nd magnet. The scale bar in FIG. 20a represents 1 mm.

In the experiment shown in FIG. 20b the magnet was stopped at the location of the droplet towards the top of the figure such that a bilayer was formed between the droplet and one of the blades of the rotor.

FIGS. 20c-d show the magnet's rotation started again such that the rotor carried the droplet to the centre while rotating in the same direction as before.

FIGS. 20e-h shows the magnet's rotation stopped again at the droplet towards the bottom of the figure to form a bilayer with the rotor's arm. The magnet's rotation started again and the droplets carried back to the centre with the rotating unit. The lines with arrowheads denote the point at which the magnet was stopped and the location where the rotor was carried. The arcs with arrowheads denote the rotor's direction of rotation. False shading was added to the shapes, using Adobe Photoshop, to increase clarity. The time in seconds is shown.

DETAILED DESCRIPTION OF THE INVENTION

The present invention relates to a hydrogel network comprising a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects.

The hydrogel network of the invention comprises two or more of said hydrogel objects. Typically, the hydrogel network comprises three or more of said hydrogel objects. For instance, the hydrogel network may comprise four or more of said hydrogel objects.

The hydrogel network may be a two-dimensional or a three-dimensional network. Typically, it is a three-dimensional network.

The hydrogel body comprises a mass of hydrogel and may be any shape. Accordingly, the hydrogel body may be any regular or irregular shape, or any polygon. When the hydrogel body is a polygon, it may be convex or non-convex.

Usually the hydrogel body is a three-dimensional shape. It may thus be any three-dimensional shape. As the skilled person will appreciate, a three-dimensional shape may have three dimensions that are all the same order of magnitude, it may have one dimension that is at least an order of magnitude larger or smaller than the other two dimensions, or all three dimensions of the shape may be of different orders of magnitude.

The hydrogel shape may, for instance, be spherical or a shape comprising two or more sides. In some embodiments, the hydrogel shape comprises from 1 to 50 sides, for instance from 1 to 15 sides. The hydrogel shape may, for example, be a 2-sided shape such as a hemisphere; a 3-sided shape such as a cylinder, a bended cylinder, or a 3-sided wire; a 5-sided shape such as a triangular prism; a 6-sided shape such as a cuboid; or a 14-sided shape such as a cross-shape.

Typically, the hydrogel body is spherical, cross-shaped, cuboid, crescent-shaped, prism-shaped, cylindrical, wire-shaped or a shape which has a triangular, pentagonal, hexagonal, heptagonal, octagonal, nonagonal, decagonal, undecagonal, dodecagonal, square or rectangular face.

It follows that the hydrogel object may also be any shape.

Individual hydrogel bodies in the hydrogel network may be any shape. It thus follows that different hydrogel objects in a hydrogel network of the invention may be all the same shape or the hydrogel network may comprise hydrogel objects that are a variety of different shapes. When the hydrogel network comprises different-shaped hydrogel objects, the hydrogel objects need not necessarily all have different shapes. Thus, for instance, in a network comprising five hydrogel objects one of the hydrogel objects may be cross-shaped and four of the hydrogel objects may be crescent shaped.

The hydrogel body may, in some embodiments, comprise other materials, compounds or substances. For instance, the hydrogel body may contain at least one small molecule, such as a dye, or a magnet. Suitable dyes include, but are not limited to, fluorescein and 5-cTAMRA (5-carboxytetramethylrhodamine). Alternatively, the hydrogel body may contain at least one sensor molecule, for instance a sensor molecule that it sensitive to a particular chemical or is a light-sensitive molecule.

In some embodiments, the hydrogel network comprises a therapeutic agent, such as a prodrug, or a diagnostic agent, such as a contrast agent. For instance, a therapeutic agent or diagnostic agent may be present in the hydrogel body.

The hydrogel of the hydrogel body may comprise any suitable hydrogel. The hydrogel typically comprises a high weight percent of water.

Usually, the hydrogel comprises agarose. Typically, the hydrogel comprises agarose and water. The concentration of the agarose in water is typically less than or equal to 10% w/v agarose. For instance, the concentration of the agarose in said water may be from 0.25 to 5% w/v agarose. More typically, the concentration of the agarose in said water is from 0.5 to 4% w/v, for instance, from about 1% w/v to 3% w/v. Usually, the concentration of the agarose in said water is about 1% w/v or 3% w/v.

Hydrogels other than agarose may also be used. For instance the hydrogel body may comprise methylcellulose, polyethylene glycol diacrylate, polyacrylamide, matrigel, hyaluronan, polyethylene oxide, polyAMPS (poly(-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the hydrogel body may comprise a silicone hydrogel or LB (Luria broth) agar.

When a hydrophilic material is placed in a medium comprising amphipathic molecules, the hydrophilic component of the amphipathic molecules will be attracted to the hydrophilic material. Thus a layer of amphipathic molecules will form on at least part of the surface of the hydrophilic material. Typically, the medium is a hydrophobic medium. When the concentration of amphipathic molecules in the medium is high enough, the layer will usually be a monolayer that covers the entire surface of the hydrophilic material. The concentration of amphipathic molecules required to form a monolayer will depend on factors such as the surface area of the hydrophilic material and whether or not there are other hydrophilic materials in the same medium. There may be other factors that influence whether a monolayer of amphipathic molecules is formed. For instance, if the hydrophilic material has a particularly intricate shape, it may only be possible for a layer to form on part of the surface of the hydrophilic material.

In the present invention, the individual hydrogel bodies comprise a hydrophilic material. As discussed below, the hydrogel network is usually disposed in a hydrophobic medium and this hydrophobic medium typically comprises amphipathic molecules. Amphipathic molecules in the bulk hydrophobic phase form an outer layer of amphipathic molecules on at least part of the surface of the hydrogel body.

In some embodiments, the at least one hydrogel body comprises a hydrophilic material and a hydrophobic material. The hydrophilic material is typically agarose. The hydrogel body comprising a hydrophilic material and a hydrophobic material may, for example, be a spherical hydrogel body made up of a hemisphere of a hydrophilic material and a hemisphere of a hydrophobic material, and may therefore be considered to have two faces. A hydrogel object comprising a hydrogel body comprising a hydrophilic material and a hydrophobic material has therefore been termed a "Janus particle".

Within the hydrogel network of the invention, each of said hydrogel objects contacts another of said hydrogel objects. The boundary that is shared between contacting hydrogel objects, at the point of contact between the objects, is referred to herein as an interface. Thus, each said hydrogel object in the network contacts another of said hydrogel objects to form an interface between that hydrogel object and the other hydrogel object. An interface is thus formed when part of the outer layer of one hydrogel object contacts part of the outer layer of another hydrogel object.

Figure 10:
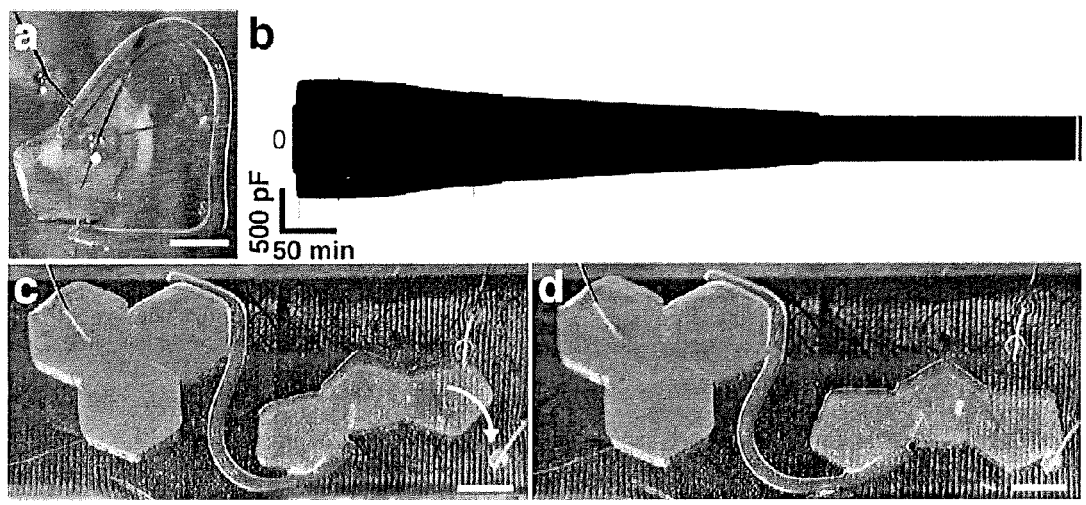
FIG. 10 relates to hydrogel networks comprising a hydrogel wire. Agarose could be made into wires by using a glass capillary.

As the skilled person will appreciate, two hydrogel objects may share a single interface, or two or more interfaces. For instance, if the hydrogel network comprises a hydrogel wire, the hydrogel wire may be in contact with another hydrogel object at two points to form two separate interfaces (as shown in FIG. 10a). Similarly, if the hydrogel network comprises a crescent-shaped hydrogel object the crescent-shape may be in contact with another hydrogel object at two points to form two separate interfaces (as shown in FIG. 5c). Complementary regions of two hydrogel objects may, for instance, fit together in a lock-and-key arrangement with more than one interface forming between the two hydrogel objects. For instance, two cross-shaped hydrogel objects may fit together in a lock-and-key arrangement (as shown in FIG. 5e).

Typically, a hydrogel object not in contact with another hydrogel object will comprise a complete monolayer of amphipathic molecules. When two hydrogel objects comprising a monolayer of amphipathic molecules are brought together, a bilayer of amphipathic molecules will quickly form at the interface between the two hydrogel objects. The bilayer forms as it is an energetically more favourable configuration for the amphipathic molecules to adopt. The shape of the bilayer formed will be the shape with the lowest free surface energy. As discussed below, the size of the bilayer can be adjusted by pushing the hydrogel objects together or pulling the hydrogel objects apart. Further, the bilayer can be removed, for example, by pushing the hydrogel objects together and effectively squeezing out the bilayer.

Thus a bilayer may be formed when two hydrogel objects come together. The hydrogel objects may, for instance, be brought together using a micromanipulator. Each hydrogel object comprises an outer layer of amphipathic molecules, on at least part of the surface of the hydrogel body. Providing that the concentration of amphipathic molecules is high enough, when the two hydrogel objects come together, the amphipathic molecules at the interface spontaneously form a bilayer. The present inventors have found that the presence or absence of a bilayer between any two hydrogel objects may be controlled, for example, by pushing two hydrogel objects together or pulling them apart and/or by increasing or decreasing the concentration of amphipathic molecules surrounding the hydrogel bodies. Likewise, the area of the bilayer can be controlled, for example, by pushing two hydrogel objects together or pulling them apart and/or by increasing or decreasing the concentration of amphipathic molecules surrounding the hydrogel bodies. Typically, the plurality of hydrogel objects is disposed in a hydrophobic medium and thus the concentration of amphipathic molecules will typically be the concentration of amphipathic molecules in the hydrophobic medium.

When the hydrogel network comprises a Janus particle, only the amphipathic molecules in contact with the hydrophilic material of the Janus particle are able to form a bilayer of amphipathic molecules with a neighbouring hydrogel object. This is because of the orientation of the amphipathic molecules around the surface of the hydrogel body of the Janus particle. The amphipathic molecules attracted to the hydrophilic material of the Janus particle will be orientated with their head groups nearest the hydrophilic surface. The amphipathic molecules attracted to the hydrophobic material of the Janus particle will be orientated with their head groups away from the hydrophilic surface. Thus, the amphipathic molecules attracted to the hydrophobic material of the Janus particle are not able to form a bilayer of amphipathic molecules with a neighbouring hydrogel object.

It is possible to detect the formation of a bilayer by measuring the specific capacitance at the interface. A standard voltage protocol may be used.

The hydrogel network may comprise one interface, or it may comprise two or more interfaces. Any of the interfaces in the hydrogel network may comprise a bilayer of amphipathic molecules. The bilayers may be formed as discussed above. Similarly, any of the interfaces in the hydrogel network may not comprise a bilayer of amphipathic molecules. Bilayers will not be formed, for instance, when the two hydrogel objects at the interface are pushed together with enough force to effectively squeeze out the amphipathic molecules at the interface, or when the concentration of amphipathic molecules is too low to form a bilayer. Thus, when the hydrogel network comprises two or more interfaces it is possible, for instance, that: (i) all of the interfaces in the hydrogel network comprise a bilayer of amphipathic molecules; (ii) none of the interfaces in the hydrogel network comprises a bilayer of amphipathic molecules; or (iii) at least one of the interfaces comprises a bilayer of amphipathic molecules and at least one of the interfaces does not comprise a bilayer of amphipathic molecules.

When there is no bilayer of amphipathic molecules at an interface between two hydrogel objects, the two hydrogel objects may, or may not, be in direct contact with each other at the interface. The interface may for instance comprise a layer of a material or a compound other than a bilayer of amphipathic molecules. There may, for instance, be a thin layer of an aqueous medium (e.g. a thin layer of water, or a thin layer of an aqueous solution) between the two hydrogel objects.

Typically, the surface of the hydrogel object at the molecular level is not completely smooth. The agarose polymer chains of an agarose hydrogel object, for instance, usually do not lie flat along the edge of the hydrogel body, but rather create a "fuzzy edge" to the hydrogel body. Thus, when there is no bilayer of amphipathic molecules at an interface between two contacting hydrogel objects, the two hydrogel objects may be in direct contact with each other at the interface, and the agarose polymer chains at the edge of one hydrogel body will interact to a certain extent with the agarose polymer chains at the edge of the adjacent hydrogel body. The chains from different objects may for instance intermingle and become entangled with each other to a certain extent. However, as the skilled person will appreciate, the extent to which such polymer chains become intermingled or entangled with each other and interact at the interface will be significantly less than the degree of chain entanglement, bonding and interaction within the bulk of a hydrogel object. The agarose polymer chains within the bulk of a hydrogel body will form significantly stronger intermolecular interactions with each other, and will be significantly more entangled, than the chains of the two different hydrogel objects at the interface between the objects. The fact that the interactions are stronger in the bulk of a hydrogel object than between two different hydrogel objects contributes to the strengths of the hydrogel objects and helps them to retain their shape. It also explains why two or more different hydrogel objects can be placed adjacent to one another, in direct contact with each other, without merging to form a single object. It also explains why two or more directly-contacting hydrogel objects may be pulled apart again easily, and, if they are pulled apart, why they will generally come apart again at the original interface.

Accordingly, when there is no bilayer of amphipathic molecules at an interface between two hydrogel objects, the two hydrogel objects may be in direct contact with one another at the interface. In some embodiments, the hydrogel objects at the interface may be in direct contact at some points of the interface and not at others. This may occur, for example, when one or both of the hydrogel objects has an uneven surface and/or when there is a thin layer of a aqueous medium between the hydrogel objects at only part of the interface.

The inventors have found that the presence of a bilayer between two hydrogel objects delimits the individual hydrogel objects to a greater extent. This delimitation can be observed, for example, by studying the transport of a dye through the hydrogel network. Usually, no dye will be transported across an interface that comprises a bilayer of amphipathic molecules.

The hydrogel network may further comprise one or more hydrogel objects which do not have an outer layer of amphipathic molecules. For instance it may further comprise a hydrogel object which consists only of a hydrogel body. The further hydrogel object may not be in contact with the plurality of hydrogel objects. The further hydrogel object may be set apart from the plurality of hydrogel objects and thus may be a "stand-alone" hydrogel object. An example of a further hydrogel object set apart from the plurality of hydrogel objects is shown in FIG. 7c. A further hydrogel object, together with the plurality of hydrogel objects may thus, for instance, be used to form a switch or as part of a switch. Alternatively, the further hydrogel object(s) may be in contact with the plurality of hydrogel objects. For instance, the further hydrogel objects may be surrounded by hydrogel objects of the hydrogel network, such that each surface of the further hydrogel object is in contact with a hydrogel object of the hydrogel network and each interface that the further hydrogel object forms with the hydrogel objects of the hydrogel network is an interface that does not comprise a bilayer of amphipathic molecules.

Independently of whether or not an interface comprises a bilayer of the amphipathic molecules, the area of the interface between the contacting hydrogel objects will typically depend upon the shapes of the hydrogel bodies at said interface. Thus, if the interface is formed between the flat faces of two different hydrogel objects, the area will usually be larger than if the interface is formed between a hydrogel object that is a sphere and a flat surface of another hydrogel object.

Typically, in the hydrogel network of the invention, said plurality of hydrogel objects comprises a first hydrogel object and a second hydrogel object, wherein each of the first and second hydrogel objects comprises a hydrogel body, and an outer layer of amphipathic molecules, on at least part of the surface of the hydrogel body, wherein the first hydrogel object contacts the second hydrogel object to form a said interface between the first and second objects. When the hydrogel network comprises three or more hydrogel objects, subject to the condition that the first hydrogel object contacts the second hydrogel object, the first and second hydrogel objects may be anywhere within the hydrogel network.

In some embodiments, the interface between the first and second objects comprises a bilayer of the amphipathic molecules. The bilayer separates the two hydrogel objects such that they are not in direct contact with each other at the interface.

Alternatively, the interface between the first and second objects may not comprise a bilayer of amphipathic molecules. The hydrogel bodies of the first and second objects may, for instance, be in direct contact with each other at the interface between them. Alternatively, the interface may, for instance, comprise a thin layer of a hydrophobic or hydrophilic medium, or another polymer, between the two hydrogel objects.

When the interface between the first and second objects does not comprise a bilayer of amphipathic molecules the first object or the second object may, for instance, be a Janus particle. As discussed above, the amphipathic molecules on the surface of the hydrophobic material of the Janus particle are not able to form a bilayer of amphipathic molecules.

In some embodiments, the hydrogel body of the first hydrogel object is in direct contact with the hydrogel body of the second object, at the interface between the first and second objects.

Usually, in the hydrogel network of the invention, said plurality of hydrogel objects further comprises a third hydrogel object, wherein the third hydrogel object comprises a hydrogel body, and an outer layer of amphipathic molecules, on at least part of the surface of the hydrogel body, wherein the first or second hydrogel object contacts the third hydrogel object to form a said interface between the contacting hydrogel objects, between the first or second hydrogel object and the third hydrogel object.

Typically, the first hydrogel object contacts the third hydrogel object to form a said interface between the first and third hydrogel objects, and wherein the second hydrogel object contacts the third hydrogel object to form a said interface between the second and third hydrogel objects.

Thus, in some embodiments, the network comprises three or more of said hydrogel objects, and a plurality of said interfaces between contacting hydrogel objects.

As mentioned above, the hydrogel network may comprise one interface, or it may comprise two or more interfaces. Typically, the hydrogel network comprises at least n of said hydrogel objects, and at least n−1 of said interfaces between contacting hydrogel objects, wherein n is equal to or greater than 2. The integer n may be equal to or greater than 3. More typically, n is equal to or greater than 4.

The hydrogel network may be a three-dimensional network.

In some embodiments, when the hydrogel network comprises at least n of said hydrogel objects, the network may comprise n or more than n interfaces, wherein n is as herein defined, it being understood that two hydrogel objects may in some embodiments share more than one interface, and that any one hydrogel object can be in contact with (and therefore form an interface with) more than one other hydrogel object.

The integer n can in principle be very high, for instance in the order of millions. This is because the hydrogel bodies may be very small and there is no upper limit on the size of the hydrogel network. Such networks, which can in principle comprise millions of hydrogel bodies, may, for instance, be useful for preparing prototissue (i.e. an aggregate of protocells, also known as minimal tissue). In some embodiments, therefore, the integer n may be as high as several million, for instance up to about 10,000,000, or for instance up to about 5,000,000.

In other embodiments, n may be several hundred, for instance up to about 500, or for instance up to about 400. The integer n may for instance be an integer of from 2 to 500, or an integer of from 3 to 500. n may be an integer of from 2 to 400. In other embodiments, n may be an integer of from 2 to 300, or an integer of from 3 to 200. More typically n is from 2 to 200. In other embodiments, however, n is an integer of from 2 to 50, or an integer of from 3 to 50. n may for instance be from 2 to 20, or from 2 to 10.

In some embodiments, at least one of the interfaces between contacting hydrogel objects comprises a bilayer of amphipathic molecules. Typically, at least two of the interfaces between contacting hydrogel objects comprise a bilayer of amphipathic molecules.

In one embodiment, each of the interfaces between contacting hydrogel objects comprises a bilayer of amphipathic molecules.

Alternatively, in some embodiments, at least one of the interfaces between contacting hydrogel objects does not comprise a bilayer of amphipathic molecules. This may be achieved, for example, by displacement of an existing bilayer at the interface of the contacting hydrogel objects. Usually, at least two of the interfaces between contacting hydrogel objects does not comprise a bilayer of amphipathic molecules. In some embodiments, at least half of the interfaces between contacting hydrogel objects do not comprise a bilayer of amphipathic molecules. When, in the hydrogel networks of the invention, an interface between contacting hydrogel objects does not comprise a bilayer of amphipathic molecules, the hydrogel bodies of the hydrogel objects may be in direct contact with each other at the interface or the interface may comprise a layer of a material or a compound other than a bilayer of amphipathic molecules, such as a thin layer of a hydrophobic or hydrophilic medium, or another polymer, between the two hydrogel objects. The hydrophobic medium may be as further defined herein.

Thus, in some embodiments, the hydrogel body of one hydrogel object is in direct contact with the hydrogel body of another hydrogel object at least one of said interfaces between contacting hydrogel objects.

For instance, at least two of said interfaces between contacting hydrogel objects, the hydrogel body of a hydrogel object may be in direct contact with the hydrogel body of another hydrogel object.

In some embodiments, none of the interfaces between contacting hydrogel objects comprise a bilayer of amphipathic molecules. In these embodiments, the hydrogel bodies of the hydrogel object may be in direct contact with one another or the interface may comprise a thin layer of some other material or compound, for example a thin layer of a hydrophobic medium such as an oil. The hydrophobic medium or oil may be as further defined herein.

Thus, in some embodiments, at each of the interfaces between contacting hydrogel objects, the hydrogel body of one said hydrogel object may be in direct contact with the hydrogel body of another said hydrogel objects.

In some instances, it may be advantageous for all of the interfaces between contacting hydrogel objects in the hydrogel network of the invention to comprise a bilayer of amphipathic molecules. A bilayer can act as a barrier to prevent diffusion of substances from one hydrogel body to the next hydrogel body, and can advantageously therefore help to contain or "store" particular chemicals within particular hydrogel bodies. On the other hand, the bilayers may be modified to allow the network to be functionalised in a variety of ways. For example, a membrane protein may be inserted into the bilayer enabling the flow of information across a network. Alternatively, it may be advantageous for none of the interfaces between contacting hydrogel objects to comprise a bilayer of amphipathic molecules. The absence of a bilayer provides advantages such as improved (faster) transport of ions through the network. There may also be instances for which it may be advantagous for the hydrogel network to comprise at least one interface comprising a bilayer of amphipathic molecules and at least one interface that does not comprise a bilayer of amphipathic molecules. Such systems are particularly advantageous because they can provide a combination of the advantages mentioned above for systems with, and systems without, bilayers. Networks in which some of the interfaces comprise bilayers and others do not can be particularly useful as electrochemical circuits, as described in the Examples, and in synthetic biology.

Accordingly, in some embodiments, at least one of the interfaces between contacting hydrogel objects comprises a bilayer of amphipathic molecules, and at least one other of the interfaces between contacting hydrogel objects does not comprise a bilayer of amphipathic molecules. In some embodiments, two or more of the interfaces between contacting hydrogel objects comprise a bilayer of amphipathic molecules, and/or two or more of the other interfaces between contacting hydrogel objects do not comprise a bilayer of amphipathic molecules.

For instance, in the hydrogel network of the invention, at least one of the interfaces between contacting hydrogel objects may comprise a bilayer of amphipathic molecules, and, at least one other of the interfaces between contacting hydrogel objects, the hydrogel body of one hydrogel object may be in direct contact with the hydrogel body of another hydrogel object. In some embodiments, two or more of the interfaces between contacting hydrogel objects comprise a bilayer of amphipathic molecules, and/or at two or more of the other interfaces between contacting hydrogel objects, the hydrogel bodies at those interfaces are in direct contact with each other.

In the hydrogel network of the invention, the plurality of hydrogel objects is typically surrounded by a layer of the amphipathic molecules.

The layer of amphipathic molecules surrounding the plurality of hydrogel objects is usually made up of the outer layers of amphipathic molecules of the hydrogel objects in the network. The outer layers of amphipathic molecules may comprise one type of amphipathic molecule or may comprise two or more different types of amphipathic molecules. Thus the layer of amphipathic molecules surrounding the plurality of hydrogel objects may comprise one type of amphipathic molecule or may comprise two or more different types of amphipathic molecules.

In some embodiments of the hydrogel network of the invention, one or more of the hydrogel objects comprises: (a) said hydrogel body, and (b) said outer layer of amphipathic molecules around at least part of the surface of the hydrogel body, wherein the outer layer of amphipathic molecules covers at least 50% of the area of the surface of the hydrogel body.

The outer layer of amphipathic molecules of a hydrogel object does not necessarily cover the whole of the surface of the hydrogel body. For instance, when the hydrogel body of one hydrogel object is in direct contact with the hydrogel body of another hydrogel object, there will be no outer layer of amphipathic molecules that covers the entire surface of either hydrogel body. This is because no such outer layer of amphipathic molecules will be present at the interface between the contacting hydrogel bodies. Similarly, when two hydrogel bodies are pushed together so as to squeeze out the bilayer of amphipathic molecules between them, there may be no amphipathic molecules present at the interface between the objects, and therefore the outer layer of amphipathic molecules will not cover the entire surface of either hydrogel body. Thus, the portion of the surface area of the hydrogel body that is covered by an outer layer of amphipathic molecules may be dictated by the interface(s) which the hydrogel object forms with other hydrogel objects in the network, and by other factors such as the shape of the hydrogel bodies.

Typically, each hydrogel object in the hydrogel network comprises: (a) said hydrogel body, and (b) said outer layer of amphipathic molecules around at least part of the surface of the hydrogel body, wherein the outer layer of amphipathic molecules covers at least 50% of the area of the surface of the hydrogel body.

In some embodiments, one or more of the hydrogel objects in the hydrogel network comprises: (a) said hydrogel body, and (b) said outer layer of amphipathic molecules around the whole of the surface of the hydrogel body. For instance, in a hydrogel network in which all of the hydrogel objects are in contact with each other to form bilayers at the interfaces, typically all of those hydrogel objects will comprise an outer layer of amphipathic molecules around the whole of the surface of the hydrogel body.

Thus, in some embodiments, all of the hydrogel objects in the hydrogel network comprise: (a) said hydrogel body, and (b) said outer layer of amphipathic molecules around the whole of the surface of the hydrogel body.

If, for instance, the only interfaces in the network are interfaces comprising a bilayer of amphipathic molecules, then the hydrogel bodies of the hydrogel objects in the network will typically comprise a said outer layer of amphipathic molecules around the whole of the surface of the hydrogel body. Thus, in a hydrogel network in which all of said interfaces comprise a bilayer of amphipathic molecules, usually all of the hydrogel objects in the hydrogel network comprise said hydrogel body, and said outer layer of amphipathic molecules around the whole of the surface of the hydrogel body.

Usually, in the hydrogel network of the invention, the hydrogel body of at least one of said hydrogel objects is molded. Typically, the hydrogel body of two or more of said hydrogel objects are molded, for instance, at least three may be molded. In some embodiments, at least half of the hydrogel bodies are molded. For instance, all of the hydrogel bodies may be molded.

If a hydrogel body is molded, it may be molded by any suitable method. Typically, a template will be used to produce the molded hydrogel body. For instance, a PMMA (poly(methyl methacrylate)) mold may be used.

Typically, the hydrogel body of at least one of said hydrogel objects is a molded three-dimensional hydrogel shape. Usually, two or more of said hydrogel bodies are molded three-dimensional hydrogel shapes. For instance at least three of said hydrogel bodies may be molded three-dimensional hydrogel shapes. In some embodiments, at least half of the hydrogel bodies are molded three-dimensional hydrogel shapes. For instance, the hydrogel body of each of said hydrogel objects may be a three-dimensional hydrogel shape.

The hydrogel body may be as herein defined.

As mentioned above, the hydrogel body may be any three-dimensional shape. Typically, the three-dimensional shape is spherical, cross-shaped, cuboid, crescent-shaped, prism-shaped, cylindrical, wire-shaped or a shape which has a triangular, pentagonal, hexagonal, square or rectangular face.

The assembly of hydrogel objects in the hydrogel network may be controlled by any suitable methods. Shape, surface energy or molecular recognition may be used to control the assembly. Additionally or alternatively, the assembly of hydrogel objects in the hydrogel network may, for instance, be controlled by the use of stimuli such as temperature, pH, light, chemicals, ions, and magnetic and electrical fields, by the use of surfaces with switchable properties, or by manual manipulation.

The hydrogel bodies in the network may be any suitable combination of shapes. Further, the arrangement of hydrogel objects in the network can be arranged and/or rearranged to control the assembly of hydrogel objects. For example, the arrangement may be manipulated, for instance manually manipulated. If the arrangement is manipulated manually, a needle, for instance a steel needle, is typically used.

In some embodiments, hydrogel body of at least one of said hydrogel objects is in the shape of a wire. For instance, two or more of said hydrogel objects are in the shape of a wire. In some embodiments at least half of the hydrogel bodies are in the shape of a wire, for instance, all of the hydrogel bodies may be in the shape of a wire.

The wire-shaped hydrogel object may, in some embodiments, have a diameter of less than or equal to 10 mm, for instance, less than or equal to 5 mm. For instance, the wire-shaped hydrogel object may have a diameter of from 0.005 mm to 2 mm, for instance from 0.5 mm to 2 mm. For instance, the wire-shaped hydrogel object may have a diameter of about 0.5 mm. Alternatively, it may have a diameter of from about 1 mm to about 2 mm.

In some embodiments, the wire-shaped hydrogel object will have a length of equal to or greater than 0.5 mm, for instance, equal to or greater than 2 mm. The length of the wire-shaped hydrogel object is usually its largest dimension. The largest dimension is usually as defined herein below.

The diameter of a wire shaped hydrogel object will usually be less than the length of that hydrogel object. Typically, of course, it will be substantially less, for instance, less than a quarter of the length of the hydrogel object, or less than a tenth of the length of the hydrogel object.

At least one of said bilayers may further comprise a membrane protein. The membrane protein may be of any type. The use of integral membrane proteins has been demonstrated, but it is equally expected that peripheral membrane proteins could be used. The membrane protein may for instance be a membrane pump, channel and/or pore, to allow for precise control over the exchange of material, and electrical communication, between the hydrogel objects. When the hydrogel network forms part of a droplet encapsulate (as discussed below), the membrane protein allows for precise control over the exchange of material, and electrical communication, between the hydrogel network and an external solution. The membrane protein could for instance be an αHL pore. However, any suitable membrane protein can be used including the two major classes that is β-barrels or α-helical bundles. An important application is a membrane protein which is a pore or a channel. Besides a protein pore or channel, further possible membrane proteins include, but not exclusively, a receptor, a transporter or a protein which effects cell recognition or a cell-to-cell interaction. The bilayer at an interface between hydrogel objects, may comprise more than one membrane protein. For instance, a particular bilayer may contain multiple copies of the same membrane protein, or two or more different classes of membrane proteins. Where more than one class is present, the bilayer may contain multiple copies of each different class.

Suitable membrane proteins which allow for exchange of materials and electrical communication are known and readily available to the skilled person; many such proteins are either commercially available or can be prepared by known methods. For instance, WT αHL monomers can be prepared by in vitro transcription-translation (IVTT), and heptamerised by incubation with rabbit red blood cell membranes. The heptamers are typically purified by sodium dodecyl sulphate polyacrylamide gel electrophoresis (SDS-PAGE) (Maglia, G. et al. Method. Enzymol. 475, 591-623, 2010). Also, Bayley, H. et al. Droplet interface bilayers. Mol. BioSyst. 4, 1191-1208 (2008) lists several proteins that were tested for insertion into droplet interface bilayers made in bulk oil.

In some embodiments, two or more of said bilayers further comprise a membrane protein, wherein each of said membrane protein is as herein defined. For instance, each of said bilayers may further comprise a membrane protein, wherein each of said membrane protein is as herein defined.

Hydrogel objects can exchange chemical species with each other through membrane proteins incorporated in the bilayer between the hydrogel objects. Suitable membrane proteins include, but are not limited to, pumps, channels and/or pores, receptor proteins, transporter proteins, and/or proteins which effect cell recognition or a cell-to-cell interaction, for instance an α-hemolysin (αHL) pore. Thus, a hydrogel network of the invention is capable of trafficking materials such as chemical compounds through the network, from object to object, as well as to and from the external environment. Complex transport systems can be built up in this way.

A hydrogel object in the network may, for instance, act as a sensor module, capable of sensing the presence of a particular chemical in the external environment, for instance, or capable of sensing light. Thus, the hydrogel object may in some embodiments comprise a sensor molecule. The sensor molecule can be present in the hydrogel body or in the bilayer. The sensor molecule may be a molecule which is sensitive to the presence of a particular chemical (for instance a target analyte), or it may be a light-sensitive molecule.

As mentioned above, a hydrogel body may be any shape. A hydrogel body may also be any suitable size. Different hydrogel bodies in the hydrogel network may be the same size or a variety of different sizes. Typically, at least one of the hydrogel bodies has a diameter of less than or equal to 50 mm.

When the hydrogel object is a sphere, the diameter of the hydrogel object is the diameter of the sphere. When the hydrogel object is a cylindrical, the diameter is equal to the diameter of either of the circular faces of the cylinder. When the hydrogel object is a wire-shape, the diameter is equal to the diameter of the cross-section of the wire-shape, wherein the cross-section is taken at right angles to the length of the wire-shape. When the hydrogel object is a shape other than a sphere, cylinder or wire-shape the diameter of the hydrogel object is the diameter of a sphere that has the same volume as the hydrogel object.

In some embodiments, at least one of the hydrogel bodies has a diameter of less than or equal to 20 mm, preferably less than or equal to 5 mm. Typically, at least one of the hydrogel bodies has a diameter of from 0.1 mm to 50 mm, for instance, 0.5 mm to 20 mm. Usually, two or more of the hydrogel bodies have a diameter of less than or equal to 20 mm, preferably less than or equal to 5 mm. Typically, two or more of the hydrogel bodies have a diameter of from 0.1 mm to 50 mm, for instance, 0.5 mm to 20 mm. For instance, at least half of the hydrogel bodies may have a diameter of less than or equal to 20 mm, preferably less than or equal to 5 mm. Typically, at least half of the hydrogel bodies have a diameter of from 0.1 mm to 50 mm, for instance, 0.5 mm to 20 mm. In some embodiments, each of the hydrogel bodies has a diameter of less than or equal to 20 mm, preferably less than or equal to 5 mm. Typically, each of the hydrogel bodies have a diameter of from 0.1 mm to 50 mm, for instance, 0.5 mm to 20 mm.

In some embodiments, the largest dimension of at least one of the hydrogel bodies is less than or equal to 100 mm, for instance, less than or equal to 50 mm. Usually, the largest dimension of at least one of the hydrogel bodies is less than or equal to 25 mm, for instance, less than 5 mm. The largest dimension of at least one of the hydrogel bodies may, for instance, be from 0.1 to 100 mm. Usually, the largest dimension of at least one of the hydrogel bodies is from 0.5 to 50 mm, for instance, from 0.5 to 25 mm. The largest dimension of at least one of the hydrogel bodies may, for example, be from 0.5 to 5 mm. For example, when the hydrogel network comprises at least one wire-shaped hydrogel body, the largest dimension of the wire-shaped hydrogel body (or bodies) in the network may be as defined above. In the case of a wire-shaped hydrogel body, the largest dimension will typically be the length of the wire shape when placed in a straight line. Similarly, the largest dimension of a cylindrical hydrogel body will usually be the length of the cylinder i.e. the distance between the two circular faces of the cylinder. In some embodiments, the largest dimension of two or more or the hydrogel bodies present in the network is the largest dimension as defined above. For instance, the largest dimension of at least half of the hydrogel bodies in the network may be as define above. In some embodiments, the largest dimension of each and every one of the hydrogel bodies in the hydrogel network is as defined above.

When the hydrogel body is shape other than wire-shaped, the volume of the hydrogel body is typically at least 0.001 mm$^3$, for instance at least 0.005 mm$^3$. More typically, the volume of the hydrogel body is typically at least 0.008 mm$^3$. The hydrogel body usually has dimensions (length, width and height) of at least 0.1 mm×at least 0.1 mm×at least 0.1 mm. For instance, the hydrogel body may have dimensions of at least 0.175 mm (length)×at least 0.175 mm (width)×at least 0.175 mm (height), for instance, dimensions of at least 0.2 mm (length)×at least 0.2 mm (width)×at least 0.2 mm (height).

Techniques such as soft lithography can be used to produce hydrogel objects having particularly small dimensions.

Very small droplets may, for instance, be produced by disposing, for example, liquid or melted hydrogel, from a syringe or needle.

Typically, the hydrogel body comprises a hydrogel comprising agarose. Thus, typically, the hydrogel comprises said agarose and water. The concentration of the agarose in the water is usually less than or equal to 10% w/v agarose. For instance the concentration of the agarose may be less than or equal to 5% w/v agarose. Usually, the concentration of the agarose in the water is about 1% w/v agarose.

Hydrogels other than agarose can also be used. For instance the hydrogel body may comprise methylcellulose, polyethylene glycol diacrylate, polyacrylamide, matrigel, hyaluronan, polyethylene oxide, polyAMPS (poly(-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the hydrogel body may comprise a silicone hydrogel or LB (Luria broth) agar.

Individual hydrogel bodies in the hydrogel network may comprise the same hydrogel or different hydrogels. Thus the hydrogel of each hydrogel body in the hydrogel network may be the same or different.

Usually, the concentration of the agarose in said water is from 0.25 to 5% w/v agarose. For instance, the concentration of the agarose in said water may be from 0.5 to 2% w/v agarose.

The agarose may, for instance, be a low melt agarose.

In some embodiments, at least one of said plurality of hydrogel objects of the hydrogel network of the invention is a Janus particle comprising: (a) a hydrogel body comprising a hydrophilic material and a hydrophobic material, and (b) an outer layer of amphipathic molecules, on at least part of the surface of the hydrogel body.

The hydrophilic material of the Janus particle may, for instance, comprise agarose. For example, hydrophilic material of the Janus particle may comprise agarose and water. The concentration of the agarose in the water may be less than or equal to 10% w/v agarose. For instance, the concentration of the agarose may be less than or equal to 5% w/v agarose. The concentration of the agarose in the water may, for instance, be about 1% w/v agarose.

Typically, when the hydrogel network of the invention comprises a Janus particle, the outer layer of amphipathic molecules, on at least part of the surface of the hydrogel body, is an outer layer on the hydrophilic material of the hydrogel body.

The Janus particle may be any shape. The hydrogel body of the Janus particle may, for instance, be any regular or irregular shape, or any polygon. When the hydrogel body is a polygon, it may be convex or non-convex. The hydrogel body of the Janus particle may, for instance, be a molded three-dimensional hydrogel shape. Typically, the three-dimensional shape is spherical, cross-shaped, cuboid, crescent-shaped, prism-shaped, cylindrical, wire-shaped or a shape which has a triangular, pentagonal, hexagonal, square or rectangular face.

The hydrogel body comprising a hydrophilic material and a hydrophobic material may, for example, be a spherical hydrogel body made up of a hemisphere of a hydrophilic material and a hemisphere of a hydrophobic material. Alternatively, the hydrophobic material may be in the centre of the Janus particle, and surrounded by the hydrophilic material. However, any suitable arrangement of at least one hydrophilic material and at least one hydrophobic material may be used. The Janus particle may, for instance, comprise a first hydrophilic material, a hydrophobic material and a second hydrophilic material, wherein (i) the first and second hydrophilic materials may be the same or different; and (ii) the first and second hydrophilic materials are not in contact with each other. Similarly, the Janus particle may, for instance, comprise a first hydrophobic material, a hydrophilic material and a second hydrophobic material, wherein (i) the first and second hydrophobic materials may be the same or different; and (ii) the first and second hydrophobic materials are not in contact with each other.

The Janus particle thus allows compartments to be formed within the hydrogel body. Individual compartments may, for instance, be used as a store for a small molecule, such as a dye or a magnet, a sensor molecule, a therapeutic agent or a diagnostic agent. This may, for example, permit a concentration gradient to form within the hydrogel body. If a concentration gradient were to form, this may lead to the diffusion of small molecules, such as dyes or magnets, sensor molecules, therapeutic agents or diagnostic agents to diffuse from one compartment within the Janus particle to another compartment within the Janus particle.

In one embodiment, when the hydrogel network comprises a Janus particle, the hydrophilic material is on one side of the hydrogel body and the hydrophobic material is on the other side of the hydrogel body.

The hydrogel network may comprise two or more Janus particles. Thus, the hydrogel network may comprise two or more hydrogel objects comprising: (a) a hydrogel body comprising a hydrophilic material and a hydrophobic material, and (b) an outer layer of amphipathic molecules, on at least part of the surface of the hydrogel body. For instance, the hydrogel network may comprise two, three or four hydrogel objects comprising: (a) a hydrogel body comprising a hydrophilic material and a hydrophobic material, and (b) an outer layer of amphipathic molecules, on at least part of the surface of the hydrogel body.

The amphipathic molecules may be any suitable amphipathic molecule. Usually, the amphipathic molecules will be ones which are capable, when present in a high enough concentration, of forming a bilayer at any one of said interfaces. The type of amphipathic molecule that is capable of forming a bilayer may, for instance, depend on additional components of the hydrogel network. For example, if the network further comprises a hydrophobic medium, the amphipathic molecules may be, for instance, any suitable amphipathic molecules capable of forming a bilayer within the hydrophobic medium. The type of amphipathic molecules capable of forming a bilayer within the hydrophobic medium would typically depend on the nature of the hydrophobic medium and the hydrogel of the hydrogel bodies, but a wide range of amphipathic molecules are possible.

Amphipathic molecules are molecules which have both hydrophobic and hydrophilic groups. The outer layer of amphipathic molecules formed on at least part of the surface of the hydrogel body usually comprises a monolayer of amphipathic molecules on said at least part of the surface of the hydrogel body. The monolayer is typically formed and maintained spontaneously by the interaction of the hydrophobic and hydrophilic groups with the aqueous medium so that the molecules align on the surface of the hydrogel body with the hydrophilic groups facing inwards towards the aqueous medium and the hydrophobic groups facing outwards, for instance towards a hydrophobic medium. Likewise, the layer of amphipathic molecules that may surround the plurality of hydrogel objects usually comprises a monolayer of amphipathic molecules which is formed and maintained spontaneously by the interaction of the hydrophobic and hydrophilic groups.

The amphipathic molecules may, for instance, be non-polymeric amphipathic molecules. Alternatively, the amphipathic molecules may be polymeric amphipathic molecules.

An important class of amphipathic molecules which can be used in the hydrogel networks of the invention is lipid molecules. The lipid molecules may be any of the major classes of lipid, including phospholipids, fatty acids, fatty acyls, glycerolipids, glycerophospholipids, sphingolipids, sterol lipids, prenol lipids, saccharolipids and polyketides. Some important examples include phospholipids and fatty acids, for instance phospholipids. The lipid molecules may be naturally occurring or synthetic. Whilst the formation of a bilayer from lipid molecules has been demonstrated the method is expected to be appropriate for any amphipathic molecules.

A common class of hydrophobic group that may be present in an amphipathic molecule is a hydrocarbon group, as for instance in most lipids. However, another suitable kind of hydrophobic group that may be employed is a fluorocarbon group. Thus, a further important class of amphipathic molecule is an amphipathic molecule that comprises at least one fluorocarbon group. An example of such a molecule would be a lipid-like molecule which comprises a hydrophobic fluorocarbon tail and a hydrophilic head group.

The amphipathic molecules in the hydrogel network need not be all of the same type. Rather, the amphipathic molecules may in some embodiments be a mixture of two or more different kinds of amphipathic molecule. Another example is that the amphipathic molecules in the respective outer layers of different hydrogel objects in the hydrogel network may be of different types so that, if bilayers are formed, the bilayer(s) formed between the different hydrogel objects may be asymmetric.

Typically, therefore, the amphipathic molecules in the hydrogel network of the invention comprise lipid molecules. The lipid molecules need not be all of the same type. Thus, the amphipathic molecules in the hydrogel network of the invention may comprise a single type of lipid or a mixture of two or more different lipid molecules. Also, the lipid composition of the layer surrounding the plurality of hydrogel objects may be the same as or different from that of the outer layer of the individual hydrogel objects. Likewise, the lipid compositions of the outer layers of the individual hydrogel objects may be the same as or different from one another. Lipid molecules are particularly advantageous because lipid bilayers, or more generally bilayers of amphipathic molecules, are models of cell membranes and the hydrogel network of the invention may therefore serve as excellent platforms for a range of experimental studies, including for instance as novel platforms for the fundamental study of membrane proteins, or as multi-compartment protocellular chassis for "bottom-up" synthetic biology.

Phospholipids are particularly preferred for reasons outlined above and also because they are a major component of all cell membranes, making hydrogel networks comprising phospholipids particularly suitable for synthetic biology applications, as well as for drug delivery.

Accordingly, the amphipathic molecules in the hydrogel network of the invention typically comprise phospholipid molecules. The phospholipid molecules may be the same or different, i.e. the amphipathic molecules in the hydrogel network may comprise a single kind of phospholipid, or a mixture of two or more different phospholipids. Phospholipids are well known to the skilled person and many are commercially available, from suppliers such as Avanti Polar Lipids. The phospholipid molecules may be glycerophospholipids or phosphosphingolipids or a mixture of the two. The phospholipid molecules may comprise anionic phospholipids, phospholipids comprising primary amines, choline-containing phospholipids and/or glycosphingolipids. Usually, the amphipathic molecules comprise one or more glycerophospholipids. As the skilled person will appreciate, glycerophospholipids include, but are not limited to glycerophospholipids having a structure as defined in the following formula (I):

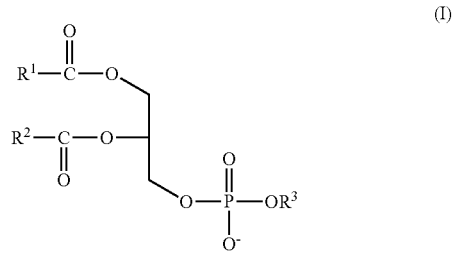

wherein:

$R^1$ and $R^2$, which are the same or different, are selected from $C_{10}$-$C_{25}$ alkyl groups and $C_{10}$-$C_{25}$ alkylene groups;

either $R^3$ is absent such that $OR^3$ is $O^-$, or $R^3$ is present and is H, $CH_2CH_2N(R^4)_3{}^+$, a sugar group, or an amino acid group; and each $R^4$, which is the same or different, is independently selected from H and unsubstituted $C_1$-$C_4$ alkyl.

Typically, when $R^3$ is $CH_2CH_2N(R^4)_3{}^+$, each $R^4$, which is the same or different, is selected from H and methyl. As the skilled person will appreciate, when each and every $R^4$ is methyl, the $R^3$ group is a choline group, and when each and every $R^4$ is H, the $R^3$ group is an ethanolamine group.

When $R^3$ is an amino acid group it may for instance be a serine group, i.e. —$CH_2CH(NH_2)(COOH)$. When $R^3$ is a sugar group, it may for instance be glycerol, i.e. —$CH_2CHOHCH_2OH$, or for instance inositol, i.e. —CH$(CHOH)_5$.

Typical examples of $R^1$ and $R^2$ groups are $C_{10}$-$C_{25}$ alkyl groups, including, but not limited to linear $C_{10}$-$C_{25}$ alkyl groups such as, for instance, $CH_3(CH_2)_{10}$—, $CH_3(CH_2)_{12}$—, $CH_3(CH_2)_{14}$—, $CH_3(CH_2)_{16}$—, $CH_3(CH_2)_{18}$—, $CH_3(CH_2)_{22}$— and branched $C_{10}$-$C_{25}$ alkyl groups such as for instance —$CH_2$—$CH(CH_3)$—$(CH_2)_3$—$CH(CH_3)$—$(CH_2)_3$—$CH(CH_3)$—$(CH_2)_3$—$CH(CH_3)_2$.

Further typical examples of $R^1$ and $R^2$ groups are unsubstituted $C_{10}$-$C_{25}$ alkylene groups, including, but not limited to, $CH_3(CH_2)_5CH=CH(CH_2)_7$—, $CH_3(CH_2)_7CH=CH(CH_2)_7$—, $CH_3(CH_2)_4CH=CHCH_2CH=CH(CH_2)_7$—, $CH_3(CH_2)_4(CH=CHCH_2)_3CH=CH(CH_2)_3$—, and $CH_3CH_2CH=CHCH_2CH=CHCH_2CH=CH(CH_2)_7$—.

As the skilled person will appreciate, the $O^-$ group in the phosphate group adjacent the $OR^3$ group may in some embodiments be protonated, or associated with a suitable cation, for instance a metal cation such as $Na^+$.

Thus, the amphipathic molecules may comprise one or more glycerophospholipids having the structure of formula (I) as defined above.

For instance, the amphipathic molecules may comprise any one or more of the following glycerophospholipids: 1,2-diphytanoyl-sn-glycero-3-phosphocholine (DPhPC), 1,2-distearoyl-sn-glycero-3-phosphocholine (DSPC), 1,2-dipalmitoyl-sn-glycero-3-phosphocholine (DPPC), or 1,2-dipalmitoyl-sn-glycero-3-[phospho-rac-(1-glycerol)] (DPPG), which can be employed as the amphiphilic molecules in the hydrogel network of the invention, or a mixture of one or more thereof. The glycerophospholipid 1,2-dioleoyl-sn-glycero-3-phosphoethanolamine (DOPE) may also be used, and can be used often in combination with a pH-sensitive lipid, for instance a fatty acid.

Preferably, the amphipathic molecules comprise DPhPC.

The amphipathic molecules in the hydrogel network of the invention may comprise one or more fatty acids, e.g. oleic acid. Fatty acids are of course well known to the skilled person and a wide range of these are commercially available.

The amphipathic molecules may for instance comprise a mixture comprising: (a) one or more phospholipids, and (b) one or more fatty acids.

Additionally or alternatively, the amphipathic molecules may comprise a steroid, which steroid comprises an alkyl side-chain. The amphipathic molecules may, for instance, comprise cholesterol, β-sitosterol and lanosterol.

In some embodiments, the amphipathic molecules comprise derivatives of phospholipids. For instance, the amphipathic molecules may comprise a phosphatidylcholine, such as POPC (1-Palmitoyl-2-oleoyl-sn-glycero-3-phosphocholine) or DPPC (1,2-Dipalmitoyl-sn-glycero-3-phosphocholine), or a phosphatidylglycerol, such as POPG (1-palmitoyl-2-oleoyl-sn-glycero-3-phosphoglycerol).

The hydrogel network may form part of an encapsulate, for instance a droplet encapsulate. The encapsulate may, for instance, comprise: a volume (for instance a drop) of a hydrophobic medium; a peripheral layer of amphipathic molecules around the surface of the volume; and a hydrogel network within the peripheral layer, wherein the hydrogel network is a hydrogel network as defined herein. The amphipathic molecules which form the peripheral layer of the encapsulate may, in the process of the invention, be provided in the hydrophobic medium or in the bulk hydrophilic medium.

The droplet encapsulate, or "multisome", may, for example, communicate with the external environment through membrane proteins in the peripheral layer. In addition, membrane proteins may allow hydrogel objects within the same multisome to communicate with each other. This in principle allows multisomes to sense their environment, process information, and contingently deliver materials to the surroundings. The encapsulates may be produced by the methods described in GB patent application number 1119032.9 and U.S. patent application No. 61/592,062. The disclosures in GB 1119032.9 and U.S. 61/592,062 are incorporated herein by reference.

In addition to the amphipathic molecules, the hydrogel network of the invention may further comprise a PEGylated lipid. PEGylated lipid may be particularly useful when the hydrogel network forms part of a droplet encapsulate. The term "PEGylated lipid", as used herein, refers to a lipid which has been derivatised with poly(ethylene glycol). For instance, when the plurality of hydrogel objects is surrounded by a layer of amphipathic molecules, the layer surrounding the plurality of hydrogel objects may further comprise a PEGylated lipid.

The inclusion of one or more PEGylated lipids in the hydrogel network, for instance in the layer surrounding the plurality of hydrogel objects typically stabilises the hydrogel network in vivo, and in particular prolongs the plasma half-life of the hydrogel network. This means that, when the hydrogel network contains one or more therapeutic or diagnostic agents, for instance if it is being used as a drug-delivery vehicle, the inclusion of one or more PEGylated lipids in the layer surrounding the plurality of hydrogel objects may also have the useful effect of prolonging the plasma half-life of the agent within the hydrogel network. Such effects have been observed previously when PEGylated lipids are used in liposomal drug formulations. PEGylated lipids are known in the art and are commercially available from suppliers such as NOF Corporation, Japan (see http://www.phospholipid.jp/phospholipid_2-3.html). Any suitable PEGylated lipid may be employed in the present invention, including, but not limited to, PEG-phospholipids, diacylglycerol-PEG, cholesterol-PEG derivatives, and mixtures thereof.

Thus, in one embodiment, the layer surrounding the plurality of hydrogel objects of the hydrogel network of the invention further comprises a PEGylated lipid. The peripheral layer may include one or more PEGylated lipids in addition to the amphipathic molecules, for instance multiple copies of the same PEGylated lipid, or a mixture of two or more different classes of PEGylated lipids. Suitable PEGylated lipids include, but are not limited to PEG-phospholipids, diacylglycerol-PEG, cholesterol-PEG derivatives and mixtures thereof. The poly(ethylene glycol) (PEG) component of the PEGylated lipid may have any one of several different geometries. Thus, it could be substantially linear PEG or branched PEG. The branched PEG may for instance have from three to ten PEG chains emanating from a central core group. Alternatively, the branched PEG could be a star PEG, having from 10 to 100 PEG chains emanating from a central core group. Alternatively, the PEG may be a comb PEG, having multiple PEG chains grafted to a polymer backbone.

The one or more PEGylated lipids employed in the peripheral layer may for instance comprise a PEG-phospholipid of the following formula (II)

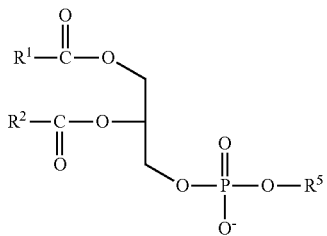

(II)

wherein $R^1$ and $R^2$ are as defined above for the glycerophospholipids of formula (I), and $R^5$ is a group which comprises poly(ethylene glycol).

The group which comprises poly(ethylene glycol) may for instance have the formula —$CH_2CH_2NHC(O)$—X, or for instance —$CH_2CH_2NHC(O)(CH_2)_3C(O)$—X wherein X comprises said poly(ethylene glycol). The group X may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

Thus, $R^5$ may for instance be —$CH_2CH_2NHC(O)$—$(OCH_2CH_2)_qOCH_3$, —$CH_2CH_2NHC(O)(CH_2)_3C(O)$—$(OCH_2CH_2)_qOCH_3$, —$CH_2CH_2NHC(O)$—$(OCH_2CH_2)_qOH$, or —$CH_2CH_2NHC(O)(CH_2)_3C(O)$—$(OCH_2CH_2)_qOH$, wherein q is a positive integer. The integer q may for instance be from 5 to 10,000, or for instance from 10 to 1,000.

Alternatively, $R^5$ may be —$(CH_2CH_2O)_qCH_3$ or —$(CH_2CH_2O)_qH$, wherein q is a positive integer. The integer q may for instance be from 5 to 10,000, or for instance from 10 to 1,000.

Additionally or alternatively, the one or more PEGylated lipids may comprise a diacylglycerol-PEG of formula (III)

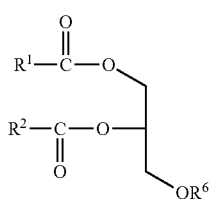

(III)

wherein $R^1$ and $R^2$ are as defined above for the glycerophospholipids of formula (I), and $R^6$ is a group which comprises poly(ethylene glycol).

The poly(ethylene glycol) may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

$R^6$ may for instance be —$(CH_2CH_2O)_qCH_3$, —$(CH_2CH_2O)_qH$, —$CH_2CH_2NHC(O)$—$(OCH_2CH_2)_qOCH_3$, —$CH_2CH_2NHC(O)$—$(OCH_2CH_2)_qOH$, —$CH_2CH_2NHC(O)(CH_2)_3C(O)$—$(OCH_2CH_2)_qOCH_3$ or —$CH_2CH_2NHC(O)(CH_2)_3C(O)$—$(OCH_2CH_2)_qOH$ wherein q is a positive integer. The integer q may for instance be from 5 to 10,000, or for instance from 10 to 1,000.

Additionally or alternatively, the one or more PEGylated lipids may comprise a cholesterol-PEG derivative of formula (IV)

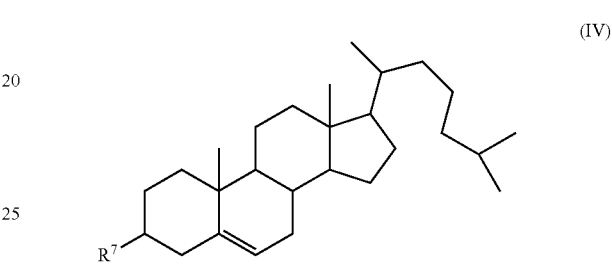

(IV)

wherein $R^7$ is a group which comprises poly(ethylene glycol).

Again, the poly(ethylene glycol) may comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

$R^7$ may for instance be —$(OCH_2CH_2)_qOH$ or —$(OCH_2CH_2)_qOCH_3$ wherein q is a positive integer. The integer q may for instance be from 5 to 10,000, or for instance from 10 to 1,000.

Polyglycerine may be used instead of poly(ethylene glycol), and so in one embodiment the layer surrounding the plurality of hydrogel objects of the hydrogel network of the invention may further comprise a lipid which comprises a polyglycerine moiety.

Typically, the hydrogel network of the invention further comprises a hydrophobic medium, wherein the plurality of hydrogel objects is disposed in the hydrophobic medium.

The hydrophobic medium may be selected from a wide range of materials. The hydrophobic medium may comprise a single hydrophobic compound. Alternatively, it may comprise a mixture of two or more different hydrophobic compounds. The hydrophobic medium can be selected to affect the buoyancy of the hydrogel objects in the hydrogel network and the speed of formation of the layer of amphipathic molecules around at least part of each hydrogel object in the hydrogel network when preparing the network.

The hydrophobic medium in the hydrogel network of the invention is typically an oil. The oil may be a single, pure, compound, or the oil may comprise a mixture of two or more compounds. It is usually desirable that the oil does not significantly destabilize any bilayers formed.

The oil may for instance comprise silicone oil (for instance poly phenyl methyl siloxane). The oil may consist of a single silicone oil, for instance poly phenyl methyl siloxane. Alternatively, the oil may comprise a mixture of two or more different silicone oils.

Any suitable silicone oil may be used. For instance, the oil may comprise silicon oil DC200 (a polymer comprising monomer units of —O—Si(CH$_3$)$_2$—), poly(dimethylsiloxane) (PDMS), hydroxy terminated, or PDMS 200.

Additionally or alternatively, the oil may comprise a hydrocarbon. When the oil comprises a hydrocarbon it may comprise a single hydrocarbon compound, or a mixture of two or more hydrocarbons.

In some embodiments, the oil is a mixture comprising: (a) one or more hydrocarbons, and (b) one or more silicone oils. The hydrocarbon may, for instance, be any suitable liquid hydrocarbon. Whether a particular hydrocarbon is liquid will depend upon the temperature of the hydrophobic medium. Thus the term liquid hydrocarbon refers to a hydrocarbon that is a liquid at the temperature that the hydrophobic medium is at. Typically, the hydrophobic medium will be at room temperature. However, in some embodiments, the hydrophobic medium may be above or below room temperature.

In some embodiments, the oil may comprise a solid. A solid hydrocarbon may, for instance, be used in combination with a silicone oil. The oil may, for instance, be a mixture of solids that dissolve to form a liquid.

When the oil comprises a hydrocarbon, the hydrocarbon may be branched or unbranched, for example a hydrocarbon having from 5 to 40 carbon atoms, or from 5 to 30 carbon atoms (although hydrocarbons of lower molecular weight would require control of evaporation). Suitable examples include alkanes or alkenes, such as hexadecane, decane, pentane or squalene. Usually, the oil comprises a hydrocarbon. The hydrocarbon may, for example, be a liquid at the operating temperature of the hydrogel network of the invention.

Typically the hydrocarbon is an unsubstituted $C_{10}$-$C_{20}$ alkane, for instance hexadecane.

Shorter alkanes may be suitable for hydrogel networks, for instance, in networks for which buoyancy effects are less important and whose outer layer of amphipathic molecules, on at least part of the surface of the hydrogel body, may form more quickly.

In some embodiments the hydrocarbon is a longer-chain hydrocarbon, such as unsubstituted $C_{15}$-$C_{40}$ alkane. For instance, an unsubstituted $C_{16}$-$C_{30}$ alkane chain, such as squalene.

In one embodiment, the hydrophobic medium comprises an unsubstituted $C_{10}$-$C_{20}$ alkane and the amphipathic molecules comprise one or more glycerophospholipids. For instance, the hydrophobic medium may comprise hexadecane and the outer layer of amphipathic molecules may comprise DPhPC.

Other types of oil are possible. For example the oil may be a fluorocarbon. This might be useful for the study of some systems, for example to minimise loss of a particular membrane protein or analyte from the hydrogel network or to control gas content such as oxygen. Because fluorocarbons can be both hydrophobic and lipophobic, an oil phase that comprises fluorocarbons can usefully prevent the adhesion of hydrogel network to surfaces.

In another embodiment, the hydrocarbon is a bromo-substituted $C_{10}$-$C_{30}$ alkane, or for instance a bromo-substituted $C_{10}$-$C_{20}$ alkane, e.g. bromododecane.

Typically, the oil comprises silicone oil or a hydrocarbon. Any suitable silicone oil may be employed. Usually, the silicone oil is as herein defined.

Silicone oil is advantageous on account of its density being close to that of water, which ensures that the hydrogel network is approximately neutrally buoyant in water. The silicone oil may for instance be poly phenyl methyl siloxane, which has a density of about 1 g·cm$^{-3}$.

The hydrocarbon typically has from 5 to 40 carbon atoms (a $C_5$-$C_{40}$ hydrocarbon), more typically from 10 to 30 carbon atoms (a $C_{10}$-$C_{30}$ hydrocarbon). Typically, it is an alkane or an alkene. Thus, the hydrocarbon may be a $C_5$-$C_{30}$ alkane, or a $C_{10}$-$C_{20}$ alkane. In another embodiment, the hydrocarbon may be a $C_5$-$C_{20}$ alkene, or a $C_{10}$-$C_{20}$ alkene. The hydrocarbon is typically unsubstituted. In one embodiment it is squalene. In a preferred embodiment, the hydrocarbon is an unsubstituted $C_5$-$C_{20}$ alkane, preferably an unsubstituted $C_{10}$-$C_{20}$ alkane. The hydrocarbon may for instance be squalene, hexadecane or decane. However, in some embodiments the hydrocarbon may be substituted with a halogen atom, for instance bromine.

In some embodiments, the hydrophobic medium comprises a mixture of silicone oil and a hydrocarbon. Such mixtures have been found to provide advantageously low incubation times for stable hydrogel networks to be formed. The silicone oil and hydrocarbon in the mixture may be as further defined above. Typically, the hydrocarbon is an unsubstituted $C_{10}$-$C_{20}$ alkane, preferably hexadecane. The silicone oil and hydrocarbon mixture typically has a density close to that of water, to ensure the hydrogel network has approximately neutral buoyancy in aqueous media; it may for instance be poly phenyl methyl siloxane. Usually, the volume ratio of the silicone oil to the hydrocarbon is equal or greater than 0.5:1. The volume ratio of the silicone oil to the hydrocarbon may for instance be from 0.5:1 to 5:1, for instance about 1:1. In some embodiments, the volume ratio of the silicone oil to the hydrocarbon is equal or greater than 5:1.

The hydrophobic medium employed in the hydrogel network of the invention may, for instance, have a density close to that of water, for instance a density of about 1 g·cm$^{-3}$, such that the hydrogel network of the invention are approximately neutrally buoyant in water.

In one embodiment, the hydrophobic medium comprises both silicone oil and hexadecane. Typically the silicone oil is poly phenyl methyl siloxane. The volume ratio of the silicone oil to the hexadecane is typically equal or greater than 0.5:1, for instance from 0.5:1 to 5:1. It may for instance be about 1:1. In some embodiments, the volume ratio of the silicone oil to the hydrocarbon is equal or greater than 5:1.

Preferably, the hydrophobic medium comprises hexadecane.

More preferably, hydrophobic medium comprises hexadecane and the amphipathic molecules comprise DPhPC.

In some embodiments, the hydrophobic medium comprises hexadecane, the amphipathic molecules comprise DPhPC and the hydrogel in the hydrogel bodies comprises agarose. Typically, the hydrogel comprises agarose and water. The concentration of the agarose in water is typically less than or equal to 10% w/v agarose. For instance, the concentration of the agarose in said water may be from 0.25 to 5% w/v agarose. More typically, the concentration of the agarose in said water is from 0.5 to 4% w/v, for instance, from about 1% w/v to 3% w/v. Usually, the concentration of the agarose in said water is about 1% w/v or 3% w/v.

As mentioned above, the hydrogel body may comprise agarose. In some embodiments, the agarose may, for instance, be dissolved in a buffer solution. The hydrogel body may be freely chosen for the purpose or use of the hydrogel network, or for the experiment to be performed using the hydrogel network. The hydrogel of each hydrogel body in the hydrogel network may be the same or different. One important property is pH and this can be varied over a wide range. In some embodiments, for instance, the pH of the aqueous medium within the hydrogel objects may be in the range of from 3 to 9 (or for instance in the range of from 5 to 9) although higher and lower pHs are also possible. In one embodiment, the pH of the aqueous medium within the hydrogel objects may be in the range of from 6 to 8. The hydrogel body may therefore comprise an aqueous buffer solution. Any suitable buffer can be employed, depending on the desired pH. The buffer solution may for instance comprise Tris HCl, with KCl. In some embodiments the pH of the aqueous buffer solution is from 3 to 9, or for instance from 5 to 9. In some embodiments the pH of the aqueous buffer solution is from 6 to 8. The nature and concentration of the solutes can be varied to vary the properties of the solution.

The concentration of amphipathic molecules may be any suitable concentration. The inventors have found that the concentration of amphipathic molecules can be changed in order to control whether or not an interface comprises a bilayer of amphipathic molecules. High concentrations ensure an interface will comprise a bilayer of amphipathic molecules. Increases in the concentration of amphipathic molecules may therefore be used to increase the number of interfaces comprising a bilayer of amphipathic molecules and decrease the number of interfaces that do not comprise a bilayer of amphipathic molecules. Decreasing the concentration of amphipathic molecules may be used to decrease the number of interfaces comprising a bilayer of amphipathic molecules. For example, decreasing the concentration of amphipathic molecules may be used to increase the number of interfaces at which two hydrogel bodies are in direct contact.

As the skilled person will appreciate, the concentration of amphipathic molecules required for the formation of a bilayer at an interface may depend upon the size and shape of the hydrogel body.

Further, changing the concentration of amphipathic molecules is not be the only way to control whether or not an interface comprises a bilayer of amphipathic molecules. For example, a bilayer of amphipathic molecules between two hydrogel objects in the hydrogel network may be removed by pushing together the two hydrogel objects, in order to "squeeze out" the bilayer from between the two objects and/or prevent a bilayer from being formed between the objects. Thus, the concentration of amphipathic molecules may not be the only factor that dictates whether a bilayer is formed.

Typically, the concentration of amphipathic molecules is less than or equal to 15 mg mL$^{-1}$. For instance, the concentration of amphipathic molecules may be from 0 to 10 mg mL$^{-1}$.

In some embodiments, the concentration of amphipathic molecules is usually equal to or greater than 0.5 mg mL$^{-1}$. For instance, the concentration of amphipathic molecules may be equal to or greater than 5 mg mL$^{-1}$. Usually, the concentration of amphipathic molecules is from 0.5 mg mL$^{-1}$ to 15 mg mL$^{-1}$, for instance, from 5 mg mL$^{-1}$ to 15 mg mL$^{-1}$. In order for a bilayer to form at an interface, the concentration of amphipathic molecules usually needs to be equal to or greater than 1 mg mL$^{-1}$, for instance equal to or greater than 5 mg mL$^{-1}$.

In other embodiments, the concentration of amphipathic molecules is from 0.5 to 10 mg mL$^{-1}$. Usually, the concentration of amphipathic molecules is from 5 to 10 mg mL$^{-1}$.

The inventors have found that these concentration ranges are favourable for stabilising hydrogel networks that comprise at least one interface that comprises a bilayer of amphipathic molecules and at least one other interface that does not comprise a bilayer of amphipathic molecules. Likewise, these concentration ranges have been found to favour hydrogel networks which comprise at least one interface that comprises a bilayer of amphipathic molecules, and at least one other interface at which the hydrogel body of one hydrogel object is in direct contact with the hydrogel body of another hydrogel object. In this case, the concentration of the amphipathic molecules may therefore be from 5 to 10 mg mL$^{-1}$.

In a further embodiment, the concentration of amphipathic molecules is less than or equal to 5 mg mL$^{-1}$, for instance, less than or equal to 2 mg mL$^{-1}$. These concentration ranges often favour networks in which the interfaces do not comprise bilayers.

The concentrations of amphipathic molecules referred to in the previous paragraphs are typically the concentrations of the amphipathic molecules in the hydrophobic medium, i.e. in the hydrophobic medium in which the plurality of hydrogel objects is disposed.

In some embodiments, the hydrogel network further comprises one or more further hydrogel objects, which further hydrogel objects comprise a hydrogel body.

Such a further hydrogel object does not necessarily comprise an outer layer of amphipathic molecules. Also, a further hydrogel object may or may not be in contact with any of the other hydrogel objects in the hydrogel network. A further hydrogel object may, for instance, be in contact with at least one of the other hydrogel objects in the hydrogel network but not in contact with any amphipathic molecules. This situation may arise, for example, if the further hydrogel object is surrounded by other hydrogel objects, and the interfaces between further hydrogel objects and the other objects do not comprise any amphipathic molecules. For example, the network may comprise a cube of 27 spherical hydrogel objects (three 3×3 layers) with the "further hydrogel object" occupying the central position, and the interface between the further hydrogel object and the other hydrogel objects may not comprise any layer of amphipathic molecules.

Alternatively, the "further hydrogel object" may be a "stand alone" hydrogel object which is not actually in contact with any of the other hydrogel objects in the network. See for instance, FIG. 7b-e, in which such a "stand alone" object is present.

The invention further provides an electrochemical circuit comprising a network of hydrogel objects which network comprises a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects. The network of hydrogel objects is as defined herein.

In the electrochemical circuit of the invention, the current is carried through the hydrogel network by ions.

Usually, the electrochemical circuit of the invention comprises a first electrode which is in contact with a said hydrogel object, and a second electrode.

The electrodes are typically electrochemically reversible electrodes. Usually, the first electrode and/or the second electrode comprises an electrochemically active electrode such as a Ag/AgCl electrode.

Alternatively, the electrodes may be a high work function metal (for instance gold, silver, nickel, palladium or platinum), if used in conjunction with an electrochemically active mediator such as ferrocyanide. For instance, a redox couple, or a member of a redox couple which may be partially oxidised or reduced to provide the redox couple, may be used. Suitable redox couples include those known in the art such as $Fe^{2+}/Fe^{3+}$, ferrocene/ferrocium or $Ru^{2+}/Ru^{3+}$. Examples of such are ferro/ferricyanide, ruthenium hexamine and ferrocene carboxylic acid.

Figure 7:
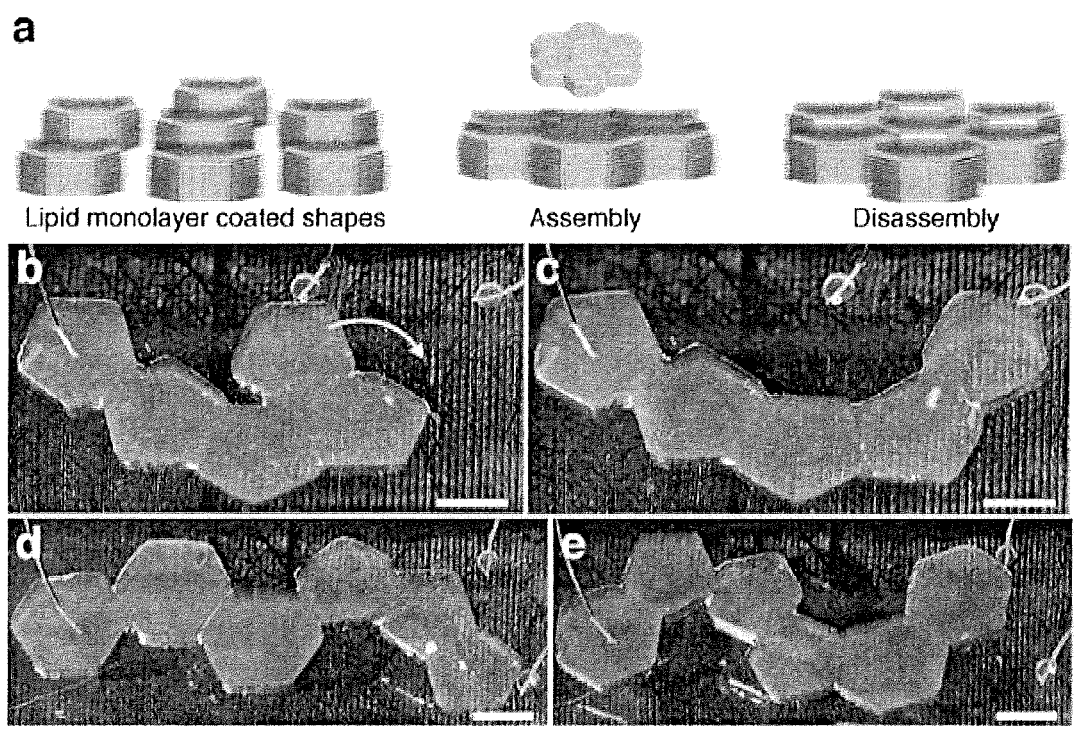
FIG. 7 relates to the self-assembly of hydrogel shapes.

In some embodiments, the second electrode is not in contact with any of said plurality of hydrogel objects in the hydrogel network. An example of an electrochemical circuit in which the second electrode is not in contact with any of said plurality of hydrogel objects in the hydrogel network is shown in FIG. 7. In other embodiments, the second electrode is in contact with at least one of said plurality of hydrogel objects in the hydrogel network.

As the skilled person will appreciate, the hydrogel objects in the hydrogel network could reconfigure to form a different arrangement. If this occurs, it is possible that, in one configuration the second electrode is not in contact with any of said plurality of hydrogel objects in the hydrogel network and in another configuration the second electrode is in contact with at least one of said plurality of hydrogel objects in the hydrogel network. Thus the electrochemical circuit could, for instance, form a switch or a component part of a switch.

Typically, the electrochemical circuit of the invention comprises a first electrode which is in contact with a said hydrogel object, and a second electrode, which second electrode is in contact with a different hydrogel object. The different hydrogel object that is in contact with the second electrode may be one of said plurality of hydrogel objects in the hydrogel network. Alternatively, the different hydrogel object that is in contact with the second electrode may not be one of said plurality of hydrogel objects in the hydrogel network. It may be a "further hydrogel object" of the kind described above, e.g., a "stand-alone" hydrogel object.

In some embodiments, the second electrode is in contact with another of said hydrogel objects of said plurality of hydrogel objects in the network.

In some embodiments, in the electrochemical circuit of the invention, at least one of said hydrogel bodies is a hydrogel wire. The hydrogel wire, or wire-shaped hydrogel body, is typically as herein defined. In some embodiments, at least two of said hydrogel objects is a hydrogel wire.

The electrochemical circuit may comprise many such wires that link together in the circuit. In this way complete circuits can be built up. Thus, for instance, all of the hydrogel bodies in the electrochemical circuit may be hydrogel wires.

Typically, the electrochemical circuit of the invention further comprises a hydrophobic medium, wherein the network is in contact with the hydrophobic medium.

In some embodiments, one or more of said hydrogel objects is disposed on a substrate. The substrate is usually non-conducting.

The substrate may, for instance, comprise glass or plastic. Thus the substrate may, for instance, be a Petri plate. The hydrogel objects may be any hydrogel object as defined herein.

In some embodiments, the substrate comprises a polymer. The repeat unit of the polymer may, for instance, comprise a —C(=O)O— or a —Si(CH$_3$)$_2$O— group. The polymer may, for instance, be PMMA (poly(methyl methacrylate)) or PDMS (polydimethylsiloxane).

The invention further provides an electrochemical circuit comprising a hydrogel network, which network comprises a plurality of hydrogel objects, wherein each of said hydrogel objects comprises a hydrogel body, and wherein each of said hydrogel objects contacts another of said hydrogel objects to form an interface between the contacting hydrogel objects. Usually the electrochemical circuit further comprises a first electrode which is in contact with a said hydrogel object, and a second electrode.

Thus the hydrogel objects in the hydrogel network of the electrochemical circuit do not necessarily comprise an outer layer of amphipathic molecules, on any part of the surface of the hydrogel body. When there is no outer layer of amphipathic molecules there is typically no bilayer of amphipathic molecules at the interface between the contacting hydrogel objects. In some embodiments, for example, the hydrogel objects are not in a hydrophobic medium.

The hydrogel body of one hydrogel object may for instance be in direct contact with the hydrogel body of another hydrogel object at least one of said interfaces between contacting hydrogel objects.

In some embodiments, the second electrode is not in contact with any of said plurality of hydrogel objects in the hydrogel network. In other embodiments, the second electrode is in contact with at least one of said plurality of hydrogel objects in the hydrogel network.

The hydrogel body may be as further defined hereinbefore.

Typically, the electrochemical circuit comprises said first electrode which is in contact with said hydrogel object and a second electrode which is in contact with another of said hydrogel objects.

In some embodiments, at least one of said hydrogel bodies is a hydrogel wire. Usually, the wire, or wire-shaped hydrogel body, is as defined herein. Typically, at least two of said hydrogel objects is a hydrogel wire. For instance, the electrochemical circuit may comprise three or more hydrogel objects in the shape of a wire. In some embodiments, at least half of the hydrogel bodies are hydrogel wires, for instance, all of the hydrogel bodies are hydrogel wires.

In the electrochemical circuit, there may, for instance be at least one hydrogel wire that is in contact with the first electrode or the second electrode. In some embodiments, there may be at least one of said hydrogel wires that is not in contact with the first electrode or the second electrode.

The electrochemical circuit may further comprise a hydrophobic medium, which hydrophobic medium is in contact with the hydrogel network. Typically, the hydrophobic medium is as defined herein.

In some embodiments, one or more of said hydrogel objects is disposed on a substrate. The substrate may be as further defined herein. The hydrogel objects may also be as further defined herein.

In one embodiment, any one of said plurality of hydrogel objects further comprises an outer layer of amphipathic molecules, on at least part of the surface of the hydrogel body. The amphipathic molecules may be as further defined herein. For instance, each of said plurality of hydrogel objects may further comprise an outer layer of amphipathic molecules, on at least part of the surface of the hydrogel body.

Usually, the concentration of amphipathic molecules is as defined hereinbefore.

The invention also provides a hydrogel component for a mechanical device, which hydrogel component comprises a hydrogel network, which network comprises a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects.

The frameworks of conventional machines and their parts (e.g. gears, screws, nuts and bolts) are made of hard components. However, the inventors have found that a hydrogel network can be used as part of a mechanical device (a "soft-matter mechanical device"), thus demonstrating that mechanical devices may comprise soft components. For example, a hydrogel network may be used to form at least part of the mechanical components required to switch electrical circuits. This is demonstrated in FIG. 15, which shows a cross-shaped hydrogel object, covered with a lipid monolayer, used as a manual switch in an electrical circuit.

Typically, in the hydrogel component of the invention, the network of hydrogel objects is as further defined herein.

In some embodiments, one or more of said hydrogel objects is, or forms part of, a moveable part.

The moveable component part may comprise all of said hydrogel objects. Alternatively, there may be additional hydrogel objects in the network that do not form part of said component part. There may be two or more component parts. In which case individual component parts may move independently from each other or may move together.

In some embodiments, one or more of said hydrogel objects forms a part which is moveable relative to one or more other hydrogel objects in the network. An example of a hydrogel component in which one or more of said hydrogel objects forms a part which is moveable relative to one or more other hydrogel objects in the network is a switch.

A variety of different stimuli may be used to move the moveable part.

The moveable part may, for instance, be moveable by the application of a magnetic force, an electromagnetic force, a mechanical force or a manual force. For instance, a magnetic material may be inserted into a hydrogel object, which object may then be moved by the application of an external magnetic field. (An external magnetic field may be applied, for instance, by bringing a magnet, such as a neodymium magnet, towards the hydrogel object or by switching on an electromagnetic field.) The magnetic material inserted into the hydrogel object may, for example, comprise a magnetic bead.

In some embodiments, the moveable part comprises a rotor or a component of a switch. The moveable part may, for instance, form part of an electrical circuit in which the moveable part is moved in order to switch the circuit on or off. Alternatively, the moveable part may form part of rotor.

When the hydrogel component forms a component of a switch, the switch may comprise at least three hydrogel objects. For instance, the switch may comprise two spherical hydrogel objects and a bar-shaped hydrogel object. In this configuration, the bar-shaped hydrogel object may, for instance, be rotated so that it is in contact with the two spherical hydrogel objects (for example to turn the switch on) or it may be rotated so that it is not in contact with the two spherical hydrogel objects (for example to turn the switch off).

Alternatively, the switch may comprise a cross-shaped hydrogel object. The switch may further comprise two spherical hydrogel objects. In some embodiments, the cross-shaped object may be rotated so that it is in contact with the two spherical hydrogel objects (for example to turn the switch on) or it may be rotated so that it is not in contact with the two spherical hydrogel objects (for example to turn the switch off). When the cross-shaped hydrogel object is in contact with the spherical hydrogel objects at least two interfaces will form, one interface between each spherical hydrogel object and the cross-shaped hydrogel object. A bilayer of amphipathic molecules may, for instance, form at least one of these interfaces. Typically, a bilayer of amphipathic molecules will form at both of these interfaces.

When the hydrogel component forms part of a rotor, the rotor may, for instance, be rotated using a magnetic field.

Usually, the rotor comprises at least five hydrogel objects. Typically, the rotor comprises at least one cross-shaped hydrogel object and four crescent-shaped hydrogel objects. More typically, the interfaces between the crescent-shaped hydrogel objects and the cross-shaped hydrogel object do not comprise a bilayer of amphipathic molecules. For instance, at the interfaces of the cross-shaped hydrogel object with each of the crescent-shaped hydrogel objects, the hydrogel objects may be in direct contact with each other. Thus, the cross-shaped hydrogel object may be in direct contact with four crescent-shaped hydrogel objects. One or more of said hydrogel objects may, for instance, comprise a magnet, such as a magnetic bead.

Further applications of hydrogel networks of the invention include, but are not limited to, providing a novel platform for the fundamental study of membrane proteins and acting as multi-compartment protocellular chassis for "bottom-up" synthetic biology. Thus, the hydrogel network can be used to make protocells and prototissues.

With respect to synthetic minimal tissues, hydrogel shapes are robust biocompatible building blocks with forms that cannot be retained by purely aqueous droplets. The hydrogel endows an aqueous compartment with a primitive cytoskeleton. For example, hydrogel bodies can be assembled into structures in which the building blocks can be separated with bilayers of amphipathic molecules, such as lipid bilayers. The structures may be readily rearranged and communication through the interface bilayers may be achieved with protein pores. By this means, electrical signalling through the structures or to contacting electrodes is possible. The versatility of the signalling may be enhanced by the use of extruded hydrogel wires or painted hydrogel connections. These wires and connections are analogs of neurons.

Thus, the invention also provides the use of a hydrogel network in synthetic biology. The hydrogel network may be as defined herein.

Further provided is the use of a hydrogel network of the invention as defined herein, or a composition of the invention as defined herein, in a method of preparing a protocell or an aggregate of protocells (prototissue).

The invention also provides the use of a hydrogel network as defined herein as a component of an electrochemical circuit or of a mechanical device. The electrochemical circuit or mechanical device may be as further defined herein.

In some embodiments, when the hydrogel network is used as a component of a mechanical device comprises, the hydrogel network comprises moveable parts. The moveable parts may be as defined herein. For instance, the hydrogel network may comprise a rotor. A hydrogel rotor may, for instance, be used as a droplet-collecting unit.

A droplet-collecting unit may comprise a rotor as herein defined. The droplet-collecting unit may be used to collect droplets around the rotor. The droplets may, for instance, be aqueous droplets or hydrogel bodies as herein defined. The collection of the droplets may be facilitated by the formation of bilayers of amphipathic molecules between the droplets and one of more of the hydrogel objects of the rotor. The droplets may, for instance, be collected as a result of the centripetal force created by the rotation of the rotor. Droplet-collecting units are shown in FIGS. 19 and 20. The experiments demonstrate the feasibility of using soft-matter components to fabricate mechanical devices for use in the bottom-up assembly of bilayer networks.

The invention also provides the use of a hydrogel network as defined herein as a switch or as a component part of a switch. The switch or component part of a switch may be as defined herein. For instance, the hydrogel network may be used as an electrochemical switch.

The hydrogel networks of the invention can be produced by the process of the invention for producing a hydrogel network, which hydrogel network comprises a plurality of hydrogel objects, wherein each of said hydrogel objects comprises: a hydrogel body, and an outer layer of amphipathic molecules, on at least part of the surface of the hydrogel body, wherein each of said hydrogel objects contacts another of said hydrogel objects to form an interface between the contacting hydrogel objects; which process comprises introducing a plurality of hydrogel bodies into a medium comprising a plurality of amphipathic molecules; and assembling said hydrogel bodies into a said network, or allowing said hydrogel bodies to self-assemble into a said network. The hydrogel network is as defined herein.

The hydrogel body is as herein defined. Usually, the hydrogel body is molded. For instance, PMMA molds of the desired shape may be used to produce the hydrogel bodies. Typically, the hydrogel is melted and poured into the mold. In some embodiments, at least one hydrogel body in the hydrogel network may comprise more than one hydrogel.

The hydrogel may be as herein defined. After gelling, the hydrogel is usually removed from the mold and immersed in a hydrophobic medium. To form a wire-shaped hydrogel body, warm hydrogel is typically drawn into a tube by capillary action. The warm hydrogel is then usually allowed to gel. The wire-shapes hydrogel bodies produced are typically wires as herein defined.

Alternatively, the hydrogel body may be shaped using light (such as UV light) from a light source and a photomask. The photomask is typically used to define a pattern through which the light can pass. Usually, the hydrogel body is shaped by shining light (such as UV light) through a photomask onto a photocurable polymer. The photocurable polymer is polymerised by the light. In this embodiment, the hydrogel comprises a photocurable polymer.

Typically, the medium is a hydrophobic medium as herein defined.

Usually, the amphipathic molecules are as herein defined.

Typically, the step of introducing a plurality of hydrogel bodies into a medium comprising a plurality of amphipathic molecules comprises introducing a plurality of hydrogel bodies into a hydrophobic medium, such as hexadecane, which hydrophobic medium comprises a plurality of amphipathic molecules. Usually, the amphipathic molecules comprise lipids, such as DPhPC.

In some embodiments, the hydrophobic medium comprises hexadecane, the amphipathic molecules comprise DPhPC and the hydrogel in the hydrogel bodies comprises agarose.

Typically, the hydrogel comprises agarose and water. The concentration of the agarose in water is typically less than or equal to 10% w/v agarose. For instance, the concentration of the agarose in said water may be from 0.25 to 5% w/v agarose. More typically, the concentration of the agarose in said water is from 0.5 to 4% w/v, for instance, from about 1% w/v to 3% w/v. Usually, the concentration of the agarose in said water is about 1% w/v or 3% w/v.

The hydrogel body may comprise a hydrophilic material, such as agarose, and a hydrophobic material.

Usually, the concentration of amphipathic molecules in the medium is less than or equal to 15 mg mL$^{-1}$. For instance, the concentration of amphipathic molecules may be from 0 to 10 mg mL$^{-1}$.

In some embodiments, the concentration of amphipathic molecules in the medium is usually equal to or greater than 0.5 mg mL$^{-1}$. For instance, the concentration of amphipathic molecules may be equal to or greater than 5 mg mL$^{-1}$. Usually, the concentration of amphipathic molecules is from 0.5 mg mL$^{-1}$ to 15 mg mL$^{-1}$, for instance, from 5 mg mL$^{-1}$ to 15 mg mL$^{-1}$. In order for a bilayer to form at an interface, the concentration of amphipathic molecules is usually equal to or greater than 1 mg mL$^{-1}$, for instance equal to or greater than 5 mg mL$^{-1}$.

In other embodiments, the concentration of amphipathic molecules in the medium is from 0.5 to 10 mg mL$^{-1}$. Usually, the concentration of amphipathic molecules is from 5 to 10 mg mL$^{-1}$. The inventors have found that these concentration ranges are favourable for stabilising hydrogel networks that comprise at least one interface that comprises a bilayer of amphipathic molecules and at least one other interface that does not comprise a bilayer of amphipathic molecules. Likewise, these concentration ranges have been found to favour hydrogel networks which comprise at least one interface that comprises a bilayer of amphipathic molecules, and at least one other interface at which the hydrogel body of one hydrogel object is in direct contact with the hydrogel body of another hydrogel object. The concentration of the amphipathic molecules may therefore be from 5 to 10 mg mL$^{-1}$.

In a further embodiment, the concentration of amphipathic molecules in the medium is less than or equal to 5 mg mL$^{-1}$, for instance, less than or equal to 2 mg mL$^{-1}$. These concentration ranges often favour networks in which the interfaces do not comprise bilayers.

The hydrogel bodies are assembled into a said network or allowed to self-assemble into a said network.

When the hydrogel bodies are assembled into a said network, the step of assembling said hydrogel bodies into a said network usually comprises manipulation of a hydrogel body, or two or more hydrogel bodies, to form an assembly of the desired arrangement of the hydrogel objects. The manipulation usually comprises manipulation of a hydrogel body, or two or more hydrogel bodies, using a needle. Typically the needle is a metal needle such as a steel needle.

When the hydrogel bodies are allowed to self-assemble into a said network, the step of allowing said hydrogel bodies to self-assemble into a said network typically comprises agitating the hydrogel bodies in the medium. The rate at which the hydrogel bodies self-assemble into the network will, of course, depend upon the viscosity of the medium and the concentration of amphipathic molecules in the medium. As the viscosity of the medium and/or the concentration of amphipathic molecules increases, the rate of self-assembly typically decrease.

In some embodiments, the process comprises: introducing a plurality of hydrogel bodies into a medium comprising a plurality of amphipathic molecules; assembling said hydrogel bodies into a said network; and allowing said hydrogel bodies to self-assemble into a said network.

In some embodiments, the process further comprises pushing together any two of said plurality of hydrogel objects in order to form an interface between said any two hydrogel objects which does not comprise a bilayer of amphipathic molecules. It is thought that the pushing together any two of said plurality of hydrogel objects effectively squeezes out the bilayer of amphipathic molecules at the interface and/or prevents a bilayer from forming at the interface in the first place or from re-forming at the interface. Thus, in these embodiments, the process produces a network comprising at least one interface that does not comprise a bilayer of amphipathic molecules. The skilled person will appreciate that any network defined herein that comprises at least one interface that does not comprise a bilayer of amphipathic molecules could be produced by this process.

The process may, for instance, further comprise pushing together any two of said plurality of hydrogel objects in order to form an interface between said any two hydrogel objects at which the hydrogel bodies of the two hydrogel objects are in direct contact with each other. Thus, the process may be used to produce a network comprising at least one interface at which the two hydrogel bodies at that interface are in direct contact with each other. The skilled person will appreciate that any network herein defined that comprises at least one interface at which the hydrogel objects at that interface are in direct contact with each other could be produced by this process.

In other embodiments, the process further comprises pulling apart any two of said plurality of hydrogel objects in order to form a bilayer of amphipathic molecules an interface between said two contacting hydrogel objects.

In some embodiments, when the hydrogel network comprises at least two interfaces, the process comprises: (i) pushing together the two hydrogel objects at the first interface in order to form an interface between said hydrogel objects which does not comprise a bilayer of amphipathic molecules; and (ii) pulling apart the two hydrogel objects at the second interface in order to form an interface between said any two hydrogel objects which comprises a bilayer of amphipathic molecules. For instance, the process may comprise: (i) pushing together the two hydrogel objects at the first interface in order to form an interface at which the two hydrogel bodies are in direct contact; and (ii) pulling apart the two hydrogel objects at the second interface in order to form an interface between said any two hydrogel objects which comprises a bilayer of amphipathic molecules.

Figure 5:
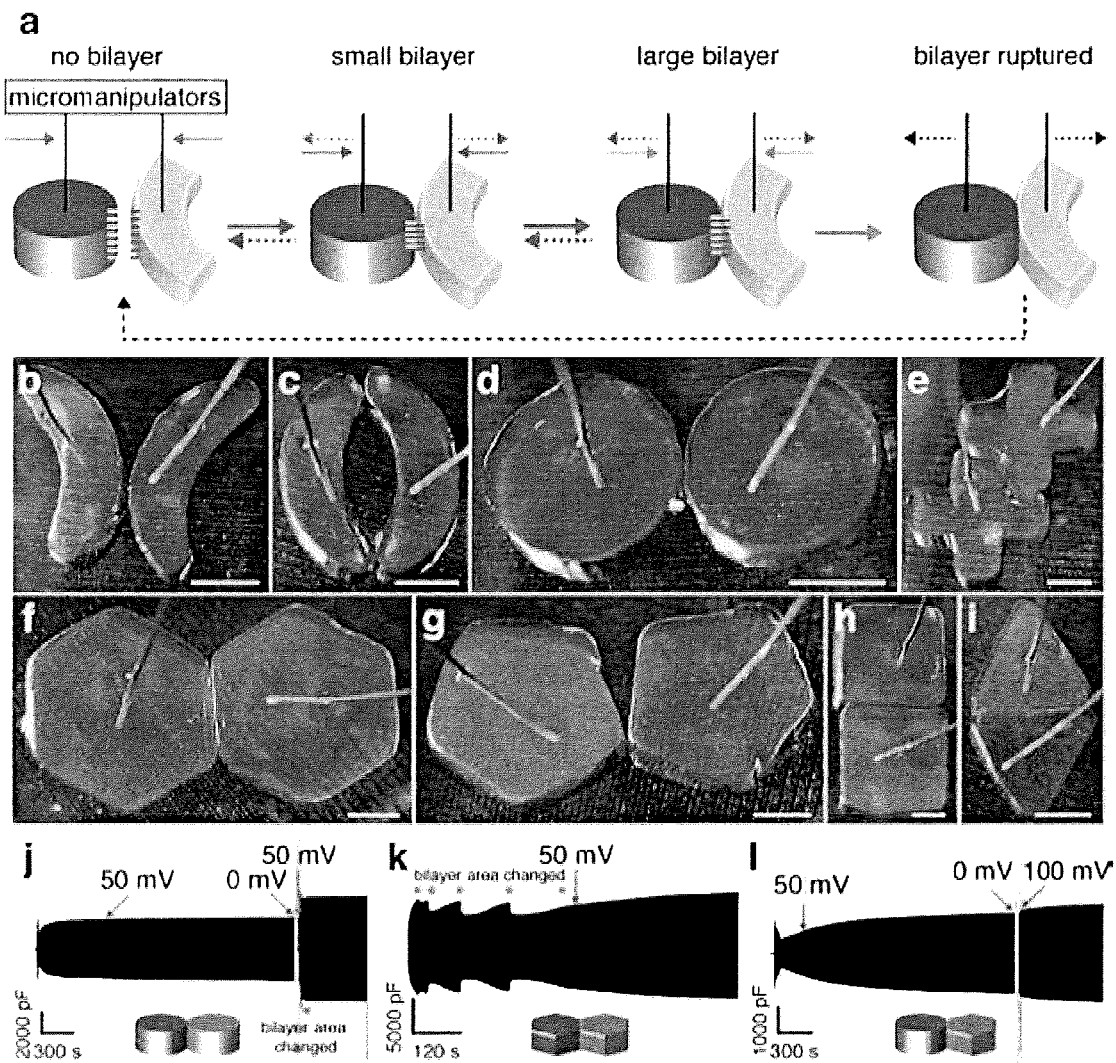
FIG. 5 depicts bilayers between various hydrogel shapes.

In some embodiments, the process further comprises pushing together or pulling apart any two of said plurality of hydrogel objects in order to adjust the size of the bilayer at any of said interfaces. (FIG. 5 provides an illustration of what typically happens to the size of the bilayer when the any two of said plurality of hydrogel objects are pushed together or pulled apart.) In these embodiments, the bilayer of amphipathic molecules is not completely squeezed out at the interface and the process produces a network comprising at least one interface that comprises a bilayer of amphipathic molecules. The skilled person will appreciate that any network defined herein that comprises at least one interface that comprises a bilayer of amphipathic molecules could be produced by this process. In some embodiments, when the hydrogel network comprises at least two interfaces, the process comprises: (i) pushing together the two hydrogel objects at the first interface in order to adjust the size of the bilayer at the first interface; and (ii) pulling apart the two hydrogel objects at the second interface in order to adjust the size of the bilayer at the second interface.

The process of the invention may further comprise adjusting the distance between any two of said hydrogel objects to: (a) form a bilayer of amphipathic molecules at the interface between said two hydrogel objects; (b) remove a bilayer of amphipathic molecules from the interface between said two hydrogel objects; or (c) change the area of the bilayer at the interface between said two hydrogel objects. In other embodiments, the process of the invention may further comprise adjusting the distance between any two of said hydrogel objects to adjust the size of the bilayer at the interface between said two hydrogel objects.

Usually, the distance between said any two hydrogel objects is adjusted using a micromanipulator.

In some embodiments, the concentration of the amphipathic molecules in said medium is adjusted in order to control the presence or absence of a bilayer of amphipathic molecules at the or each said interface.

As mentioned above, the concentration of amphipathic molecules required for the formation of a bilayer at an interface may depend upon the size and shape of the hydrogel body. Thus, the adjustment made to the concentration of the amphipathic molecules in said medium in order to control the presence or absence of a bilayer of amphipathic molecules at said interface will usually depend on the size and shape of the hydrogel bodies at that interface.

In some embodiments, when the concentration of the amphipathic molecules in said medium is adjusted in order to control the presence or absence of a bilayer of amphipathic molecules at said interface:

(i) the concentration of amphipathic molecules is adjusted from being greater than x to being less than or equal to x;

(ii) the concentration of amphipathic molecules is adjusted from being less than y to being equal to or greater than y;

(iii) the concentration of amphipathic molecules is adjusted from being less than or equal to x to being greater than x but less than y; or (iv) the concentration of amphipathic molecules is adjusted from being equal to or greater than y to being greater than x but less than y;

wherein x is 0.5 mg mL$^{-1}$, and y is 10 mg mL$^{-1}$.

x may, for instance, be 1 mg mL$^{-1}$ or 2 mg mL$^{-1}$. In some embodiments, x is 5 mg mL$^{-1}$.

In the process of the invention, the medium may, for instance, be a hydrophobic medium. The hydrophobic medium may, for instance, be a hydrophobic medium as defined hereinabove.

In one embodiment, the process of the invention further comprises introducing a volume of the hydrophobic medium, with the hydrogel network disposed therein, into a bulk hydrophilic medium, in the presence of amphipathic molecules. The volume may be a drop of the hydrophobic medium.

The bulk hydrophilic medium may, for instance, be an aqueous medium.

The process may therefore be used to form an encapsulate comprising a hydrogel network of the invention. Typically, the encapsulate comprises a volume (for instance a drop) of a hydrophobic medium; a peripheral layer of amphipathic molecules around the surface of the volume; and the hydrogel network within the peripheral layer. The amphipathic molecules which form the peripheral layer of the encapsulate may, in the process of the invention, be provided in the hydrophobic medium or in the bulk hydrophilic medium.

The process for producing a network of hydrogel objects, wherein the hydrogel objects are as defined herein, may further comprise recovering said network of hydrogel objects.

The invention also provides a network of hydrogel objects which is obtainable by a process as defined herein.

The present invention is further illustrated in the Examples which follow.

EXAMPLES

General Methods
Molding Hydrogel Shapes

Figure 2:
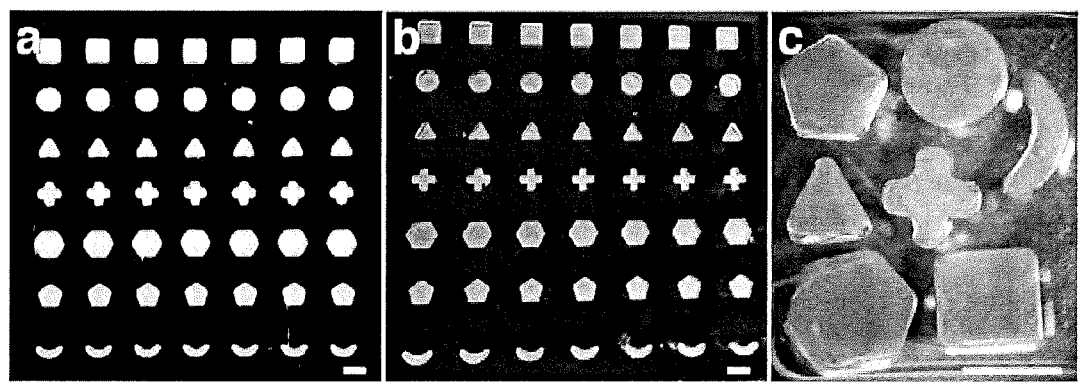
FIG. 2 relates to the molding of hydrogel shapes.

Millimeter-sized hydrogel shapes were fabricated with low melt agarose (1% w/v unless stated otherwise) (Sigma, Dorset, UK) in poly(methyl methacrylate) (PMMA) molds. A CNC machine was used to manufacture PMMA molds with the desired shapes (FIG. 2). Low-melt agarose (dissolved in 1 M KCl, 10 mM Tris•HCl, pH 7.0) was melted and poured into the mold. After gelling, the shapes were removed and immediately immersed in anhydrous hexadecane (≥99%) (Sigma-Aldrich, Dorset, UK), with or without dissolved lipids. The agarose wires were made in 0.5 mm (I.D.) borosilicate capillary tubes. Warm agarose solution was drawn into a tube by capillary action and allowed to gel. The capillary was broken, and the gelled wire pushed out by using a syringe needle.

Lipid Bilayers between Two Hydrogel Surfaces and Electrical Recording

The agarose shapes were incubated in a lipid/hexadecane mixture (1 to 10 mg mL$^{-1}$ DPhPC, Avanti Polar Lipids, Alabama, USA) for >1 h. To monitor bilayer formation, after incubation, two hydrogel shapes were impaled with Ag/AgCl electrodes and slowly brought into contact by using a micromanipulator. Bilayer formation was detected by an increase in the specific capacitance to a value of ~0.6 µF cm$^{-2}$. To record currents passed by αHL pores, wild-type or a mutant (2N) heptameric αHL protein (~200 nL) in liposomes made with DPhPC (1 mg mL-1), was absorbed on an agarose sphere (diameter 0.6-1.5 mm) and incubated in the lipid/hexadecane mixture for 10 to 15 min. Upon touching the agarose sphere to a lipid-monolayer coated agarose object, αHL insertion was observed by current recording. The current was amplified by using a patch-clamp amplifier (Axopatch 200B, Axon Instruments, USA), filtered with a low-pass Bessel filter (80 dB/decade) with a corner frequency of 1 kHz, and digitized with a Digidata 1322 A/D converter (Axon Instruments) at a sampling frequency of 10-20 kHz. In some cases, the data were low-pass filtered post-acquisition at 50 Hz.

Preparation of αHL Proteins

The WT-αHL heptamer was produced by purifying spontaneously oligomerized αHL from *Staphylococcus aureus* Wood 46 cultures as described elsewhere (Maglia, M. et al. Nano Lett 9, 3831-3836 (2009)). After purification the heptamer was stored in 20 mM sodium phosphate buffer, 150 mM NaCl, 0.3% (w/v) SDS, pH 8.0 at −80° C. The E111N/K147N (2N) αHL mutant was expressed as monomers in an *Escherichia coli* in vitro transcription translation system (IVTT) and assembled into heptamers on rabbit red blood cell membranes (Stoddart, D., Heron, A., Mikhailova, E., Maglia, G. & Bayley, H. Proc Natl Acad Sci USA 106, 7702-7707 (2009)).

Results

Lipid monolayers self-assemble on various shaped objects made from a hydrogel and immersed in a lipid/oil mixture (FIG. 1a). As described in detail below, depending on the lipid concentration in the oil and the force applied to the objects, the inventors have been able to (i) form bilayers between two millimeter-sized hydrogel shapes (with 1-5 mg mL$^{-1}$ 1,2-diphytanoyl-sn-glycero-3-phosphocholine (DPhPC) in hexadecane) by controlling the distance between the objects with a micromanipulator (FIG. 1b); (ii) form stable patterned assemblies with bilayers between more than two hydrogel shapes without the need for precision control with a micromanipulator (10 mg mL$^{-1}$ DPhPC) (FIG. 1c); (iii) self-assemble hydrogel shapes in arbitrary patterns without bilayers between the shapes (up to 5 mg mL$^{-1}$ DPhPC) and later rearrange the assemblies in patterns of specific designs (FIG. 1d); and (iv) build hydrogel networks with a bilayer between some shapes and none between the others (5-10 mg mL$^{-1}$ DPhPC) (FIG. 1e). A high lipid concentration (>5 mg mL$^{-1}$ DPhPC) is required to stabilize a bilayer network. However, even at high lipid concentrations, bilayers between hydrogel objects can be ruptured and expelled by applying a force to the objects that results in pressure normal to the bilayer surface.

Example 1

Bilayer Formation between Hydrogel Shapes

Figure 4:
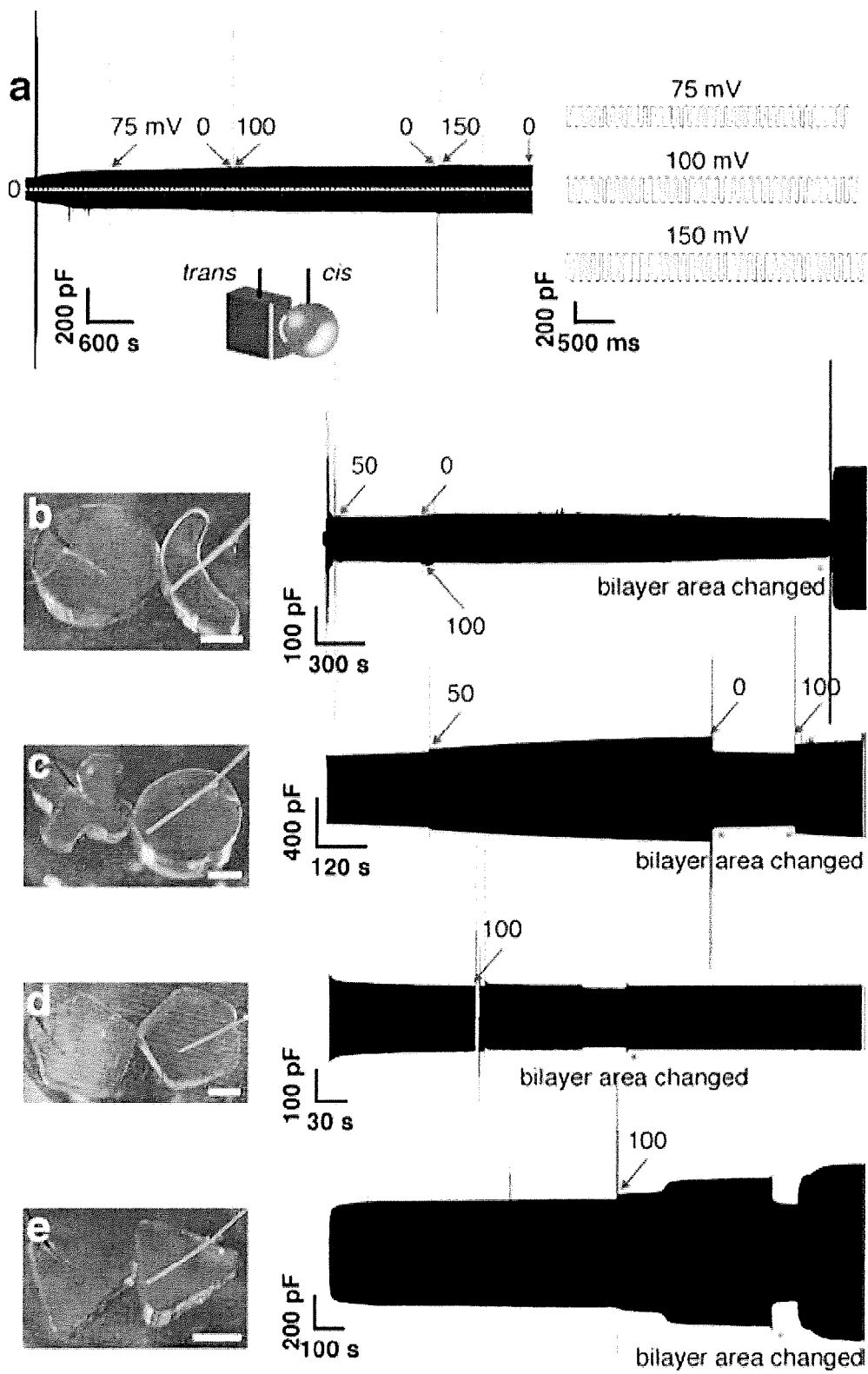
FIG. 4 relates to hydrogel-hydrogel bilayer stability.

The inventors supposed that two hydrogel objects, encased in lipid monolayers, brought close to each other with a micromanipulator, would form a bilayer at the interface, which could be functionalized by the incorporation of transmembrane pores (FIG. 1b,f). Lipid monolayers were formed on the surfaces of shaped hydrogel objects by immersion in a lipid/oil mixture (FIG. 2). When two lipid-coated hydrogel surfaces were brought together, a bilayer indeed formed between them, which was detected by an increase in specific capacitance to the anticipated value (FIG. 4). Assuming a circular bilayer, the specific capacitance of the bilayers formed between two hydrogels was determined to be 0.56±0.14 µF cm$^{-2}$ (average±S.D., n=11). This value is in good agreement with the reported value of ~0.65 µF cm$^{-2}$ (Gross, L. C., Heron, A. J., Baca, S. C. & Wallace, M. I. Langmuir 27, 14335-14342 (2011)).

Figure 3:
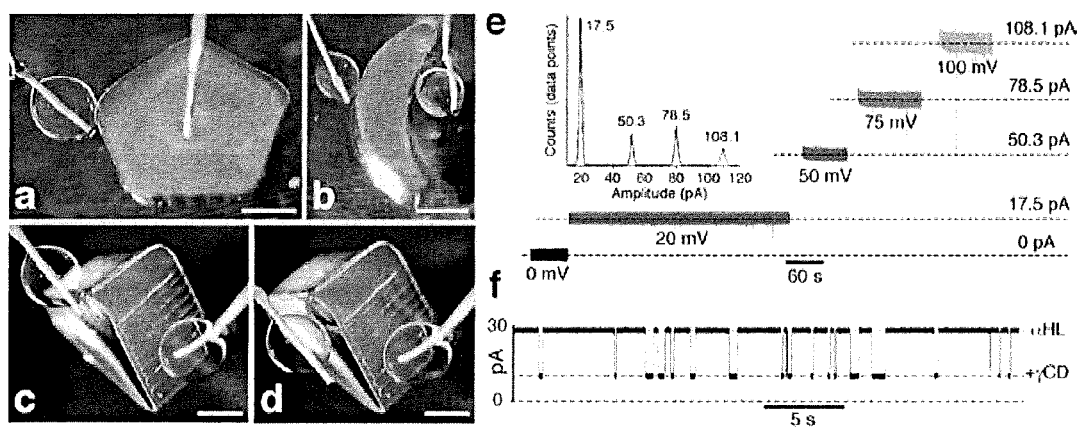
FIG. 3 demonstrates hydrogel-hydrogel interface bilayers. Various agarose shapes (1% w/v) were made with a PMMA mold (FIG. 2). A lipid monolayer self-assembled on the hydrogel shapes when they were immersed in a lipid/hexadecane (5 mg mL$^{-1}$ DPhPC) solution.

Initially, a hydrogel sphere was used to form bilayers with other hydrogel shapes. These hydrogel-hydrogel interface bilayers were stable (≥2 h) under an applied potential (+50 mV to +150 mV) (FIG. 4). An electrical connection between two hydrogel shapes could be established through staphylococcal α-hemolysin (αHL) pores inserted in the lipid bilayer (FIG. 3; FIG. 4, FIG. 13a,b). The integrity of the αHL pores was confirmed by using the E111N/K147N (2N) mutant of αHL and observing γ-cyclodextrin (γCD) binding. The residence time of γCD within the pore at +20 mV was 146±4 ms (average±S.D., n=562).

With a sphere against a flat hydrogel shape, the inventors measured a bilayer capacitance of up to 800 pF. Based on a specific capacitance of 0.65 µF cm$^{-2}$ (Gross, L. C., Heron, A. J., Baca, S. C. & Wallace, M. I. Langmuir 27, 14335-14342 (2011)), this value indicates a bilayer surface area of ~0.1 mm$^2$. Attempts to increase the bilayer area by pushing the sphere against the flat hydrogel surface by using a micromanipulator resulted in rupture of the bilayer. Stable millimeter-sized bilayers (up to ~2.5 mm$^2$) could be formed (1-5 mg mL$^{-1}$ DPhPC in hexadecane) by carefully bringing the flat faces of two hydrogel objects, such as hexagons, pentagons, cubes, cylinders and crosses, close to each other with a micromanipulator (FIG. 5; FIG. 4). A bilayer thus formed was ~20-times larger in area than a bilayer formed between a sphere and a flat surface. Bilayers could also be formed between surfaces with alternative curvatures. For example, two crescent-shaped hydrogels formed bilayers between their convex surfaces (FIG. 5b), and between the two horns of the crescents (FIG. 5c). Complementary regions of two objects could be fit in a lock-and-key arrangement with a bilayer at the interface (e.g., two crosses, FIG.

5e). Generally then, bilayers can be formed between shaped hydrogel objects in geometries that cannot be achieved with spherical aqueous droplets.

The area and hence the capacitance of a bilayer could be increased or decreased reversibly by pushing together or pulling apart two lipid-coated hydrogel shapes with a micromanipulator (FIG. 5j-l, Supplementary FIG. 4) (Gross, L. C., Heron, A. J., Baca, S. C. & Wallace, M. I. Langmuir 27, 14335-14342 (2011)). A bilayer could be ruptured by pushing the two faces hard against each other. Once ruptured, a bilayer could be quickly reformed by pulling the two hydrogel objects apart and bringing them back together.

Example 2

Hydrogel-hydrogel Bilayer Networks

Figure 6:
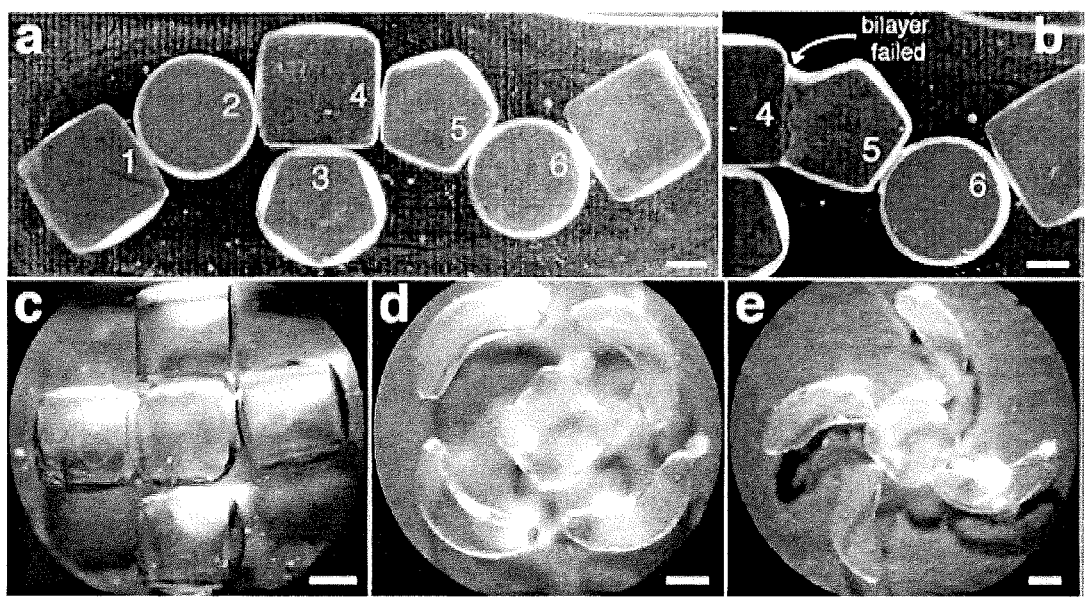
FIG. 6 represents hydrogel-hydrogel bilayer networks.

Agarose shapes, coated with a lipid monolayer (10 mg mL$^{-1}$ DPhPC in hexadecane), were assembled manually (by using a stainless steel needle) to form networks that featured bilayers in series and in branched structures (FIG. 6). Bilayers delimited the individual objects, because no dye transport was observed between them (FIG. 6a,b). Bilayer networks with altered patterns could be constructed by simple manual manipulation of the hydrogel shapes with a needle (FIG. 6c-e). The bilayer networks formed by the millimeter-sized hydrogel shapes was stable for up to 48 h (n=19).

Example 3

Hydrogel Assemblies without Bilayers

Figure 8:
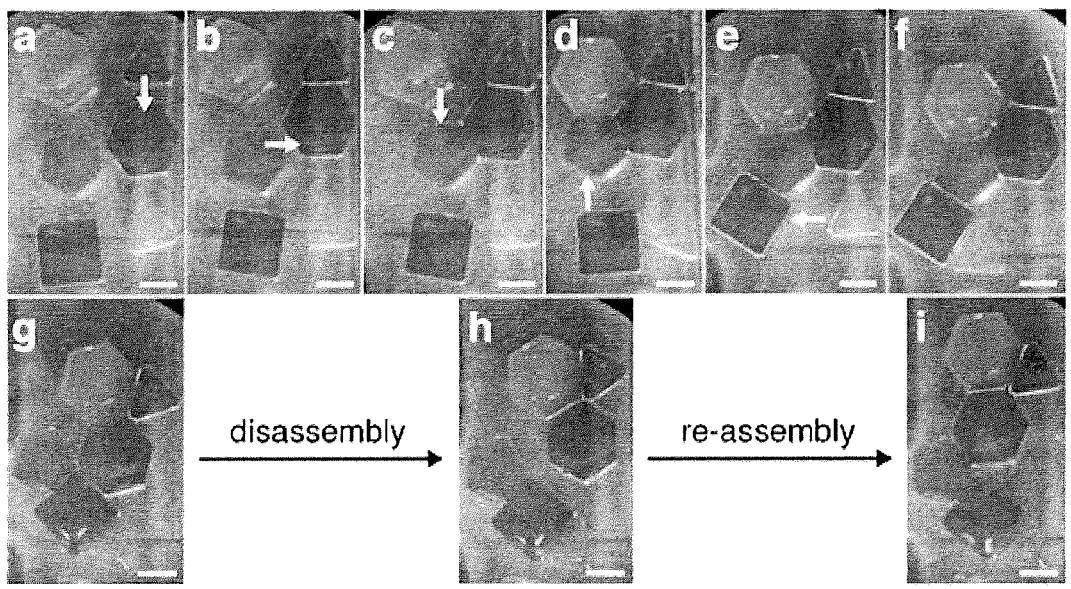
FIG. 8 relates to a hydrogel network comprising interfaces which do not comprise a bilayer of amphipathic molecules.

Hydrogel shapes were also used as building blocks to construct self-assembling networks to enable communication over macroscale (centimeter) distances. When agitated or mechanically stirred in hexadecane (with or without lipids), the hydrogel shapes formed arbitrarily arranged networks (FIG. 7a, FIG. 8). In this case, no lipid bilayers remained at the hydrogel-hydrogel interfaces after the assembly process. The networks could be altered by manipulation with a steel needle to form assemblies with desired arrangements of the hydrogel objects. Displacement of the lipid bilayer between two hydrogel objects maximizes the area of contact between the hydrophilic surfaces to form a thermodynamically stable configuration (Du, Y., Lo, E., Ali, S. & Khademhosseini, A. Proc Natl Acad Sci USA 105, 9522-9527 (2008)).

Example 4

Hydrogel Electrical Circuits

Figure 9:
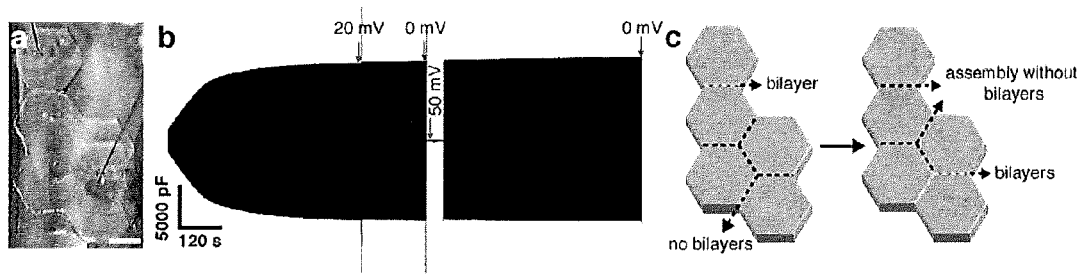
FIG. 9 relates to hydrogel networks comprising at least one interface comprising a bilayer and at least one interface that does not comprise a bilayer.

By utilizing the principles outlined above for hydrogel object assembly with or without lipid bilayers, the inventors were able to construct assemblies in which some hydrogel object pairs were connected by a bilayer whereas others had no bilayers between them (FIG. 9). DPhPC (5 mg mL$^{-1}$ in hexadecane) was used to assemble hydrogel networks without intervening bilayers in which the entire network was coated with a lipid monolayer. A stable bilayer between a hydrogel object and such a network was established by carefully controlling the distance between the object and the network with a micromanipulator (FIG. 9). The ability to move the hydrogel pieces manually in a network allowed reconfiguration of the electrical connections. For example, a network of pentagons was assembled without bilayers between the objects. An Ag/AgCl electrode was inserted in one of the terminal pentagons, and a bilayer was formed between the other terminal pentagon and one of two agarose spheres (diameter ~700 μm) on a branched Ag/AgCl electrode (FIG. 7b). By sliding the second pentagon to extend the configuration of the network, a new bilayer between that pentagon and the second agarose sphere was formed, while the first bilayer was broken (FIG. 7c). Similarly, an assembly of hexagons and pentagons was used to demonstrate a different change in configuration (FIG. 7d,e). An electrical node between a self-assembled network (without bilayers between the shapes) and a hydrogel shape was established by αHL pores (FIG. 13c,d).

Example 5

Hydrogel Wire

Wires are crucial components of any electrical device. Agarose was formed into long wires (>1 cm) of ~0.5 mm diameter by gelling within a capillary and extrusion. The wires were used to connect various hydrogel objects. For example, an agarose wire could be bent to form bilayers at two points on the same object (FIG. 10a,b). An agarose wire could also be used to link two hydrogel assemblies and serve as a flexible hinge to reconfigure the electrical connections (FIG. 10c,d). The transmission of information over centimeter distances by agarose wires was shown by the insertion of αHL pores into a bilayer formed between an agarose sphere and one end of a wire. Ion flow through the pores was detected by connecting an electrode to the other end of the wire (FIG. 13e,f). On a simple level, lipid monolayer-coated agarose wires mimic the axons of neurons (the diameter of a squid giant axon is 0.5 mm-1 mm).

Figure 11:
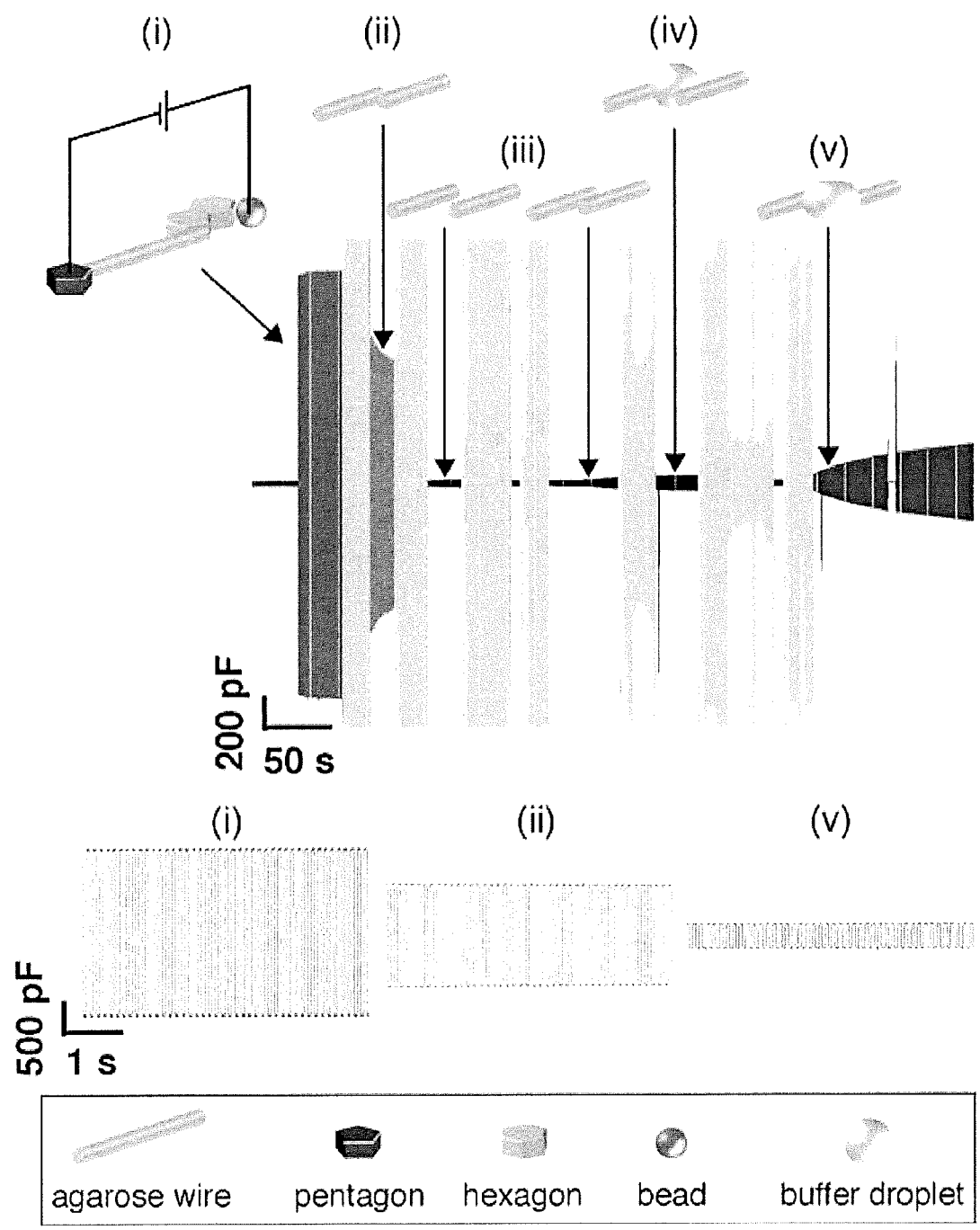
FIG. 11 relates to the resealing of a broken hydrogel wire. Moving from left to right across the figure: (i) A bilayer was formed between an agarose sphere (ground Ag/AgCl electrode) and two hexagons (5 mg mL$^{-1}$ DPhPC in hexadecane). An agarose wire was used to connect this network to a pentagon (active Ag/AgCl electrode). Bilayer formation between the agarose sphere and one of the hexagons was observed by monitoring the increase in capacitance at +20 mV; (ii) The wire was broken with a pair of tweezers but the two parts were in physical contact; (iii) The capacitance decreased to the basal level when the wires did not touch each other. A very small increase in the capacitance was observed when the two wires were physically contacted again. This may be owing to the absence of a low resistance path between the two cut wires; (iv) A 1 μL lipid droplet (1 mg mL$^{-1}$ DPhPC liposomes in 1 M KCl, 10 mM Tris, pH 7) was pipetted between the two wires; and (v) Upon fusion of the droplet with the agarose wires an increase in capacitance was observed. The bottom panel provides an enlarged view of the capacitance measurements and shows that a tight bilayer seal was observed at each step.

A soft wire is prone to damage. The inventors therefore devised ways to repair a broken wire in a hydrogel circuit. The circuit was constructed by forming a bilayer between an agarose sphere (on an Ag/AgCl electrode) and a hexagon in a two-hexagon assembly (with no bilayer between the objects). An agarose wire was used to connect one of the hexagons to an agarose pentagon penetrated by a Ag/AgCl electrode (FIG. 11). The formation of the only bilayer in the system, between the sphere and the hexagon, was monitored by an increase in capacitance. Upon cutting the agarose wire with a blade, and separating the two ends the capacitance fell to the background value. It sufficed to touch the two cut ends together to re-establish the electrical circuit. In a second approach, a broken agarose wire was resealed by connecting the severed ends with a buffer droplet or with a hydrogel object (FIG. 11).

Figure 12:
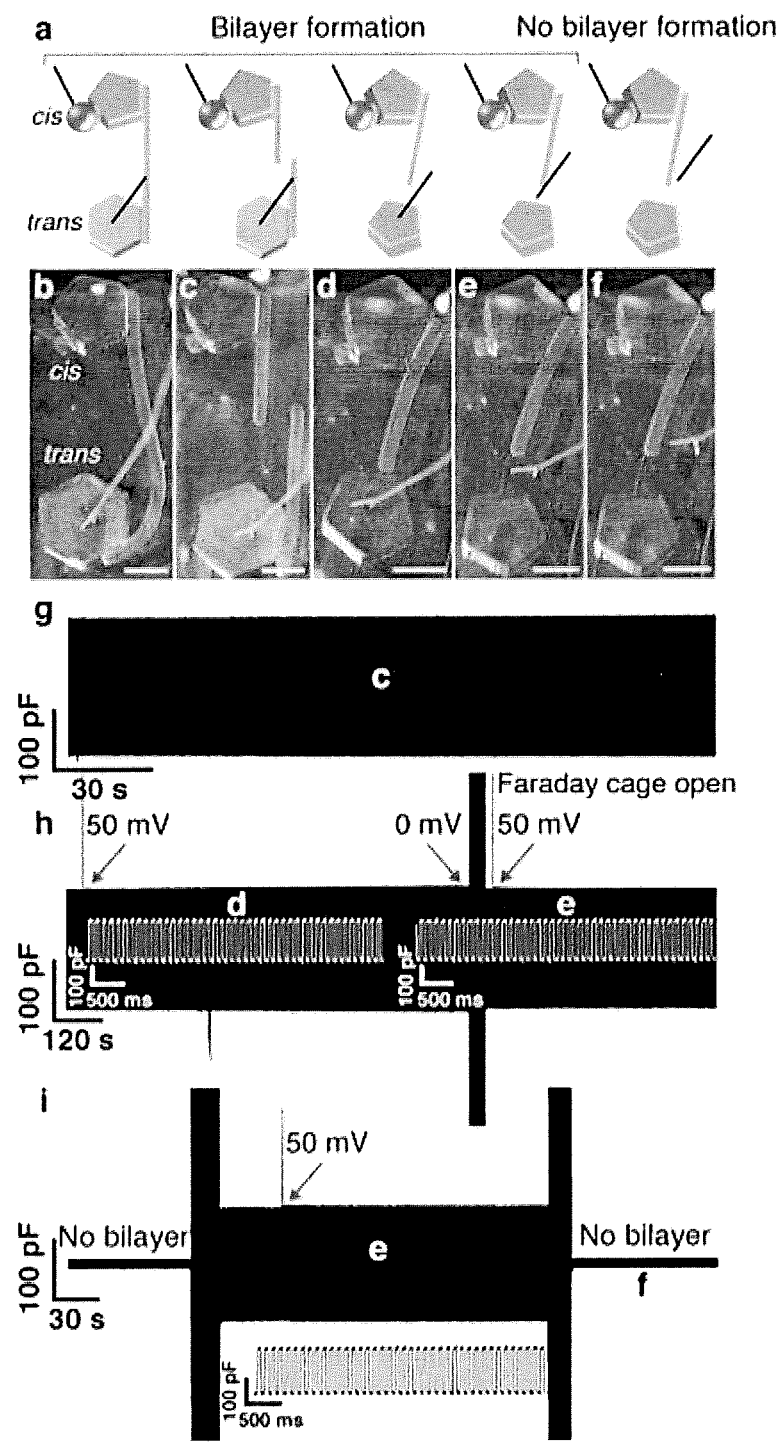
FIG. 12 relates to contact-free electrical communication between hydrogels.

Interestingly, the inventors could also reconnect an electrical circuit without apparent contact between the cut agarose wires. A bilayer was formed between an ~600 μm-diameter agarose sphere (on an Ag/AgCl electrode) and a pentagon shape, which was connected to a hexagon (on an Ag/AgCl electrode) via a hydrogel wire (FIG. 12a,b). After cutting the wire into two, the severed end of one of the wires was dragged manually to and from the other severed end on the PMMA surface (FIG. 12c). This process re-established the electrical connection between the two electrodes indicated by a specific capacitance of ~0.4 μF cm$^{-2}$ for the lipid bilayer between the agarose sphere and the pentagon (FIG. 12g). A similar phenomenon was observed after dragging an agarose object connected to an agarose wire. For example, a bilayer was formed between an agarose sphere (on an Ag/AgCl electrode) and a pentagon, which was connected to another pentagon (on an Ag/AgCl electrode) by an agarose wire (FIG. 12a,d). The pentagon on the electrode was dragged to and from the end of the agarose wire by using a micromanipulator. After this procedure, a specific capacitance value of ~0.7 g cm$^{-2}$ diagnostic of a bilayer was recorded even though the pentagon was not touching the agarose wire (FIG. 12d,h). Dragging a piece of agarose on a PMMA surface most probably painted a thin aqueous tube along the surface thereby forming a conductive path between the two electrodes. The inventors tested this idea by removing the electrode from the hydrogel pentagon and touching it on the PMMA surface where the hydrogel had been dragged. No change in the bilayer capacitance was observed signifying the presence of an electrical connection. After touching the electrode to part of the PMMA surface where the hydrogel had not been dragged, the capacitance decreased to the basal value (FIG. 12e,f,i).

Example 6

Painted Circuits

Inspired by this finding, the inventors made hydrogel-painted circuits (2 cm×2 cm to 6 cm×5 cm) analogous to conventional printed circuits boards (FIG. 14). Thin wires (diameter ~1-2 mm) of agarose were painted on a Petri plate with a 21-gauge needle (FIG. 14a,b). Interestingly, when the agarose wires were dried, they could be regenerated as conducting material by adding buffer or water to the dish (FIG. 14c,d). Small molecules (e.g., fluorescein or 5-cTAMRA) could be incorporated uniformly into the wires by inclusion in the original agarose or in the regenerating buffer. A proof-of-concept circuit was made by painting agarose wires onto a Petri plate, and placing two agarose shapes (a cube with 5-cTAMRA and a cylinder with fluorescein) at either end of the circuit. A bilayer was formed between an agarose sphere (on an Ag/AgCl electrode) and the cylinder (FIG. 14e,f). To establish the integrity of the bilayer, a second agarose sphere (on an Ag/AgCl electrode) was connected to the cube (with no bilayer in this case). A capacitance measurement of ~0.7 µF cm$^{-2}$ confirmed both bilayer formation at the cylinder and an electrical connection between the cylinder and the cube through the agarose wires (FIG. 14g). Such lipid-coated hydrogel wires connected to each other may be used to mimic neural circuits.

Example 7

Mechanical Devices

The frameworks of conventional machines and their parts (gears, screws, nuts, bolts, etc.) are made of hard components. The inventors show here that soft components, hydrogel objects, can be used as mechanical components to switch electrical circuits. For example, a cross-shaped hydrogel object, covered with a lipid monolayer, was used as a manual switch in an electrical circuit (FIG. 15a,b). Such a switch was able to form two bilayers simultaneously with two agarose spheres (FIG. 15c). Further, a magnetically-actuated switch was made by assembling a rectangular hydrogel bar and a hydrogel cube loaded with paramagnetic beads. There was no bilayer between the two hydrogel objects (FIG. 15d). The magnetic cuboid gel served as an actuator by causing the whole assembly to move under a magnetic field. The empty rectangular hydrogel bar connected, electrically and reversibly, two agarose spheres by the formation of lipid bilayers (FIG. 15e-g). A cross-shaped switch was made in a similar manner but with two magnetic cuboid actuators (FIG. 16). Simple mechanical elements such as these might be incorporated into the electrical circuits of functional devices.

A rotating device was constructed from a hydrogel cross and four crescents (FIG. 18). In this case, no bilayers were present between the cross and the crescent shapes of the rotor (cf. FIG. 6e). A crucial difference between the two assemblies formed of a cross and crescents (FIG. 6 and FIG. 18) is the contact area between their constituent shapes. The contact area was smaller in the bilayer network (FIG. 6e), which prevented expulsion of the bilayers and adhesion owing to surface tension, a dominant force when the hydrogel pieces have a large surface area (Bowden, N., Terfort, A., Carbeck, J. & Whitesides, G. M. Science 276, 233-235 (1997)). Automated rotation of the rotor was achieved by using a magnetic field. The objects forming the rotor were loaded with paramagnetic beads and the structure was rotated with a neodymium (Nd) magnet attached to a motor. When the magnet's axis was tilted at an angle ($\theta$~30°) to the structure's axis of rotation, the hydrogel rotor rotated, whereas at $\theta$=0, the rotor did not rotate (FIG. 17a). The direction of rotation of the structure, clockwise or counter-clockwise, depended on the angular velocity of the Nd magnet. When the magnet was rotated slowly in the clockwise direction, the structure rotated anti-clockwise (FIG. 17b-f). On increasing the clockwise angular velocity of the magnet, the rotation switched to the clockwise direction (FIG. 17g-k). Such a magnetic rotor could be used to form bilayers sequentially between the blades and a hydrogel sphere (FIG. 17l-p).

The magnetic hydrogel rotor was used to perform work as a droplet-collecting unit. The lipid monolayer coated hydrogel crescents of a rotor were used as sticky fingers to pick up lipid-encased aqueous droplets. Aqueous droplets strewn around the rotor were collected in the cusps of the structure as a result of the centripetal force generated by rotation under a magnetic field (FIG. 19). The process was facilitated by the formation of bilayers between the hydrogel shape and the droplets. Some droplets were located at positions where they were not collected as a result of the centripetal force. In these cases, the rotation was stopped with the crescent at the droplet location. The droplet then attached to the rotor by forming a bilayer with the crescent. The rotation of the magnet was re-started to capture the droplet (FIG. 20). These experiments demonstrate the feasibility of using soft-matter components to fabricate mechanical devices for use in the bottom-up assembly of bilayer networks.

CONCLUSIONS

In bottom-up synthetic biology, attempts are being made to use biological parts or materials to build materials ranging from nanodevices to minimal cells and tissues (Woolfson, D. N. & Bromley, E. H. C. The Biochemist February, 19-25 (2011); Payne, G. F. Curr Opin Chem Biol 11, 214-219 (2007); Wu, L.-Q. & Payne, G. F. Biofabrication: Trends Biotechnol 22, 593-599 (2004)). An area of interest for the application of the present invention is synthetic minimal tissues. Droplet networks are a favorable framework for exploration of the potential of such entities (Holden, M. A., Needham, D. & Bayley, H. J Am Chem Soc 129, 8650-8655 (2007)). Droplet networks have been produced that store and use energy (Holden, M. A., Needham, D. & Bayley, H. J Am Chem Soc 129, 8650-8655 (2007)), that form simple electrical circuits (Maglia, G. et al. Nat Nanotechnol 4, 437-440 (2009)), and that respond to signals such as light (Holden, M. A., Needham, D. & Bayley, H. J Am Chem Soc 129, 8650-8655 (2007)) or deliver chemicals to the external medium (Villar, G., Heron, A. & Bayley, H. Nat Nanotechnol 6, 803-808 (2011)). Networks that function in an aqueous environment, rather than oil, have recently been made (Villar, G., Heron, A. & Bayley, H. Nat Nanotechnol 6, 803-808 (2011)).

In the present work, the inventors have constructed networks by using shaped hydrogel objects as building blocks, rather than fluid aqueous droplets. Hydrogels have been used in numerous biomedical applications including drug delivery (Tokarev, I. & Minko, S. Adv Mater 22, 3446-3462 (2010); Zelikin, A. N., Price, A. D. & Stadler, B. Poly (methacrylic acid) polymer hydrogel capsules: drug carriers, sub-compartmentalized microreactors, artificial organelles, Small 6, 2201-2207 (2010)) and the provision of scaffolds for tissue engineering (Wheeldon, I., Farhadi, A., Bick, A. G., Jabbari, E. & Khademhosseini, A. Nanotechnology 22, 212001 (2011); Zhu, J. & Marchant, R. E. Expert Rev Med Devices 8, 607-626 (2011)). The assembly of shaped objects by the minimization of interfacial free energy was pioneered by Whitesides and colleagues (Choi, I. S., Bowden, N. & Whitesides, G. M. Macroscopic, Angew Chem Int Ed 38, 3078-3081 (1999); Bowden, N., Weck, M., Choi, I. S. & Whitesides, G. M. Acc Chem Res 34, 231-238 (2001)). Based on these studies, Khademhosseini made microgel pieces from a poly(ethylene glycol)-methacrylate polymer and had them self assemble in mineral oil (Du, Y., Lo, E., Ali, S. & Khademhosseini, A. Proc Natl Acad Sci USA 105, 9522-9527 (2008)). The assemblies were unstable when transferred to water, unless first crosslinked at the interfaces. These assemblies may prove useful for scaffolding living cells in tissue-like 3D patterns in vitro (Du, Y., Lo, E., Ali, S. & Khademhosseini, A. Proc Natl Acad Sci USA 105, 9522-9527 (2008)).

With respect to synthetic minimal tissues, hydrogel shapes are robust biocompatible building blocks with forms that cannot be retained by purely aqueous droplets. The hydrogel endows an aqueous compartment with a primitive cytoskeleton. Here, the inventors have shown that hydrogel shapes can be assembled into structures in which the building blocks can be separated with lipid bilayers. The structures can be readily rearranged and communication through the interface bilayers can be achieved with protein pores, as realized previously with droplets. By this means, electrical signalling through the structures or to contacting electrodes is possible. The versatility of the signalling can be enhanced by the of use extruded hydrogel wires or painted hydrogel connections. These wires and connections are analogs of neurons. The objects could also be made into mechanical devices, such as a rotor with alternating electrical contacts, which again could not be achieved without the rigidity of the hydrogel interior.

The invention might be extended in several directions. The assembly of hydrogel objects might be controlled by shape (Sacanna, S., Irvine, W. T., Chaikin, P. M. & Pine, D. J. Nature 464, 575-578 (2010)), surface energy (Tuteja, A., Choi, W., Mabry, J. M., McKinley, G. H. & Cohen, R. E. Proc Natl Acad Sci USA 105, 18200-18205 (2008); Williamson, A. J., Wilber, A. W., Doye, J. P. K. & Louis, A. A. Soft Matter 7, 3423-3431 (2011)) or molecular recognition (Leunissen, M. E. et al. Nat Mater 8, 590-595 (2009); Harada, A., Kobayashi, R., Takashima, Y., Hashidzume, A. & Yamaguchi, H. Nat Chem 3, 34-37 (2011)). Temperature, pH, light, chemicals, ions, and magnetic or electrical fields have been shown to act as stimuli for switching the shapes of hydrogels and might therefore be used to control assembly (Sidorenko, A., Krupenkin, T., Taylor, A., Fratzl, P. & Aizenberg, J. Science 315, 487-490 (2007); Yoo, J.-W. & Mitragotri, S. Proc Natl Acad Sci USA 107, 11205-11210 (2010); Jeong, B. & Gutowska, A. Trends Biotechnol 20, 305-311 (2002); Russew, M.-M. & Hecht, S. Adv Mater 22, 3348-3360 (2010)), as might surfaces with switchable properties (Lahann, J. et al. Science 299, 371-374 (2003); Synytska, A., Stamm, M., Diez, S. & Ionov, L. Langmuir 23, 5205-5209 (2007)). One long-term goal is the fabrication of biocompatible synthetic tissues for the delivery of therapeutic agents. Such synthetic tissues would have to be adapted to work in an aqueous environment, which has already been achieved with droplet networks (Villar, G., Heron, A. & Bayley, H. Nat Nanotechnol 6, 803-808 (2011)). The synthetic tissues might be autonomous or operate through external impetuses, such as light (Holden, M. A., Needham, D. & Bayley, H. J Am Chem Soc 129, 8650-8655 (2007)) or a magnetic field (as shown here in the Examples). Alternatively, synthetic tissues might be connected to electronic interfaces (Maglia, G. et al. Nat Nanotechnol 4, 437-440 (2009)).

Again, a direct interface between natural and synthetic tissues might be made, in which case the shape of the hydrogel compartments in contact with natural cells would be all important (Yoo, J.-W. & Mitragotri, S. Proc Natl Acad Sci USA 107, 11205-11210 (2010)). The ability to change shape, by further analogy with the cytoskeleton, might also be useful in this regard.

The work leading to this invention has received funding from the European Community's Seventh Framework Programme under grant agreement no. 236250.

The invention claimed is:

1. A hydrogel network comprising a plurality of hydrogel objects, wherein each of said hydrogel objects comprises:
   (a) a hydrogel body, and
   (b) an outer layer of amphipathic molecules, on at least part of the surface of the hydrogel body,
   wherein each of said hydrogel objects contacts another of said hydrogel objects to form an interface between the hydrogel objects;
   wherein said plurality of hydrogel objects comprises a first hydrogel object and a second hydrogel object, wherein each of the first and second hydrogel objects comprises:
   (a) a hydrogel body, and
   (b) an outer layer of amphipathic molecules, on at least part of the surface of the hydrogel body,
   wherein the first hydrogel object contacts the second hydrogel object to form an interface between the first and second hydrogel objects; and
   the hydrogel body of the first hydrogel object is in direct contact with the hydrogel body of the second hydrogel object, at the interface between the first and second hydrogel objects.

2. A hydrogel network according to claim 1 wherein the interface between the first and second hydrogel objects does not comprise a bilayer of amphipathic molecules.

3. A hydrogel network according to claim 1 wherein said plurality of hydrogel objects further comprises a third hydrogel object, wherein the third hydrogel object comprises:
   (a) a hydrogel body, and
   (b) an outer layer of amphipathic molecules, on at least part of the surface of the hydrogel body,
   wherein the first or second hydrogel object contacts the third hydrogel object to form an interface between the first or second hydrogel object and the third hydrogel object.

4. A hydrogel network according to claim 3 wherein the first hydrogel object contacts the third hydrogel object to form an interface between the first and third hydrogel objects, and wherein the second hydrogel object contacts the third hydrogel object to form an interface between the second and third hydrogel objects.

5. A hydrogel network according to claim 1 wherein the network comprises at least n of said hydrogel objects, and at least n−1 of said interfaces between hydrogel objects, wherein n is equal to or greater than 2.

6. A hydrogel network according to claim 3, wherein at least one of the interfaces between hydrogel objects comprises a bilayer of amphipathic molecules.

7. A hydrogel network according to claim 3 wherein at least one of the interfaces between hydrogel objects comprises a bilayer of amphipathic molecules, and at least one other of the interfaces between hydrogel objects does not comprise a bilayer of amphipathic molecules.

8. A hydrogel network according to claim 3 wherein at least one of the interfaces between hydrogel objects comprises a bilayer of amphipathic molecules, and wherein the hydrogel body of one hydrogel object is in direct contact with the hydrogel body of another hydrogel object at at least one other of the interfaces between hydrogel objects.

9. A hydrogel network according to claim 1 wherein the hydrogel body of at least one of said hydrogel objects is a molded three-dimensional hydrogel shape.

10. A hydrogel network according to claim 9 wherein the three-dimensional shape is spherical, cross-shaped, cuboid, crescent-shaped, prism-shaped, cylindrical, wire-shaped or a shape which has a triangular, pentagonal, hexagonal, heptagonal, octagonal, nonagonal, decagonal, undecagonal, dodecagonal, square or rectangular face.

11. A hydrogel network according to claim 1 wherein the hydrogel body of at least one of said hydrogel objects is in the shape of a wire.

12. A hydrogel network according to claim 8 wherein at least one of said bilayers further comprises a membrane protein, wherein the membrane protein is a pump, channel or a pore, a receptor protein, a transporter protein, or a protein which effects cell recognition or a cell-to-cell interaction.

13. A hydrogel network according to claim 1 wherein the hydrogel body comprises a hydrogel comprising agarose.

14. A hydrogel network according to claim 1, wherein the amphipathic molecules comprise lipid molecules.

15. A hydrogel network according to claim 1 which further comprises a hydrophobic medium, wherein the plurality of hydrogel objects is disposed in the hydrophobic medium.

16. A hydrogel network comprising a plurality of hydrogel objects,
wherein each of said hydrogel objects comprises:
(a) a hydrogel body, and
(b) an outer layer of amphipathic molecules, on at least part of the surface of the hydrogel body,
wherein each of said hydrogel objects contacts another of said hydrogel objects to form an interface between the hydrogel objects;
wherein at least one of said plurality of hydrogel objects is a Janus particle comprising:
(a) a hydrogel body comprising a hydrophilic material and a hydrophobic material, and
(b) an outer layer of amphipathic molecules, on at least part of the surface of the hydrogel body.

17. A hydrogel network according to claim 16, wherein the hydrophilic material is on one side of the hydrogel body and the hydrophobic material is on the other side of the hydrogel body.

* * * * *

UNITED STATES PATENT AND TRADEMARK OFFICE
CERTIFICATE OF CORRECTION

PATENT NO. : 9,831,010 B2
APPLICATION NO. : 14/438345
DATED : November 28, 2017
INVENTOR(S) : John Hagan Pryce Bayley and Kunwar Tanuj Sapra Page 1 of 1

It is certified that error appears in the above-identified patent and that said Letters Patent is hereby corrected as shown below:

In the Claims

In Claim 5, Column 51, Line 9, delete "wherein n is equal to or greater than 2" and insert -- wherein n is equal to or greater than 4 --

Signed and Sealed this
Twenty-ninth Day of May, 2018

Andrei Iancu
*Director of the United States Patent and Trademark Office*